US008119664B2

(12) United States Patent
Madar et al.

(10) Patent No.: US 8,119,664 B2
(45) Date of Patent: *Feb. 21, 2012

(54) PHARMACEUTICAL COMPOSITIONS AS INHIBITORS OF DIPEPTIDYL PEPTIDASE-IV (DPP-IV)

(75) Inventors: David J. Madar, Gurnee, IL (US);
Stevan W. Djuric, Libertyville, IL (US);
Melissa J. Michmerhuizen, Gurnee, IL (US); Hana A. Kopecka, Vernon Hills, IL (US); Xiaofeng Li, Gurnee, IL (US);
Kenton L. Longenecker, Grayslake, IL (US); Zhonghua Pei, Libertyville, IL (US); Daisy Pireh, Lake Forest, IL (US);
Hing L. Sham, Vernon Hills, IL (US);
Kent D. Stewart, Gurnee, IL (US);
Bruce G. Szczepankiewicz, Wildwood, IL (US); Paul E. Wiedeman, Deerfield, IL (US); Hong Yong, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/727,558

(22) Filed: Mar. 19, 2010

(65) Prior Publication Data

US 2010/0190822 A1 Jul. 29, 2010

Related U.S. Application Data

(60) Division of application No. 11/828,099, filed on Jul. 25, 2007, now abandoned, which is a division of application No. 10/788,993, filed on Feb. 27, 2004, now Pat. No. 7,262,207, which is a continuation-in-part of application No. 10/659,860, filed on Sep. 11, 2003, now abandoned.

(60) Provisional application No. 60/412,084, filed on Sep. 19, 2002.

(51) Int. Cl.
*A61K 31/445* (2006.01)
*C07D 295/00* (2006.01)

(52) U.S. Cl. ........ 514/326; 514/422; 514/318; 546/208; 546/276.4; 548/538; 548/518

(58) Field of Classification Search ............... 514/326, 514/422, 318; 546/208, 276.4; 548/538, 548/518
See application file for complete search history.

(56) References Cited

U.S. PATENT DOCUMENTS

| 5,691,356 | A | 11/1997 | Das et al. |
| 6,011,155 | A | 1/2000 | Villhauer |
| 6,172,081 | B1 | 1/2001 | Damon |
| 6,395,767 | B2 | 5/2002 | Robl et al. |
| 6,544,992 | B1 | 4/2003 | Dhanak et al. |
| 7,238,724 | B2 * | 7/2007 | Madar et al. ............ 514/422 |
| 7,262,207 | B2 * | 8/2007 | Madar et al. ............ 514/326 |
| 2005/0215784 | A1 | 9/2005 | Madar et al. |

FOREIGN PATENT DOCUMENTS

| WO | WO9301167 A1 | 1/1993 |
| WO | WO970832 A1 | 11/1997 |
| WO | WO9819998 | 5/1998 |
| WO | WO0134594 A1 | 5/2001 |
| WO | WO0168603 A2 | 9/2001 |
| WO | WO0196295 A2 | 12/2001 |
| WO | WO0230890 A1 | 4/2002 |
| WO | WO03084940 A1 | 10/2003 |
| WO | WO03092605 A2 | 11/2003 |
| WO | WO2004016587 A1 | 2/2004 |

OTHER PUBLICATIONS

Ahren, et al., "Inhibition of Dipeptidyl Peptidase IV Improves Metabolic Control Over a 4-Week Study Period in Type 2 Diabetes," Diabetes Care, 2002, vol. 25 (5), pp. 869-875.
Ahren, B., "Glucagon-like Peptide-1 (GLP-1): A Gut Hormone of Potential Interest in the Treatment of Diabetes," BioEssays, 1998, vol. 20 (8), pp. 642-651.
Barreto-Filho, et al., "Familial Isolated Growth Hormone Deficiency is Associated with Increased Systolic Blood Pressure, Central Obesity, and Dyslipidemia," The Journal of Clinical Endocrinology and Metabolism, 2002, vol. 87 (5), pp. 2018-2023.
Colao, et al., "The Cardiovascular Risk of Adult GH Deficiency (GHD) Improved after GH Replacement and Worsened in Untreated GHD: A 12-Month Prospective Study," Journal of Clinical Endocrinology and Metabolism, 2002, vol. 87 (3), pp. 1088-1093.
Cornish-Bowden, A., Fundamentals of Enzyme Kinetics, Portland press, 1995, Table of Contents.
Coutts, et al., "Structure-Activity Relationships of Boronic Acid Inhibitors of Dipeptidyl Peptidase IV. 1. Variation of the P2 Position of L5-boroPro Dipeptides," Journal of Medicinal Chemistry, 1996, vol. 39, pp. 2087-2094.
Deacon, et al., "Dipeptidyl Peptidase IV Inhibition Potentiates the insulinotropic Effect of Glucagon-like Peptide 1 in the Anesthetized Pig ," Diabetes, 1998, vol. 47, pp. 764-769.
Deacon, et al., "Both Subcutaneously and Intravenously Administered Glucagon-Like Peptide I Are Rapidly Degraded From the NH2-Terminus in Type II Diabetic Patients and in Healthy Subjects," Diabetes, 1995, vol. 44, pp. 1126-1131.
Drucker, D., "Perspectives in Diabetes Glucagon-Like Peptides," Diabetes, 1998, vol. 47, pp. 159-169.
Flint, et al., "Glucagon-like Peptide 1 Promotes Satiety and Suppresses Energy Intake in Humans," Journal of Clinical Investigation, 1998, vol. 101, pp. 515-520.
Gotherstrom, et al., "A Prospective Study of 5 Years of GH Replacement Therapy in GH-Deficient Adults: Sustained Effects on Body Composition, Bone Mass, and Metabolic Indices," Journal of Clinical Endocrinology and Metabolism, 2001, vol. 86 (10), pp. 4657-4665.

(Continued)

*Primary Examiner* — Rei-tsang Shiao
(74) *Attorney, Agent, or Firm* — Dianne Casuto

(57) ABSTRACT

The present invention relates to compounds which inhibit dipeptidyl peptidase IV (DPP-IV) and are useful for the prevention or treatment of diabetes, especially type II diabetes, as well as hyperglycemia, Syndrome X, hyperinsulinemia, obesity, atherosclerosis, and various immunomodulatory diseases.

30 Claims, No Drawings

OTHER PUBLICATIONS

Greene, et al., "Protection for the Amino group," Protective Groups in Organic Synthesis, 1999, Third Edition, pp. 494-653.

Gutniak, et al., "Antidiabetogenic Action of Glucagon-Like Peptide-1 Related to Administration Relative to Meal Intake in Subjects with 1 Type 2 Diabetes," Journal of Internal Medicine, 2001, vol. 250, pp. 81-87.

Gutzwiller, et al., "Glucagon-Like Peptide-1 Promotes Satiety and Reduces Food Intake in Patients with Diabetes Mellitus Type 2," American Physiological Society, 1999, vol. 276, pp. R1541-R1544.

Hughes, et al., "(1-[[[2-[(5-Cyanopyridin-2-yl)amino]ethyliamino]acetyll-2-cyano-(5)-pyrrolidine), a Slow-Binding Inhibitor of Dipeptidyl Peptidase IV," Biochemistry, 1999, vol. 38, pp. 11597-11603.

International Search Report for PCT/US03/29018, mailed Mar. 30, 2004.

Jain, R., "Convenient N-Protection of L-Pyroglutamic Acid Esters," Organic Preparations and Procedures International, 2001, vol. 33 (4), pp. 405-409.

Johannsson, et al., "Growth Hormone and the Metabolic Syndrome," Journal of Endocrinological Investigation, 1999, vol. 22, pp. 41-46.

Johannsson, et al., "Growth Hormone Treatment of Abdominally Obese Men Reduces Abdominal Fat Mass, Improves Glucose and Lipoprotein Metabolism, and Reduces Diastolic Blood Pressure," Journal of Clinical Endocrinology and Metabolism, 1997, vol. 82 (3), pp. 727-734.

Johannsson, et al., "Growth Hormone-Deficient Adults Are Insulin-Resistant," Metabolism, 1995, vol. 44 (9), pp. 1126-1129.

Juntti-Beggren, et al., "The Antidiabetogenic Effect of GLP-1 Is Maintained During a 7-Day Treatment Period and Improves Diabetic Dyslipoproteinemia in NIDDM Patients," Diabetes Care, 1996, vol. 19 (11), pp. 1200-1206.

Knudsen, et al., "Glucagon-Like Peptide-1-(9-36) Amide Is a Major Metabolite of Glucagon-Like Peptide-1-(7-36) Amide After in Vivo Administration to Dogs, and It Acts as an Antagonist on the Pancreatic Receptor ," European Journal of Pharmacology, 1996, vol. 318, pp. 429-435.

Kubiak, et al., "In Vitro Metabolic Degradation of a Bovine Growth Hormone-Releasing Factor Analog Leu27-Bgrf(1-29)Nh2 in Bovine and Porcine Plasma Correlation With Plasma Dipeptidylpeptidase Activity," Drug Metabolism and Disposition, 1989, vol. 17 (4), pp. 393-397.

Lankas, et al., "Inhibition of DPP819 Results in Toxicity in Preclinical Species: Potential Importance of Selective Dipeptidyl Peptidase IV Inhibition for the Treatment of Type 2 DM," Diabetic Supplies, 2004, vol. 2, pp. 1.

Le Noble, et al., "5-tert-Butyladamantan-2-one," Journal of Organic Chemistry, 1983, vol. 48 (7), pp. 1099-1101.

Li, et al., "Aminoacylpyrrolidine-2-nitriles: Potent and Stable Inhibitors of Dipeptidyl-Peptidase IV (CD 26)," Archives of Biochemistry and Biophysics, 1995, vol. 323 (1), pp. 148-154.

Mentlein, R., "Dipeptidyl-Peptidase IV (CD26)—Role in the Inactivation of Regulatory Peptides," Regulatory Peptides, 1999, vol. 85, pp. 9-24.

Mentlein, et al., "Dipeptidyl-Peptidase IV Hydrolyses Gastric Inhibitory Polypeptide, Glucagon-Like Peptide-L(7-36) Amide, Peptide Histidine Methionine and Is Responsible for Their Degradation in Human Serum," European Journal of Biochemistry, 1993, vol. 214, pp. 829-835.

Naslund, et al., "Glucagon-Like Peptide 1 Increases the Period of Postprandial Satiety and Slows Gastric Emptying in Obese Men," American Journal of Clinical Nutrition, 1998, vol. 68, pp. 525-530.

Nauck, et al., "Glucagon-Like Peptide 1 and its Potential on the Treatment of Non-Insulin-Dependent Diabetes Mellitus," Hormone and Metabolic Research, 2002, vol. 29, pp. 411-416.

Ohnuma, et al., "Soluble CD261Dipeptidyl Peptidase IV Induces T Cell Proliferation Through CD86 Up-Regulation on APCs," Journal of Immunology, 2001, vol. 167, pp. 6745-6755.

Ohtsuki, et al., "Negative Regulation of the Anti-Human Immunodeçciency Virus and Chemotactic Activity of Human Stromal Cell-Derived Factor 1k by Cd26/Dipeptidyl Peptidase Iv," Federation of European Biochemical Societies Letters, 1998, vol. 431, pp. 236-240.

Proost, et al., "Processing by Cd26/Dipeptidyl-Peptidase Iv Reduces the Chemotactic and Anti-Hiv-1 Activity of Stromal-Cell-Derived Factor-1k," Federation of European Biochemical Societies Letters, 1998, vol. 432, pp. 73-76.

Rachman, et al., "Near-Normalisation of Diurnal Glucose Concentrations by Continuous Administration of Glucagon-Like Peptide-1 (Glp-1) in Subjects With NIDDM," Diabetologia, 1997, vol. 40 (2), pp. 205-211.

Reaven, G., "Pathophysiology of Insulin Resistance in Human Disease," Physiological Reviews, 1995, vol. 75 (3), pp. 473-486.

Shioda, et al., "Anti-HIV-1 and Chemotactic Activities of Human Stromal Cell-Derived Factor 1a (Sdf-1a) and Sdf-1b are Abolished by Cd26ydipeptidyl Peptidase Iv-Mediated Cleavage," Proceedings of the National Academy of Sciences, 1998, vol. 95, pp. 6331-6336.

St. Denis, et al., "Potent Bicyclic Lactam Inhibitors of Thrombin: Part I: P3 Modifications," Bioorganic and Medicinal Chemistry Letters, 1998, vol. 8, pp. 3193-3198.

Tanaka, et al., "Enhancement of Antigen-Induced T-Cell Proliferation by Soluble Cd26/Dipeptidyl Peptidase lv (Cell-Mediated ImmunIty/CstImulatIon/Unemory T Cells)," Proceedings of the National Academy of Sciences, 1994, vol. 91, pp. 3082-3086.

Tanaka, et al., "The Costimulatory Activity of the CD26 Antigen Requires Dipeptidyl Peptidase Iv Enzymatic Activity," Proceeding of the National Academy of Sciences, 1993, vol. 90 (10), pp. 4586-4590.

Toft-Nielsen, et al., ""Continuous Subcutaneous Infusion of Glucagon-Like Peptide 1 Lowers Plasma Glucose and Reduces Appetite in Type 2 Diabetic Patients,"" Diabetes Care, 1999, vol. 22 (7), pp. 1137-1143.

Villhauer, et al., "1-[(3-Hydroxy-l-adamantyl)amino]acetyl]-2-cyano-(5)-pyrrolidine: A Potent, Selective, and Orally Bioavailable Dipeptidyl Peptidase Iv Inhibitor with Antihyperglycernic Properties," Journal of Medicinal Chemistry, 2003, vol. 46, pp. 2774-2789.

Weber, A., "Dipeptidyl Peptidase IV Inhibitors for the Treatment of Diabetes," Journal of Medicinal Chemistry, 2004, vol. 47 (17), pp. 4135-4141.

Zander, et al., "Additive Glucose-Lowering Effects of Glucagon-Like Peptide-1 and Metformin in Type 2 Diabetes," Diabetes Care, 2001, vol. 24 (4), pp. 720-725.

\* cited by examiner

PHARMACEUTICAL COMPOSITIONS AS INHIBITORS OF DIPEPTIDYL PEPTIDASE-IV (DPP-IV)

CROSS REFERENCE TO RELATED APPLICATION

This application is a divisional application of U.S. patent application Ser. No. 11/828,099, filed Jul. 25, 2007, which is a divisional application of U.S. patent application Ser. No. 10/788,993, filed Feb. 27, 2004, which is a continuation in part of U.S. patent application Ser. No. 10/659,860, filed Sep. 11, 2003, which claims the benefit of U.S. Provisional Application Ser. No. 60/412,084, filed on Sep. 19, 2002, all of which are incorporated by reference in their entirety.

FIELD OF THE INVENTION

The present invention relates to compounds which inhibit dipeptidyl peptidase IV (DPP-IV) and are useful for the prevention or treatment of diabetes, especially type II diabetes, as well as hyperglycemia, Syndrome X, hyperinsulinemia, obesity, atherosclerosis, and various immunomodulatory diseases.

BACKGROUND OF THE INVENTION

Dipeptidyl peptidase IV (DPP-IV, CD26, EC 3.4.14.5) is a serine protease with specificity for cleaving Xaa-Pro and, to a lesser extent, Xaa-Ala dipeptides from the N-termini of polypeptides and proteins. DPP-IV is a non-classical serine protease in that the catalytic triad of Ser-Asp-His, found in the C-terminal region of the enzyme, is in reverse order to that found in classical serine proteases. DPP-IV is widely expressed in mammalian tissue as a type II integral membrane protein. DPP-IV is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates including chemokines such as, RANTES (regulated on activation normal T cell expressed and secreted), eotaxin, and macrophage-derived chemokine, neuropeptides such as NPY (neuropeptide Y) and substance P, vasoactive peptides, and incretins such as GLP-1 (glucagon-like peptide-1) and GIP (gastric inhibitory peptide/glucose-dependent insulinotropic polypeptide). GLP-1 is a 30 amino acid peptide hormone produced in the L cells of the distal small intestine in response to ingested nutrients. GLP-1 binding to its receptor on various tissues stimulates insulin gene expression, biosynthesis and glucose-dependent insulin secretion, inhibits glucagon secretion, promotes satiety, slows gastric emptying and promotes growth of pancreatic beta cells. Based on this profile, GLP-1-based therapies are expected to be beneficial in the treatment of type II diabetes and obesity. Studies in which type II diabetic patients have been infused with GLP-1 have demonstrated efficacy in normalizing both fasted and prandial glycemia. However, active GLP-1 (7-36) amide is rapidly converted by DPP-IV to GLP-1 (9-36), which is inactive or is a receptor antagonist. The short half-life of GLP-1 in the circulation (1-1.5 minutes) is a major obstacle to its use as a therapeutic agent. To circumvent the drawback of the short half-life of GLP-1, inhibitors of DPP-IV, the primary degradative enzyme of GLP-1, increase the level of active circulating GLP-1 (7-36) amide. DPP-IV inhibitors have been demonstrated to improve glucose tolerance in type II diabetes.

Therefore, the inhibition of DPP-IV can provide therapeutic treatment for type II diabetes.

SUMMARY OF THE INVENTION

The present invention is directed to compounds of formula (I),

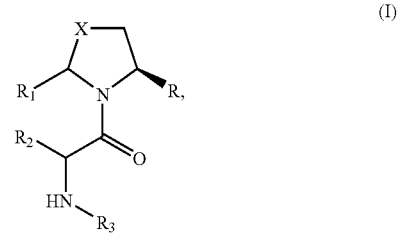

or pharmaceutically acceptable salts or prodrugs thereof, wherein

X is a member selected from the group consisting of $CH_2$, CHF and $CF_2$;

R is a member selected from the group consisting of alkylcarbonyl, arylcarbonyl, cyano, heterocyclecarbonyl, $R_4R_5NC(O)$—, $B(OR_6)_2$, (1,2,3)-dioxoborolane and 4,4,5,5-tetramethyl-(1,2,3)-dioxoborolane;

$R_1$ is a member selected from the group consisting of alkoxyalkyl, alkyl, alkylcarbonyl, alkenyl, alkynyl, allenyl, arylalkyl, cycloalkyl, cycloalkylalkyl, cyano, haloalkyl, haloalkenyl, heterocyclealkyl, and hydroxyalkyl;

$R_2$ and $R_3$ are independently selected from the group consisting of hydrogen, alkoxyalkyl, alkyl, alkenyl, alkynyl, cycloalkyl, cycloalkylalkyl, aryl, arylalkyl, heterocycle, heterocyclealkyl, and hydroxyalkyl; or $R_2$ and $R_3$ taken together with the atoms to which they are attached form a mono or bicyclic heterocycle selected from the group consisting of 2-indolinyl, 2-indolyl, 3-isoquinoline, 2-piperazine, 2-piperidine, 2-pyrrolidine, 2-pyrrole, 2-pyridine, 2-quinolinyl, 2-tetrahydroquinolinyl, and 3-tetrahydroisoquinolinyl, wherein said heterocycle may be substituted with 0, 1, 2 or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, hydroxy, hydroxyalkyl, mercapto, nitro, phenyl, $R_AR_BN$—, $R_CR_DNC(O)$—, and $R_CR_DNS(O)_2$—;

$R_4$, $R_5$ and $R_6$ are each independently selected from the group consisting of hydrogen, alkyl, and arylalkyl;

$R_A$ and $R_B$ are each independently selected from the group consisting of alkyl, alkylcarbonyl, alkoxycarbonyl, alkylsulfonyl; or $R_A$ and $R_B$ taken together with the nitrogen to which they are attached form a ring selected from the group consisting of piperidine, piperazine and morpholine; and $R_C$ and $R_D$ are each independently selected from the group consisting of hydrogen and alkyl.

According to an embodiment of the present invention, there is provided a method to improve glucose tolerance in type II diabetes comprising administering a therapeutically effective amount of a compound of formula (I). According to another embodiment of the present invention, there is provided a method for treating type 2 diabetes, insulin resistance, hyperinsulinemia, impaired glucose tolerance, obesity, hypercholesterolemia, and hypertriglyceridemia comprising administering a therapeutically effective amount of a compound of formula (I).

According to still another embodiment, the present invention is directed to pharmaceutical compositions comprising a therapeutically effective amount of a compound of formula (I) in combination with a pharmaceutically acceptable carrier.

DETAILED DESCRIPTION OF THE INVENTION

Definitions

As used throughout this specification and the appended claims, the following terms have the following meanings.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. The alkyl groups of the present invention may be optionally substituted with 0, 1 or 2 substituents that are members selected from the group consisting of alkoxy, alkoxycarbonyl, alkylcarbonyl, alkylcarbonyloxy, alkylsulfonyl, alkylthio, carboxy, carboxyalkyl, cyano, cyanoalkyl, formyl, halogen, hydroxy, alkoxycarbonylNR$_g$, alkylNR$_g$ wherein R$_g$ is a member selected from the group consisting of hydrogen and alkyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The alkynyl groups of this invention can be substituted with 0, 1, 2, or 3 substituents independently selected from alkoxy, alkoxyalkyl, alkoxycarbonyl, alkoxycarbonylalkyl, alkylcarbonyl, alkylcarbonylalkyl, heterocycle, heterocyclealkyl, hydroxy, and hydroxyalkyl.

The term "allenyl," as used herein, refers to a straight or branched chain hydrocarbon containing from 3 to 10 carbons and containing two double bonds between three contiguous carbons formed by the removal of four hydrogens. Representative examples of alkenyl include, but are not limited to, propa-1,2 dienyl, penta-1,2 dienyl, penta-2,3 dienyl, hexa-1,2-dienyl and the like.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of the present invention can be substituted with 0, 1, 2, or 3 substituents independently selected from alkyl, alkenyl, alkoxy, alkoxyalkyl, alkoxycarbonyl, alkoxycarbonylalkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, heterocycle, heterocyclealkyl, hydroxy, hydroxyalkyl, mercapto, nitro, phenyl, R$_E$R$_F$N—, R$_G$R$_H$NC(O)—, and R$_G$R$_H$NS(O)$_2$—, wherein R$_E$ and R$_F$ are each independently selected from the group consisting of alkyl, alkylcarbonyl, alkoxycarbonyl, alkylsulfonyl, and R$_G$ and R$_H$ are each independently selected from the group consisting of hydrogen and alkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "carbonyl," as used herein, refers to a —C(O)— group.

The term "carboxy," as used herein, refers to a —CO$_2$H group.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1) heptane, bicyclo(2.2.1)heptane, bicyclo(2.2.2)octane, bicyclo(3.2.2)nonane, bicyclo(3.3.1)nonane, and bicyclo(4.2.1) nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo(3.3.1.0$^{3,7}$)nonane and tricyclo(3.3.1.1$^{3,7}$)decane (adamantane).

The cycloalkyl groups of this invention may be substituted with 0, 1, 2 or 3 substituents selected from alkyl, alkylcarbonyl, alkoxy, alkoxycarbonyl, alkenyl, alkynyl, aryl, cyano, halogen, hydroxy, hydroxyalkyl, nitro, $R_E R_F N$—, $R_G R_H NC(O)$—, and $R_G R_H NS(O)_2$—, wherein $R_E$ and $R_F$ are each independently selected from the group consisting of alkyl, alkylcarbonyl, alkoxycarbonyl, alkylsulfonyl, and $R_G$ and $R_H$ are each independently selected from the group consisting of hydrogen, arylalkyl, heterocyclealkyl, heterocycle and alkyl.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkenyl," as used herein, refers to at least one halogen, as defined herein, appended to the parent molecular moiety through an alkenyl group, as defined herein. Representative examples of haloalkenyl include, but are not limited to, chloroethylenyl, 2-fluoroethylene, trifluorobutenyl, and dichloropropenyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

According to the present invention, heterocycles can be substituted with 0, 1, 2 or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, hydroxy, hydroxyalkyl, mercapto, nitro, phenyl, sulfonyl, $R_E R_F N$—, $R_G R_H NC(O)$—, and $R_G R_H NS(O)_2$—, wherein $R_E$ and $R_F$ are each independently selected from the group consisting of alkyl, alkylcarbonyl, alkoxycarbonyl, alkylsulfonyl, and $R_G$ and $R_H$ are each independently selected from the group consisting of hydrogen and alkyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "heterocyclecarbonyl," as used herein, refers to a heterocycle, as defined herein, appended to the parent molecular moiety through an carbonyl group, as defined herein. Representative examples of heterocyclecarbonyl include, but are not limited to, pyridin-3-ylcarbonyl and 2-pyrimidin-2-ylcarbonyl and the like.

The term "nitro," as used herein, refers to a —NO$_2$ group.

The present invention is directed to compounds of formula (I), wherein R, $R_1$, $R_2$, $R_3$, $R_4$, $R_5$, $R_6$, $R_A$, $R^B$, $R_C$ and $R_D$ are defined herein.

The present invention is also directed to a method of treating disorders mediated by DPP-IV through inhibition of enzymatic activity. Disorders known to be regulated through enzymatic activity are diabetes, especially type II diabetes, as well as hyperglycemia, Syndrome X, hyperinsulinemia, obesity, atherosclerosis, various immunomodulatory diseases. Therefore, according to an embodiment of the present invention there are provided compounds of formula (I), which are useful for the treatment of diabetes, especially type II diabetes, as well as hyperglycemia, Syndrome X, hyperinsulinemia, obesity, atherosclerosis, and various immunomodulatory diseases.

According to a further embodiment of the present invention there is provided a compound of formula (I), wherein R is cyano and wherein X, $R_1$, $R_2$, $R_3$, $R_4$, $R_5$ and $R_6$ are as defined in formula (I).

According to a further embodiment of the present invention there is provided a compound of formula (I), wherein R is cyano; $R_1$ is a member selected from the group consisting of alkyl, alkenyl, alkynyl, and cycloalkyl and wherein X, $R_2$, and $R_3$ are as defined in formula (I).

According to a further embodiment of the present invention there is provided a compound of formula (I), wherein R is cyano; $R_1$ is a member selected from the group consisting of alkyl, alkenyl, and alkynyl; $R_2$ is a member selected from the group consisting of alkoxyalkyl, alkyl, cycloalkyl, cycloalkylalkyl, arylalkyl, and heterocyclealkyl and wherein X, and $R_3$ are as defined in formula (I).

According to a further embodiment of the present invention there is provided a compound of formula (I), wherein R is cyano; $R_1$ is a member selected from the group consisting of alkyl, alkenyl, and alkynyl; $R_2$ is selected from the group consisting of alkyl, cycloalkyl, and heterocycle; $R_3$ is hydrogen and wherein X is as defined in formula (I).

According to a further embodiment of the present invention there is provided a compound of formula (I), wherein R is cyano; $R_1$ is a member selected from the group consisting of alkynyl, wherein alkynyl is ethynyl and propynyl; $R_2$ is a member selected from the group consisting of alkyl, cycloalkyl, and heterocycle; $R_3$ is hydrogen and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is a member selected from the group consisting of alkyl, cycloalkyl, and heterocycle; $R_3$ is cycloalkyl, wherein cycloalkyl is a member selected from the group consisting of cyclopropyl, cyclobutyl, cyclopentyl, cycloheptyl, and cyclooctyl and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ is hydrogen; $R_3$ is cycloalkyl, wherein cycloalkyl is a member selected from the group consisting of cyclopropyl, cyclobutyl, cyclopentyl, cycloheptyl, and cyclooctyl and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is hydrogen; and $R_3$ is cycloalkyl, wherein cycloalkyl is a member selected from the group consisting of cyclopropyl, cyclobutyl, cyclopentyl, cycloheptyl, and cyclooctyl and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is a member selected from the group consisting of alkyl, cycloalkyl, and heterocycle; and $R_3$ is $R_9$—O-cyclohexyl; $R_9$ is a member selected from the group consisting of hydrogen, aryl, and heterocycle and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ is hydrogen; and $R_3$ is

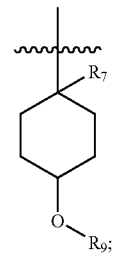

$R_9$ is a member selected from the group consisting of hydrogen, aryl, and heterocycle and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is hydrogen; $R_3$ is

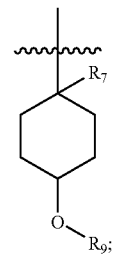

$R_9$ is a member selected from the group consisting of hydrogen, aryl, and heterocycle and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is a member selected from the group consisting of alkyl, cycloalkyl, and heterocycle; $R_3$ is alkyl; wherein the alkyl group of $R_3$ is substituted with a member of the group consisting of alkoxy, alkoxycarbonyl, alkoxycarbonylNH, alkylNH, carboxy, and hydroxy and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ is hydrogen; $R_3$ is alkyl; wherein the alkyl group of $R_3$ is substituted with a member of the group consisting of alkoxy, alkoxycarbonyl, alkoxycarbonylNH, alkylNH, carboxy, and hydroxy; and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is hydrogen; $R_3$ is alkyl; wherein the alkyl group of $R_3$ is substituted with a member of the group consisting of alkoxy, alkoxycarbonyl, alkoxycarbonylNH, alkylNH, carboxy, and hydroxy; and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is selected from the group consisting of alkyl, cycloalkyl, and heterocycle; $R_3$ is a member selected from the group consisting of aryl and heterocycle; wherein said heterocycle is a member selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl and wherein X is as defined in formula (I).

According to a further embodiment of the present invention there is provided a compound of formula (I), wherein R is cyano; $R_1$ is alkynyl, wherein alkynyl is ethynyl or propynyl, $R_2$ is hydrogen; and $R_3$ is a member selected from the group consisting of aryl and heterocycle; wherein said heterocycle is a member selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl; and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is hydrogen; $R_3$ is a member selected from the group consisting of aryl and heterocycle; wherein said heterocycle is a member selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl; and wherein X is as defined in formula (I).

According to a further embodiment of the present invention there is provided a compound of formula (I), wherein R is cyano; $R_1$ is a member selected from the group consisting of alkyl and alkynyl; $R_2$ is hydrogen; $R_3$ is heterocycle; wherein said heterocycle is piperidine, and wherein X is as defined in formula (I).

According to a further embodiment of the present invention there is provided a compound of formula (I), wherein R is cyano; $R_1$ is alkyl, alkenyl, and alkynyl; $R_2$ is a member selected from the group consisting of alkyl, cycloalkyl, and heterocycle; $R_3$ is a member selected from the group consisting of arylalkyl and heterocyclealkyl; and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ is hydrogen; $R_3$ is a member selected from the group consisting of arylalkyl and heterocyclealkyl; and wherein X is as defined in formula (I).

According to a further embodiment of the present invention there is provided a compound of formula (I), wherein R is cyano; $R_1$ is a member selected from the group consisting of alkyl and alkynyl; $R_2$ is a member selected from the group consisting of alkyl, cycloalkyl, and heterocycle; $R_3$ is

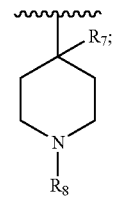

$R_7$ is a member selected from the group consisting of hydrogen and alkyl; $R_8$ is a member selected from the group consisting of hydrogen, alkylcarbonyl, aryl and heterocycle; and wherein X is as defined in formula (I).

According to a further embodiment of the present invention there is provided a compound of formula (I), wherein R is cyano, $R_1$ is alkynyl, wherein alkynyl is ethynyl or propynyl, $R_2$ is hydrogen; $R_3$ is

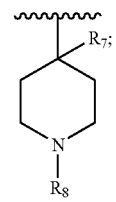

$R_7$ is a member selected from the group consisting of hydrogen and alkyl; $R_8$ is a member selected from the group consisting of hydrogen, alkylcarbonyl, aryl and heterocycle; and wherein X is as defined in formula (I).

According to a further embodiment of the present invention there is provided a compound of formula (I), wherein R is cyano, $R_1$ is a member selected from the group consisting of alkyl and alkynyl; $R_2$ is hydrogen; $R_3$ is

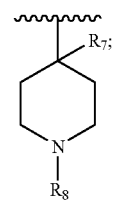

$R_7$ is a member selected from the group consisting of hydrogen and alkyl; $R_8$ is a member selected from the group consisting of arylcarbonyl, and heterocyclecarbonyl-; and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ is hydrogen; $R_3$ is

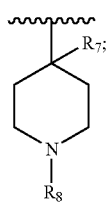

$R_7$ is a member selected from the group consisting of hydrogen and alkyl; $R_8$ is a member selected from the group consisting of arylcarbonyl and heterocyclecarbonyl-; and wherein X is as defined in formula (I).

According to a further embodiment of the present invention there is provided a compound of formula (I), wherein R is cyano; $R_1$ is a member selected from the group consisting of alkyl, alkenyl, and alkynyl; $R_2$ is hydrogen; $R_3$ is heterocycle, wherein said heterocycle is

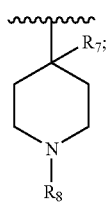

$R_7$ is a member selected from the group consisting of hydrogen and alkyl; $R_8$ is a member selected from the group consisting of aryl, heterocycle; and wherein X is as defined in formula (I). Aryl and heterocycles at the $R_8$ position may be substituted with 0, 1, 2 or 3 substituents independently selected from the group consisting of alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle.

According to a further embodiment of the present invention there is provided a compound of formula (I), wherein R is cyano; $R_1$ is a member selected from the group consisting of alkyl and alkynyl; $R_2$ is hydrogen; $R_3$ is heterocycle, wherein said heterocycle is

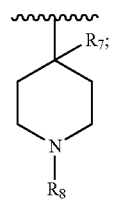

$R_7$ is a member selected from the group consisting of hydrogen and alkyl; $R_8$ is a member selected from the group consisting of arylcarbonyl and heterocyclecarbonyl; and wherein X is as defined in formula (I). The aryl group of the arylcarbonyl group of $R_8$ of the compounds of the present invention may optionally substituted with 0, 1, 2 or 3 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The heterocycle group of heterocyclecarbonyl may be optionally substituted as described above for the aryl group of the arylcarbonyl group.

According to a further embodiment of the present invention there is provided a compound of formula (I), wherein R is cyano; $R_1$ is a member selected from the group consisting of alkyl and alkynyl; $R_2$ is a member selected from the group consisting of alkyl, cycloalkyl, and heterocycle; $R_3$ is a member selected from the group consisting of aryl-O-alkyl, aryl-NH-alkyl, heterocycle-O-alkyl and heterocycle-NH-alkyl; and wherein X is as defined in formula (I).

According to a further embodiment of the present invention there is provided a compound of formula (I), wherein R is cyano, $R_1$ is alkynyl, wherein alkynyl is ethynyl or propynyl, $R_2$ is hydrogen; $R_3$ is a member selected from the group consisting of aryl-O-alkyl, aryl-NH-alkyl, heterocycle-O-alkyl and heterocycle-NH-alkyl; and wherein X is as defined in formula (I).

According to a further embodiment of the present invention there is provided a compound of formula (I), wherein R is cyano; $R_1$ is a member selected from the group consisting of alkyl and alkynyl; $R_2$ and $R_3$ taken together with the atoms they are attached form a mono or bicyclic heterocycle selected from the group consisting of 3-isoquinoline, 2-pyrrolidinyl, 2-quinolinyl, 2-tetrahydroquinolinyl, and 3-tetrahydroisoquinolinyl; and wherein X is as defined in formula (I).

According to a further embodiment of the present invention there is provided a compound of formula (I), wherein R is cyano; $R_1$ is alkynyl, wherein alkynyl is ethynyl or propynyl; $R_2$ and $R_3$ taken together with the atoms they are attached form a mono or bicyclic heterocycle selected from the group consisting of 3-isoquinoline, 2-pyrrolidinyl, 2-quinolinyl, 2-tetrahydroquinolinyl, and 3-tetrahydroisoquinolinyl; and wherein X is as defined in formula (I).

According to a further embodiment of the present invention there is provided a compound of formula (I), wherein R is cyano; $R_1$ is a member selected from the group consisting of alkyl, alkenyl, alkynyl; $R_2$ and $R_3$ taken together with the atoms they are attached form 3-isoquinolinyl, and wherein X is as defined in formula (I).

According to a further embodiment of the present invention there is provided a compound of formula (I), wherein R is cyano; $R_1$ is a member selected from the group consisting of alkyl and alkynyl; $R_2$ is hydrogen; $R_3$ is $R_9$—O-cycloalkyl, wherein said $R_9$—O-cycloalkyl is

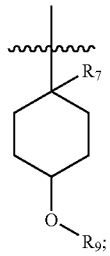

$R_7$ is a member selected from the group consisting of hydrogen and alkyl; $R_9$ is a member selected from the group consisting of hydrogen, aryl, pyridine, and pyrimidine; and wherein X is as defined in formula (I). The aryl group or pyridyl group of $R_9$ may be optionally substituted with 0, 1, 2 or 3 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle.

According to a further embodiment of the present invention there is provided a compound of formula (I), wherein R is cyano; $R_1$ is a member selected from the group consisting of alkyl, alkenyl, alkynyl; $R_2$ is hydrogen; $R_3$ is a member selected from the group consisting of arylalkyl and heterocyclealkyl; and wherein X is as defined in formula (I). The aryl group of arylalkyl of and the heterocycle of heterocyclealkyl of $R_3$ is optionally substituted with 0, 1, 2 or 3 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. In one particular embodiment of the present invention the heterocycle of heterocyclealkyl is pyridine.

According to a further embodiment of the present invention there is provided a compound of formula (I), wherein R is cyano; $R_1$ is a member selected from the group consisting of alkyl and alkynyl; $R_2$ is hydrogen; $R_3$ is a member selected from the group consisting of arylNHalkyl-, aryl-O-alkyl-, heterocycleNHalkyl- and heterocycle-O-alkyl-; and wherein X is as defined in formula (I). The aryl group of arylNHalkyl- and aryl-O-alkyl- and the heterocycle of heterocycleNHalkyl- and heterocycle-O-alkyl- of $R_3$ is optionally substituted with 0, 1, 2 or substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle.

According to a further embodiment of the present invention there is provided a compound of formula (I), wherein R is cyano; $R_1$ is a member selected from the group consisting of alkyl and alkynyl; $R_2$ is hydrogen; $R_3$ is alkyl; and wherein X is as defined in formula (I). In one particular embodiment of the present invention, the alkyl group of $R_3$ is substituted with 0, 1, 2 or 3 substituents independently selected from alkoxy, alkoxyalkyl, alkoxyalkenyl, alkanoyl, alkanoyloxy, alkanoyloxyalkenyl, alkoxycarbonyl, alkoxycarbonylalkenyl, alkylsulfonyl, alkylsulfonylalkenyl, amino, aminoalkenyl, aminosulfonyl, aminosulfonylalkenyl, carboxaldehyde, (carboxaldehyde)alkenyl, carboxamido, carboxamidoalkenyl, carboxy, carboxyalkenyl, cyano, cyanoalkenyl, halo, haloalkenyl, hydroxy, hydroxyalkenyl, nitro, perfluoroalkyl, perfluoroalkoxy, perfluoroalkoxyalkenyl thioalkoxy, thioalkoxyalkenyl, unsubstituted or substituted aryl, unsubstituted or substituted heteroaryl, and unsubstituted or substituted heterocycle.

According to a further embodiment of the present invention there is provided a compound of formula (I), wherein R is cyano; $R_1$ is a member selected from the group consisting of alkyl, alkenyl, and alkynyl; $R_2$ is hydrogen; $R_3$ is a member selected from the group consisting of bicycloalkyl, cycloalkyl, heterocycle and tricycloalkyl; and wherein X is as defined in formula (I). The bicycloalkyl, cycloalkyl, heterocycle or tricycloalkyl of $R_3$ of the present invention may be optionally substituted with 0, 1, 2 or 3 substituents independently selected from alkoxy, alkoxyalkyl, alkoxyalkenyl, alkanoyl, alkanoyloxy, alkanoyloxyalkenyl, alkoxycarbonyl, alkoxycarbonylalkenyl, alkylsulfonyl, alkylsulfonylalkenyl, amino, aminoalkenyl, aminosulfonyl, aminosulfonylalkenyl, carboxaldehyde, (carboxaldehyde)alkenyl, carboxamido, carboxamidoalkenyl, carboxy, carboxyalkenyl, cyano, cyanoalkenyl, halo, haloalkenyl, hydroxy, hydroxyalkenyl, nitro, perfluoroalkyl, perfluoroalkoxy, perfluoroalkoxyalkenyl thioalkoxy, thioalkoxyalkenyl, unsubstituted or substituted aryl, unsubstituted or substituted heteroaryl, and unsubstituted or substituted heterocycle.

Specific compounds of the present invention include, but are not limited to:

(2S,5R)-5-ethynyl-1-L-leucylpyrrolidine-2-carbonitrile;
(2S,5R)-5-ethynyl-1-((3S)-1,2,3,4-tetrahydroisoquinolin-3-ylcarbonyl)pyrrolidine-2-carbonitrile;
(2S,5R)-1-((2S)-2-amino-2-cyclopentylethanoyl)-5-ethynylpyrrolidine-2-carbonitrile;
(2S,5R)-1-((2S)-2-amino-2-cyclopentylethanoyl)-5-vinylpyrrolidine-2-carbonitrile;
(2S,5R)-1-((2S)-2-amino-2-cyclohexylethanoyl)-5-ethynylpyrrolidine-2-carbonitrile;
(2S,5S)-5-ethyl-1-L-leucylpyrrolidine-2-carbonitrile;
(2S,5S)-1-((2S)-2-amino-2-cyclohexylethanoyl)-5-ethylpyrrolidine-2-carbonitrile;
(2S,5R)-1-{N-((1R,2R,4S)-bicyclo(2.2.1)hept-2-yl)glycyl}-5-ethynylpyrrolidine-2-carbonitrile;
(2S,5S)-1-L-leucyl-5-methylpyrrolidine-2-carbonitrile;
(2S,5R)-5-ethynyl-1-(N-(4-methyl-1-pyridin-2-ylpiperidin-4-yl)glycyl)pyrrolidine-2-carbonitrile;
(2S,5R)-5-ethynyl-1-(N-(4-methyl-1-(3-cyano-pyridin-2-yl)piperidin-4-yl)glycyl)pyrrolidine-2-carbonitrile;
(2S,5R)-5-ethynyl-1-(N-(1-(3-cyano-pyridin-3-yl)piperidin-4-yl)glycyl)pyrrolidine-2-carbonitrile;
(2S,5R)-5-ethynyl-1-{N-(4-methyl-1-(4-methoxycarbonyl-benzoyl)piperidin-4-yl)glycyl}pyrrolidine-2-carbonitrile;
(2S,5R)-5-ethynyl-1-{N-(4-methyl-1-(4-carboxy-pyridin-2-yl)piperidin-4-yl)glycyl}pyrrolidine-2-carbonitrile;
(2S,5R)-5-ethynyl-1-(N-{4-methyl-1-(5-(trifluoromethyl)pyridin-2-yl)piperidin-4-yl}glycyl)pyrrolidine-2-carbonitrile;
(2S,5R)-1-{N-(1-(4-chlorobenzoyl)piperidin-4-yl)glycyl}-5-ethynylpyrrolidine-2-carbonitrile;
(2S,5R)-1-{N-(1-(5-chloropyridin-2-yl)-4-methylpiperidin-4-yl)glycyl}-5-ethynylpyrrolidine-2-carbonitrile;
(2S,5R)-5-ethynyl-1-(N-(1-pyridin-2-ylpiperidin-4-yl)glycyl)pyrrolidine-2-carbonitrile;
(2S,5R)-5-ethynyl-1-(N-{4-methyl-1-(4-(trifluoromethyl)pyrimidin-2-yl)piperidin-4-yl}glycyl)pyrrolidine-2-carbonitrile;
(2S,5R)-5-ethynyl-1-(N-(1-isonicotinoyl-4-methylpiperidin-4-yl)glycyl)pyrrolidine-2-carbonitrile;
(2S,5R)-5-ethynyl-1-(N-(4-methyl-1-(5-carboxy-pyridin-2-yl)piperidin-4-yl)glycyl)pyrrolidine-2-carbonitrile;
(2S,5R)-5-ethynyl-1-(N-(4-methyl-1-(5-cyano-pyridin-3-yl)piperidin-4-yl)glycyl)pyrrolidine-2-carbonitrile;
(2S,5R)-5-ethynyl-1-(N-trans(4-hydroxycyclohexyl)glycyl)pyrrolidine-2-carbonitrile;
(2S,5R)-5-ethynyl-1-(N-(4-trans{(4'-fluoro-5-(trifluoromethyl)-1,1'-biphenyl-2-yl)oxy}cyclohexyl)glycyl)pyrrolidine-2-carbonitrile;
(2S,5R)-5-ethynyl-1-(N-{4-trans(4-(trifluoromethoxy)phenoxy)cyclohexyl}glycyl)pyrrolidine-2-carbonitrile;
(2S,5R)-5-ethynyl-1-(N-(4-hydroxy-1-methylcyclohexyl)glycyl)pyrrolidine-2-carbonitrile;
(2S,5R)-5-ethynyl-1-{N-(1-methyl-4-trans(pyridin-3-yloxy)cyclohexyl)glycyl}pyrrolidine-2-carbonitrile;
(2S,5R)-1-(N-{4-trans((5-chloropyridin-3-yl)oxy)cyclohexyl}glycyl)-5-ethynylpyrrolidine-2-carbonitrile;
(2S,5R)-1-{N-(4-trans(4-cyanophenoxy)cyclohexyl)glycyl}-5-ethynylpyrrolidine-2-carbonitrile;
(2S,5R)-5-ethynyl-1-(N-(4-trans{(5-(trifluoromethyl)pyridin-2-yl)oxy}cyclohexyl)glycyl)pyrrolidine-2-carbonitrile;
(2S,5R)-5-ethynyl-1-(N-{4-trans(3-pyridin-4-yl-4-(trifluoromethyl)phenoxy)cyclohexyl}glycyl)pyrrolidine-2-carbonitrile;
(2S,5R)-5-ethynyl-1-{N-(4-trans(pyridin-2-yloxy)cyclohexyl)glycyl}pyrrolidine-2-carbonitrile;
(2S,5R)-5-ethynyl-1-{N-(1-methyl-4-trans(5-cyano-pyridin-2-yloxy)cyclohexyl)glycyl}pyrrolidine-2-carbonitrile;
(2S,5R)-5-ethynyl-1-{N-(4-trans (pyrimidin-2-yloxy)cyclohexyl)glycyl}pyrrolidine-2-carbonitrile;
(2S,5R)-5-ethynyl-1-{N-(4-trans(5-cyano-pyridin-2-yloxy)cyclohexyl)glycyl}pyrrolidine-2-carbonitrile;
(2S,5R)-5-ethynyl-1-(N-{4trans-(4-(trifluoromethyl)phenoxy)cyclohexyl}glycyl)pyrrolidine-2-carbonitrile;
(2S,5R)-5-ethynyl-1-(N-{4-((5-fluoropyridin-3-yl)oxy)-1-methylcyclohexyl}glycyl)pyrrolidine-2-carbonitrile;
(2S,5R)-5-ethynyl-1-(N-(4-trans(4-carboxy-phenoxy)cyclohexyl)glycyl)pyrrolidine-2-carbonitrile;
(2S,5R)-5-ethynyl-1-(N-{4-(2-(2-oxopyrrolidin-1-yl)-4-trans (trifluoromethyl)phenoxy)cyclohexyl}glycyl)pyrrolidine-2-carbonitrile;
(2S,5R)-1-{N-(4-(4-cyano-2-methoxyphenoxy)cyclohexyl)glycyl}-5-ethynylpyrrolidine-2-carbonitrile;
(2S,5R)-1-(N-{4-trans ((5-chloropyridin-2-yl)oxy)cyclohexyl}glycyl)-5-ethynylpyrrolidine-2-carbonitrile;
(2S,5R)-5-ethynyl-1-{N-(1-methyl-4-trans(pyridin-2-yloxy)cyclohexyl)glycyl}pyrrolidine-2-carbonitrile;
(2S,5R)-5-ethynyl-1-(N-{4-trans ((5-fluoropyridin-3-yl)oxy)cyclohexyl}glycyl)pyrrolidine-2-carbonitrile;
(2S,5R)-1-(N-{4-trans ((5-bromopyridin-2-yl)oxy)cyclohexyl}glycyl)-5-ethynylpyrrolidine-2-carbonitrile;
(2S,5R)-5-ethynyl-1-{N-(4-trans(pyridin-3-yloxy)cyclohexyl)glycyl}pyrrolidine-2-carbonitrile;
(2S,5R)-5-ethynyl-1-(N-(1,1,3,3-tetramethylbutyl)glycyl)pyrrolidine-2-carbonitrile;
(2S,5R)-1-{N-(1,1-dimethyl-2-(5-cyano-pyridin-2-yloxy)ethyl)glycyl}-5-ethynylpyrrolidine-2-carbonitrile;
(2S,5R)-1-(N-(tert-butyl)glycyl)-5-ethynylpyrrolidine-2-carbonitrile;
(2S,5R)-1-{N-(1,1-dimethyl-2-(quinolin-4-ylamino)ethyl)glycyl}-5-ethynylpyrrolidine-2-carbonitrile;
(2S,5R)-5-ethynyl-1-{N-(2-(4-fluorophenyl)-1,1-dimethylethyl)glycyl}pyrrolidine-2-carbonitrile;
(2S,5R)-1-(N-(1,1-dimethylpropyl)glycyl)-5-ethynylpyrrolidine-2-carbonitrile;
(2S,5R)-1-{N-(2-(1,3-benzothiazol-2-ylamino)-1,1-dimethylethyl)glycyl}-5-ethynylpyrrolidine-2-carbonitrile;
(2S,5R)-1-{N-((1R,4S)-bicyclo(2.2.1)hept-2-yl)glycyl}-5-ethynylpyrrolidine-2-carbonitrile;
(2S,5R)-5-ethynyl-1-((3S)-1,2,3,4-tetrahydroisoquinolin-3-ylcarbonyl)pyrrolidine-2-carbonitrile;
(2S,5R)-1-(N-1-adamantylglycyl)-5-ethynylpyrrolidine-2-carbonitrile;
(2S,5R)-1-(N-cyclohexylglycyl)-5-ethynylpyrrolidine-2-carbonitrile;
(2S,5R)-5-ethynyl-1-{N-(1-(methoxymethyl)cyclopentyl)glycyl}pyrrolidine-2-carbonitrile;
(2S,5R)-5-ethynyl-1-(N-tetrahydro-2H-pyran-4-ylglycyl)pyrrolidine-2-carbonitrile;
(2S,5R)-5-ethynyl-1-{N-((2S)-2-hydroxycyclopentyl)glycyl}pyrrolidine-2-carbonitrile;
(2S,5R)-1-(N-cyclopentylglycyl)-5-ethynylpyrrolidine-2-carbonitrile;
(2S,5R)-5-ethynyl-1-{N-(1-(hydroxymethyl)cyclopentyl)glycyl}pyrrolidine-2-carbonitrile;
(2S,5R)-5-ethynyl-1-L-leucylpyrrolidine-2-carbonitrile;
(2S,5R)-1-((2S)-2-amino-2-cyclopentylethanoyl)-5-ethynylpyrrolidine-2-carbonitrile;
(2S,5R)-1-((2R)-2-amino-2-cyclohexylethanoyl)-5-ethynylpyrrolidine-2-carbonitrile;

(2S,5S)-1-((2S)-2-amino-2-cyclopentylethanoyl)-5-methylpyrrolidine-2-carbonitrile;
(2S,5R)-1-((2S)-2-amino-2-cyclopentylethanoyl)-5-prop-1-ynylpyrrolidine-2-carbonitrile;
(2S,5R)-5-prop-1-ynyl-1-(N-{4-(4-(trifluoromethyl)phenoxy)cyclohexyl}glycyl)pyrrolidine-2-carbonitrile;
(2S,5R)-1-{N-(1-(hydroxymethyl)cyclopentyl)glycyl}-5-prop-1-ynylpyrrolidine-2-carbonitrile;
(2S,5R)-1-(N-cyclopentylglycyl)-5-prop-1-ynylpyrrolidine-2-carbonitrile;
(2S,5S)-1-(N-cyclopentylglycyl)-5-methylpyrrolidine-2-carbonitrile;
(2S,5S)-4,4-difluoro-5-methyl-1-L-valylpyrrolidine-2-carbonitrile;
(2S,5S)-1-{N-(1-(hydroxymethyl)cyclopentyl)glycyl}-5-methylpyrrolidine-2-carbonitrile;
(2S,5S)-4,4-difluoro-1-L-leucyl-5-methylpyrrolidine-2-carbonitrile;
(2S,5R)-1-((2S)-2-amino-2-cyclohexylethanoyl)-5-vinylpyrrolidine-2-carbonitrile;
(2S,5R)-1-((2R)-2-amino-2-cyclopentylethanoyl)-5-vinylpyrrolidine-2-carbonitrile;
(2S,5S)-1-{N-((2R,5S)-hexahydro-2,5-methanopentalen-3a(1H)-yl)glycyl}-5-methylpyrrolidine-2-carbonitrile;
(2S,5R)-5-ethynyl-1-(N-(1-tert-butoxycarbonyl-piperidin-4-yl)glycyl)pyrrolidine-2-carbonitrile;
(2S,5R)-5-ethynyl-1-(N-(1-5-cyano-pyridin-2-ylpiperidin-4-yl)glycyl)pyrrolidine-2-carbonitrile;
(2S,5R)-1-{N-(1-(4-chlorobenzoyl)-4-methylpiperidin-4-yl)glycyl}-5-ethynylpyrrolidine-2-carbonitrile;
(2S,5R)-1-{N-(1-(3-cyanophenyl)-4-methylpiperidin-4-yl)glycyl}-5-ethynylpyrrolidine-2-carbonitrile;
(2S,5R)-1-{N-(1-(4-cyanobenzoyl)-4-methylpiperidin-4-yl)glycyl}-5-ethynylpyrrolidine-2-carbonitrile;
N-(1-(3-chlorophenyl)-1H-indol-5-yl)-5-methyl-3-phenyl-isoxazole-4-carboxamide;
(2S,5R)-1-{N-(1-(4-bromobenzoyl)-4-methylpiperidin-4-yl)glycyl}-5-ethynylpyrrolidine-2-carbonitrile;
(2S,5R)-5-ethynyl-1-(N-{4-methyl-1-(4-(trifluoromethyl)pyridin-2-yl)piperidin-4-yl}glycyl)pyrrolidine-2-carbonitrile;
(2S,5R)-1-{N-(4-trans4-cyano-2-fluorophenoxy)cyclohexyl)glycyl}-5-ethynylpyrrolidine-2-carbonitrile;
(2S,5R)-5-ethynyl-1-{N-(4-trans3-fluorophenoxy)-1-methylcyclohexyl)glycyl}pyrrolidine-2-carbonitrile;
(2S,5R)-1-{N-(4-trans3-cyanophenoxy)cyclohexyl)glycyl}-5-ethynylpyrrolidine-2-carbonitrile;
(2S,5R)-5-ethynyl-1-(N-(1-methyl-4-{(5-(trifluoromethyl)pyridin-2-yl)oxy}cyclohexyl)glycyl)pyrrolidine-2-carbonitrile;
(2S,5R)-1-(N-{4-trans ((5-chloropyridin-2-yl)oxy)cyclohexyl}glycyl)-5-ethynylpyrrolidine-2-carbonitrile;
(2S,5R)-5-ethynyl-1-(N-(4-trans{(4'-fluoro-2-(trifluoromethyl)-1,1'-biphenyl-4-yl)oxy}cyclohexyl)glycyl)pyrrolidine-2-carbonitrile;
(2S,5R)-5-ethynyl-1-(N-(4-trans{(4'-fluoro-6-(trifluoromethyl)-1,1'-biphenyl-3-yl)oxy}cyclohexyl)glycyl)pyrrolidine-2-carbonitrile;
(2S,5R)-1-(N-{4-(3-cyano-4-trans (trifluoromethyl)phenoxy)cyclohexyl}glycyl)-5-ethynylpyrrolidine-2-carbonitrile;
(2S,5R)-1-{N-(4-trans3-bromophenoxy)cyclohexyl)glycyl}-5-ethynylpyrrolidine-2-carbonitrile;
(2S,5R)-1-{N-(4-trans4-cyano-3-fluorophenoxy)cyclohexyl)glycyl}-5-ethynylpyrrolidine-2-carbonitrile;
(2S,5R)-1-(N-{4-(2-cyano-4-trans (trifluoromethyl)phenoxy)cyclohexyl}glycyl)-5-ethynylpyrrolidine-2-carbonitrile;
(2S,5R)-1-{N-(4-trans3(3-cyanophenoxy)-1-methylcyclohexyl)glycyl}-5-ethynylpyrrolidine-2-carbonitrile;
(2S,5R)-1-{N-(4-trans4-chlorophenoxy)cyclohexyl)glycyl}-5-ethynylpyrrolidine-2-carbonitrile;
(2S,5R)-5-ethynyl-1-(N-(4-trans{(6-methyl-4-(trifluoromethyl)pyridin-2-yl)oxy}cyclohexyl)glycyl)pyrrolidine-2-carbonitrile;
(2S,5R)-1-(N-{4-trans(2-cyano-3-(trifluoromethyl)phenoxy)cyclohexyl}glycyl)-5-ethynylpyrrolidine-2-carbonitrile;
(2S,5R)-5-ethynyl-1-(N-{4-trans(4-pyridin-4-yl-3-(trifluoromethyl)phenoxy)cyclohexyl}glycyl)pyrrolidine-2-carbonitrile;
(2S,5R)-1-(N-{4-(3-cyano-5-(trifluoromethyl)phenoxy)cyclohexyl}glycyl)-5-ethynylpyrrolidine-2-carbonitrile;
(2S,5R)-5-ethynyl-1-{N-(4-(4-fluorophenoxy)-1-methylcyclohexyl)glycyl}pyrrolidine-2-carbonitrile;
(2S,5R)-5-ethynyl-1-{N-(4-(3-fluorophenoxy)-1-methylcyclohexyl)glycyl}pyrrolidine-2-carbonitrile;
(2S,5R)-5-ethynyl-1-(N-(1-methyl-4-{(5-(trifluoromethyl)pyridin-2-yl)oxy}cyclohexyl)glycyl)pyrrolidine-2-carbonitrile;
(2S,5R)-5-ethynyl-1-(N-{4-trans3-(trifluoromethyl)phenoxy)cyclohexyl}glycyl)pyrrolidine-2-carbonitrile;
(2S,5R)-1-(N-{4-trans ((3-bromopyridin-2-yl)oxy)cyclohexyl}glycyl)-5-ethynylpyrrolidine-2-carbonitrile;
(2S,5R)-5-ethynyl-1-(N-(4-trans{(4-(trifluoromethyl)pyridin-2-yl)oxy}cyclohexyl)glycyl)pyrrolidine-2-carbonitrile;
(2S,5R)-1-(N-{4-trans ((5-chloropyridin-2-yl)oxy)-1-methylcyclohexyl}glycyl)-5-ethynylpyrrolidine-2-carbonitrile;
(2S,5R)-1-{N-(4-trans3(3-cyanophenoxy)-1-methylcyclohexyl)glycyl}-5-ethynylpyrrolidine-2-carbonitrile;
(2S,5R)-5-ethynyl-1-(N-{4-(2-carboxy-4-trans (trifluoromethyl)phenoxy)cyclohexyl}glycyl)pyrrolidine-2-carbonitrile;
(2S,5R)-1-{N-(4-trans3(3-chlorophenoxy)cyclohexyl)glycyl}-5-ethynylpyrrolidine-2-carbonitrile;
(2S,5R)-5-ethynyl-1-(N-(1-methyl-4-trans{(5-(trifluoromethyl)pyridin-2-yl)oxy}cyclohexyl)glycyl)pyrrolidine-2-carbonitrile;
(2S,5R)-1-{N-(4-trans(4-bromophenoxy)cyclohexyl)glycyl}-5-ethynylpyrrolidine-2-carbonitrile;
(2S,5R)-1-(N-{1,1-dimethyl-2-((3-cyano-6-methylpyridin-2-yl)amino)ethyl}glycyl)-5-ethynylpyrrolidine-2-carbonitrile;
(2S,5R)-1-(N-(1,1-dimethyl-2-{(5-(trifluoromethyl)pyridin-2-yl)oxy}ethyl)glycyl)-5-ethynylpyrrolidine-2-carbonitrile;
(2S,5R)-1-(N-{1,1-dimethyl-2-((3-cyano-6-methylpyridin-2-yl)oxy)ethyl}glycyl)-5-ethynylpyrrolidine-2-carbonitrile;
(2S,5R)-5-ethynyl-1-(N-(tetrahydrofuran-2-ylmethyl)glycyl)pyrrolidine-2-carbonitrile;
(2S,5R)-5-ethynyl-1-(N-(pyridin-2-ylmethyl)glycyl)pyrrolidine-2-carbonitrile;
(2S,5R)-5-ethynyl-1-(N-(2-pyridin-4-ylethyl)glycyl)pyrrolidine-2-carbonitrile;
(2S,5R)-5-ethynyl-1-{N-((1-tert-butoxycarbonylpiperidin-4-yl)methyl)glycyl}pyrrolidine-2-carbonitrile;
(2S,5R)-5-ethynyl-1-{N-(3-(methylamino)propyl)glycyl}pyrrolidine-2-carbonitrile;

(2S,5R)-1-(N-(4-tert-butoxycarbonylbutyl)glycyl)-5-ethynylpyrrolidine-2-carbonitrile;
(2S,5R)-5-ethynyl-1-(N-(3-hydroxy-2,2-dimethylpropyl)glycyl)pyrrolidine-2-carbonitrile;
(2S,5R)-1-{N-(1,1-dimethyl-2-(3-cyanopyridin-2-ylamino)ethyl)glycyl}-5-ethynylpyrrolidine-2-carbonitrile;
(2S,5R)-1-(N-(1,1-dimethyl-2-{(4-(trifluoromethyl)pyrimidin-2-yl)amino}ethyl)glycyl)-5-ethynylpyrrolidine-2-carbonitrile;
(2S,5R)-1-{N-(1,1-dimethyl-2-(5-methoxycarbonylpyridin-2-ylamino)ethyl)glycyl}-5-ethynylpyrrolidine-2-carbonitrile;
(2S,5R)-1-{N-(2-(2-cyano-5-fluorophenoxy)-1,1-dimethylethyl)glycyl}-5-ethynylpyrrolidine-2-carbonitrile;
(2S,5R)-5-ethynyl-1-(N-(4-iodobenzyl)glycyl)pyrrolidine-2-carbonitrile;
(2S,5R)-5-ethynyl-1-{N-(3-(N-tert-butoxycarbonyl-N-methylamino)propyl)glycyl}pyrrolidine-2-carbonitrile;
(2S,5R)-5-ethynyl-1-(N-(4-carboxybutyl)glycyl)pyrrolidine-2-carbonitrile;
(2S,5R)-1-(N-(2-{(3-chloro-5-(trifluoromethyl)pyridin-2-yl)amino}ethyl)glycyl)-5-ethynylpyrrolidine-2-carbonitrile;
(2S,5R)-5-ethynyl-1-(N-(3-isopropoxypropyl)glycyl)pyrrolidine-2-carbonitrile;
(2S,5R)-1-{N-(1,1-dimethyl-2-(5-cyano-pyridin-2-ylamino)ethyl)glycyl}-5-ethynylpyrrolidine-2-carbonitrile;
(2S,5R)-1-(N-(2-(4-carboxy-anilino)-1,1-dimethylethyl)glycyl)-5-ethynylpyrrolidine-2-carbonitrile;
(2S,5R)-5-ethynyl-1-{N-(1-(1-hydroxy-1-methylethyl)cyclopentyl)glycyl}pyrrolidine-2-carbonitrile;
(2S,5R)-5-ethynyl-1-{N-((2R,5S)-hexahydro-2,5-methanopentalen-3a(1H)-yl)glycyl}pyrrolidine-2-carbonitrile;
(2S,5R)-1-(N-cyclopentylglycyl-(N-methyl 1-aminocyclopentanecarboxy)-5-ethynylpyrrolidine-2-carbonitrile;
(2S,5R)-1-(N-cyclopropylglycyl)-5-ethynylpyrrolidine-2-carbonitrile;
(2S,5R)-5-ethynyl-1-(N-piperidin-4-ylglycyl)pyrrolidine-2-carbonitrile;
(2S,5R)-5-ethynyl-1-{N-((5R,7S)-3-hydroxy-1-adamantyl)glycyl}pyrrolidine-2-carbonitrile;
(2S,5R)-5-ethynyl-1-(N-tetrahydrofuran-3-ylglycyl)pyrrolidine-2-carbonitrile;
(2S,5R)-1-(N-cycloheptylglycyl)-5-ethynylpyrrolidine-2-carbonitrile;
(2S,5R)-1-(N-cyclobutylglycyl)-5-ethynylpyrrolidine-2-carbonitrile;
(2S,5R)-5-ethynyl-1-(3-methyl-L-valyl)pyrrolidine-2-carbonitrile;
(2S,5R)-5-ethynyl-1-(3-pyridin-4-yl-L-alanyl)pyrrolidine-2-carbonitrile;
(2S,5R)-1-L-leucyl-5-prop-1-ynylpyrrolidine-2-carbonitrile;
(2S,5R)-1-(3-methyl-L-valyl)-5-prop-1-ynylpyrrolidine-2-carbonitrile;
(2S,5R)-1-(N-cyclobutylglycyl)-5-prop-1-ynylpyrrolidine-2-carbonitrile;
(2S,5R)-1-(N-(4-trans hydroxycyclohexyl)glycyl)-5-prop-1-ynylpyrrolidine-2-carbonitrile;
(2S,5R)-1-{N-((2S)-2-hydroxycyclopentyl)glycyl}-5-prop-1-ynylpyrrolidine-2-carbonitrile;
(2S,5S)-5-methyl-1-{N-((1S,2S,3S,5R)-2,6,6-trimethylbicyclo(3.1.1)hept-3-yl)glycyl}pyrrolidine-2-carbonitrile;
(2S,5S)-1-{N-((5R,7S)-3-hydroxy-1-adamantyl)glycyl}-5-methylpyrrolidine-2-carbonitrile;
(2S,5S)-1-{N-(2-(3,4-dimethoxyphenyl)ethyl)glycyl}-5-methylpyrrolidine-2-carbonitrile;

(2S,5S)-4,4-difluoro-5-methyl-1-((5S)-5-methyl-L-prolyl)pyrrolidine-2-carbonitrile;
(2S,5S)-1-(N-isopropylglycyl)-5-methylpyrrolidine-2-carbonitrile;
(2S,5S)-1-L-isoleucyl-5-methylpyrrolidine-2-carbonitrile;
(2S,5S)-5-methyl-1-{N-(2-(5-cyano-pyridin-2-ylamino)ethyl)glycyl}pyrrolidine-2-carbonitrile;
(2S,5S)-5-methyl-1-((3S)-1,2,3,4-tetrahydroisoquinolin-3-ylcarbonyl)pyrrolidine-2-carbonitrile;
(2S,5S)-1-(3-cyclopropyl-L-alanyl)-5-methylpyrrolidine-2-carbonitrile;
(2S,5S)-5-methyl-1-D-prolylpyrrolidine-2-carbonitrile;
(2S,5S)-1-(N-2,3-dihydro-1H-inden-1-ylglycyl)-5-methylpyrrolidine-2-carbonitrile;
(2S,5S)-5-methyl-1-L-valylpyrrolidine-2-carbonitrile;
(2S,5S)-5-methyl-1-(4-methyl-L-leucyl)pyrrolidine-2-carbonitrile;
(2S,5S)-1-(N-(4-trans hydroxycyclohexyl)glycyl)-5-methylpyrrolidine-2-carbonitrile;
(2S,5S)-1-(N-(tert-butyl)glycyl)-5-methylpyrrolidine-2-carbonitrile;
(2S,5S)-5-methyl-1-((5S)-5-methyl-L-prolyl)pyrrolidine-2-carbonitrile;
(2S,5S)-1-(3-cyclohexyl-L-alanyl)-5-methylpyrrolidine-2-carbonitrile;
6-{[4-({2-[(2S,5R)-2-cyano-5-ethynylpyrrolidin-1-yl]-2-oxoethyl}amino)-4-methylcyclohexyl]oxy}-N,N-dimethylnicotinamide;
(1S,3R)-3-({2-[(2S,5R)-2-cyano-5-ethynylpyrrolidin-1-yl]-2-oxoethyl}amino)-N-(pyridin-2-ylmethyl)cyclopentanecarboxamide;
(1S,3R)-3-({2-[(2S,5R)-2-cyano-5-ethynylpyrrolidin-1-yl]-2-oxoethyl}amino)-N-quinolin-2-ylcyclopentanecarboxamide;
(2S,5R)-5-ethynyl-1-({[4-methyl-1-(5-nitropyridin-2-yl)piperidin-4-yl]amino}acetyl)pyrrolidine-2-carbonitrile;
(2S,5R)-5-ethynyl-1-[({4-methyl-1-[5-(methylsulfonyl)pyridin-2-yl]piperidin-4-yl}amino)acetyl]pyrrolidine-2-carbonitrile;
methyl (1S,3R)-3-({2-[(2S,5R)-2-cyano-5-ethynylpyrrolidin-1-yl]-2-oxoethyl}amino)cyclopentanecarboxylate; and
(2R,5S)-1-[(tert-butylamino)acetyl]pyrrolidine-2,5-dicarbonitrile.

The present compounds can exist as therapeutically acceptable salts. The term "therapeutically acceptable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically acceptable salts formed at the nitrogen of formula (I) to which $R_3$ is attached.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically acceptable excipients. The term "therapeutically acceptable excipient," as used herein, represents a non-toxic, solid, semi-solid or liquid filler, diluent, encapsulating material, or formulation auxiliary of any type. Examples of therapeutically acceptable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally acceptable diluents, dispersing, wetting, or suspending agents. These injectable preparations can be sterilized by filtration through a bacterial-retaining filter or formulated with sterilizing agents that dissolve or disperse in the injectable media.

Inhibition of DPP-IV by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically acceptable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) to effectively ameliorate disorders by inhibiting DPP-IV at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DPP-IV in single or divided doses can be in amounts, for example, from about 0.01 mg/kg/day to about 50 mg/kg/day body weight. In a more preferred range, compounds of the present invention inhibit the action of DPP-IV in a single or divided doses from about 0.1 mg/kg/day to about 25 mg/kg/day body weight. Single dose compositions can contain such amounts or multiple doses thereof of the compounds of the present invention to make up the daily dose. In general, treatment regimens comprise administration to a patient in need of such treatment from about 10 mg to about 1000 mg of the compounds per day in single or multiple doses.

Biological Data

Isolation of Rat DPP-IV

DPP-IV was purified to homogeneity (electrophoretic) from rat kidney as described in *Arch. Biochem. Biophy.* 1995, 323, 148-154. Rat kidney (120 g) was homogenized in 4 volumes of water and the homogenate centrifuged for 15 minutes at 1000 g. The pH of the supernatant was adjusted to 3.9 with 1M HCl and the enzyme solubilized by autolysis for 18 hours at 37° C. The pH of the supernatant collected after centrifugation was adjusted to 7.2 with 1M Trizma base and the enzyme was precipitated with $(NH_4)_2SO_4$ at 90% saturation (662 g solid ammonium sulfate per liter of solution). The solubilized precipitate was chromatographed on Sephadex G-200 (1 m×5 cm) equilibrated with a 10 mM Tris-HCl buffer pH 7.5 containing NaCl at a final concentration of 0.1 M and developed from the bottom. Fractions containing enzymatic activity were pooled, chromatographed on DE-52 (16×2.5 cm) equilibrated with 10 mM Tris-HCl, pH 7.5, and eluted with a 250-mL linear 0-0.4 MNaCl gradient prepared in 10 mM Tris-HCl. DPP-IV was then resolved from other brush border peptidases by chromatography on a phenyl Sepharose column (12×2 cm) equilibrated with 25% $(NH_4)_2 SO_4$ at saturation (144 g ammonium sulfate per liter of 0.05 M Tris-HCl, pH 7.5). The enzyme was eluted in a homogeneous form with a 200-mL linear gradient of 25-0% $(NH_4)_2SO_4$, prepared in 0.05 M Tris HCl buffer.

Human DPP-IV

Caco-2 cells were obtained from American Type Culture Collection (P.O. Box 3605, Manassas, Va.), cultured and maintained at 37° C. with 5% $CO_2$ in low glucose DMEM media supplemented with 10% Fetal Bovine Serum and antibiotic/antimycotic. In preparation for making an extract, cells were seeded at a density to achieve confluence within 7 days. The cells were cultured for an additional 14 days to allow for maximal DPPIV expression. On the day of harvest, cells were washed once with Dulbecco's PBS and solubilized in a 10 mM NaCl containing 50 mM Tris HCl, 0.5% Nonidet P40 and 0.3 ug/ml aprotinin a pH 8.0. The extract was clarified by centrifugation at 35,000 g for 30 minutes at 4° C.

Inhibition Constant Determination for DPP-IV

DPP-IV activity was determined by measuring the rate of hydrolysis of a surrogate substrate Gly-Pro-7-amido-methylcoumarin (Gly-Pro-AMC, Catalogue #G-2761, Sigma, St. Louis, Mo.). The assay is carried out at room temperature in black 96 well polypropylene or 32 compounds are made in DMSO and then diluted ten fold into water. 10 µL of 5 concentrations of the compound of formula (I) (inhibitor) or 10% DMSO in water are added to individual wells containing 80 µL of DPP-IV diluted in assay buffer containing 25 mM HEPES (pH 7.5), 150 mM NaCl and 0.12 mg/mL BSA. After 10 minutes at room temperature, the reaction is initiated by adding 10 µL of either 280, 700, 1750, or 3500 µM Gly-Pro-AMC in water. The DPP-IV activity results in the formation of the fluorescent product amido-methylcoumarin (AMC) which is continuously monitored by excitation at 350 nm and measurement of fluorescent emission at 460 nm every 112 seconds for 37 minutes using an appropriate plate reader. The fluorescence at 460 nm is converted to nanomoles of AMC using a standard curve and the initial rate of AMC formation is calculated. For each concentration of compound of formula (I) (inhibitor) or DMSO control, the initial rates are used to fit the rectangular hyperbola of Michaelis-Menten by non-linear regression analysis (GraphPad Software Prism 3.0). The ratio of the apparent Km/Vmax vs inhibitor concentration is plotted and the competitive Ki is calculated by linear regression to be the negative x-intercept. The uncompetitive Ki is similarly calculated from the x-intercept of the plot of the reciprocal of the apparent Vmax versus the inhibitor concentration (Cornish-Bowden, A. 1995. Fundamentals of Enzyme Kinetics. Revised edition. Portland Press, Ltd., London, U.K.).

The compounds of the present invention were found to inhibit DPP-IV induced fluorescence with inhibitory constants in a range of about 0.014 µM to about 7 µM. In a preferred range, the compounds of the present invention inhibited DPP-IV induced fluorescence with inhibitory constants in a range of about of about 0.014 µM to about 1 µM; and in a more preferred range, the compounds of the present invention inhibited DPP-IV induced fluorescence with inhibitory constants in a range of about of about 0.014 µM to about 0.5 µM.

As inhibitors of DPP-IV action, the compounds of the present invention are useful in treating disorders that are mediated by DPP-IV. Disorders that are mediated by DPP-IV include diabetes, type II diabetes, hyperglycemia, Syndrome X, hyperinsulinemia and obesity. Therefore the compounds of the present invention are useful in treating the disorder of diabetes, type II diabetes, hyperglycemia, Syndrome X, hyperinsulinemia and obesity.

Dipeptidyl-peptidase IV (DPP-IV, EC 3.4.14.5; CD26) is a post-proline cleaving serine protease with significant homology to other alpha-beta hydroxylases (e.g. prolyl oligopeptidase). DPP-IV is found throughout the body, both circulating in plasma and as a type II membrane protein produced by a variety of tissues, including kidney, liver and intestine. DPP-IV plays a role in the cleavage of specific substrates with accessible amino-terminal Xaa-Pro- or Xaa-Ala-dipeptide sequences, resulting in their inactivation or alteration in their biological activities. Important DPP-IV substrates include growth hormone releasing hormone, glucagon-like peptides or (GLP)-1 and 2, gastric inhibitory polypeptide (GIP) and certain chemokines like RANTES (regulated on activation, normal T cell expressed and secreted), stromal cell-derived factor, eotaxin, and macrophage-derived chemokine (Mentlein, R. *Regulatory Peptides,* 1999, 85, 9-24).

The DPP-IV substrate, glucagon-like peptide (GLP)-1, is released from L cells in the distal small intestine and colon after oral ingestion of nutrients. The active GLP-1 (7-36) amide is an incretin that increases glucose stimulated insulin secretion (Drucker, D. J. *Diabetes,* 1998, 47, 159-169). Other activities attributed to GLP-1 (7-36) amide include stimulation of insulin gene expression, trophic effects on pancreatic beta cells, inhibition of glucagon secretion, promotion of satiety, inhibition of food intake, and slowing of gastric emptying (Drucker, D. J. *Diabetes,* 1998, 47, 159-169). These effects of GLP-1 (7-36) amide contribute to glucose homeostasis and the normalization of blood glucose levels in conditions of impaired glucose tolerance. In this regard, GLP-1 (7-36) amide has been demonstrated to reduce postprandial and fasting glycemia in patients with insulin-dependent and non-insulin-dependent diabetes mellitus (Nauck, et al., *Hormone Metab. Res.* 2002, 29, 411-416; Gutniak et al., *J. Internal Medicine,* 2001, 250, 81-87; Rauchman, et al., *Diabetologia.* 1997, 40, 205-11; Ahren, B. *BioEssays* 1998, 20, 642-51). GLP-1 based therapy has therapeutic potential for the treatment of type 2 diabetes. However, active GLP-1 (7-36)

amide is rapidly converted to GLP-1 (9-36) amide by DPP-IV cleavage of the amino-terminal His-Ala-dipeptide of GLP-1 (7-36) amide (Mentlein, et al., *Eur. J. Biochem.* 1993, 214, 829-835). The resulting GLP-1 (9-36) amide is inactive and is an antagonist of the GLP-1 receptor (Knudson, et al., *Eur. J. Pharmacol.* 1996, 318, 429-35). The short half-life of GLP-1 (7-36) amide in the circulation (1-1.5 minutes) makes it impractical as a therapeutic agent and has led to the development of alternative strategies to enhance the anti-diabetogenic activity of GLP-1. One strategy is to increase the circulating half-life of GLP-1, by inhibiting DPP-IV activity (Deacon, et al., *Diabetes.* 1995, 44 1126-31). Inhibition of DPP-IV in vivo increases the level of circulating GLP-1 (7-36) amide with a concomitant increase in its insulinotropic effect (Deacon, et al., *Diabetes.* 1998, 47, 764-9). A DPP-IV inhibitor has been demonstrated to improve glucose tolerance in non-insulin-dependent diabetes mellitus (Ahren, B., et al., *Diabetes Care* 2002, 25, 869-875). Therefore, the compounds of the present invention, including but not limited to those specified in the examples can be used in the treatment of conditions caused by or associated with impaired glucose tolerance including the prevention or treatment of diabetes, especially non-insulin-dependent diabetes mellitus, hyperglycemia, hyperinsulinemia and metabolic syndrome (Johannsson, et al., *J. Endocrinol. Invest.* 1999, 22(5 Suppl), 41-6).

Striking similarities exist between the metabolic syndrome (Syndrome X) and untreated growth hormone deficiency. Abdominal/visceral obesity and insulin resistance characterize both syndromes (Reaven, G M, *Physiol. Rev.* 1995, 75, 473-86; Johansson, et al., *Metabolism.* 1995, 44, 1126-29). Growth hormone favorably effects some of the perturbations associated with abdominal/visceral obesity, including reduction in abdominal/visceral obesity, improved insulin sensitivity and lipoprotein metabolism and reduction in diastolic blood pressure (Barreto-Filho, et al., *J. Clin. Endocrinol. Metab.* 2002, 87(5), 2018-23; Colao et al., *J. Clin. Endocrinol. Metab.* 2002, 87(3), 1088-93; Gotherstrom, et al., *J Clin Endocrinol Metab.* 2001, 86(10), 4657-65; Johannsson, et al.,*J. Endocrinol. Invest.* 1999, 22(5 Suppl), 41-6; Johannsson, et al., *J. Clin. Endocrinol. Metab.* 1997, 82(3), 727-34).

For the treatment of diabetes or Syndrome X, compounds of the present invention may be used alone, or in combination with any existing anti-diabetic agent. Agents which may be used in combination with the compounds of the present invention include, but are not limited to insulin, an insulin analog such as mecasermin and the like, an insulin secretagogue such as nateglinide and the like, a biguanide such as metformin and the like, a sulfonylurea such as chlorpropamide, glipizide, glyburide, and the like, an insulin sensitizing agent such as a PPARγ agonist such as troglitazone, pioglitazone, rosiglitazone, and the like, an α-glucosidase inhibitor such as acarbose, voglibose, miglitol and the like, an aldose reductase inhibitor such as zopolrestat and the like, a metiglinide such as repaglinide and the like, a glycogen phosphorylase inhibitor, GLP-1 or a mimetic of GLP-1 such as exendin-4, or other such anti-diabetic agents that are known to one skilled in the art. The ability of the compounds of the present invention to treat diabetes, alone or in combination with another agent, can be demonstrated according to the methods described by Zander, M.; Mustafa, T.; Toft-Nielsen, M.-B.; Madsbad, S.; Holst, J. J. in *Diabetes Care* 2001, 24, 720-725; or, according to the methods described herein.

DPP-IV-mediated proteolysis has been established as a major route of growth hormone releasing hormone (GHRH) degradation and inactivation (Kubiak, et al., *Drug Metab. Dispos.* 1989, 17, 393-7). GHRH-derivatives that are resistant to DPP-IV cleavage are more potent in increasing serum growth hormone levels when administered i.v. due to longer stability in vivo. DPP-IV inhibition would be predicted to increase GHRH levels and thus serum growth hormone levels. Therefore, the compounds of the present invention, including but not limited to those specified in the examples can be used in the treatment of conditions associated with deficiency in growth hormone including metabolic disorders (central obesity, dyslipidemia), osteoporosis and frailty of aging.

Diabetic dyslipidemia is characterized by multiple lipoprotein defects including moderately high serum levels of cholesterol and triglycerides, small LDL particles and low levels of HDL cholesterol. The dyslipidemia associated with non-insulin-dependent diabetes mellitus is improved in conjunction with improved diabetic condition following treatment with GLP-1 (Junti-Berggren, et al., *Diabetes Care.* 1996, 19, 1200-6). DPP-IV inhibition is predicted to increase the level of circulating GLP-1 (7-36) amide and thereby would be effective in the treatment of diabetic dyslipidemia and associated complications. Therefore, the compounds of the present invention, including but not limited to those specified in the examples can be used in the treatment hypercholesterolemia, hypertriglyceridemia and associated cardiovascular disease.

Parenteral injection of GLP-1 (7-36) amide in healthy men, obese men or patients with non-insulin-dependent diabetes mellitus has been reported to promote satiety and to suppress food intake (Flint, et al., *J. Clin. Invest.* 1998, 101, 515-520; Naslund, et al., *Am. J. Clin. Nutr.* 1998, 68, 525-530; Gutzwiller, et al., *Am. J. Physiol.* 1999, 276, R1541-R1544. DPP-IV inhibition is predicted to increase the level of circulating GLP-1 (7-36) amide and thereby increases satiety in obesity and non-insulin-dependent diabetes mellitus. Therefore, the compounds of the present invention, including but not limited to those specified in the examples can be used in the treatment of obesity.

For the treatment of obesity, compounds of the present invention may be used alone, or in combination with any existing anti-obesity agent as described by Flint, A.; Raben, A.; Astrup, A.; Holst, J. J. in *J. Clin. Invest.* 1998, 101, 515-520 or by Toft-Nielsen, M.-B.; Madsbad, S.; Holst, J. J. in *Diabetes Care* 1999, 22, 1137-1143. Agents which may be used in combination with the compounds of the present invention include, but are not limited to fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, thyromimetic agents, or other such anti-obesity agents that are known to one skilled in the art.

DPP-IV is expressed on a fraction of resting T cells at low density but is strongly upregulated following T-cell activation. DPP-IV may have important functions on T cells and in the immune system. Synthetic inhibitors of the enzymatic activity of CD26 have been shown to suppress certain immune reactions in vitro and in vivo. In vitro recombinant soluble DPP-IV enhances proliferative responses of peripheral blood lymphocytes to stimulation with soluble tetanus toxoid antigen. In addition, the enhancing effect requires DPP-IV enzyme activity (Tanaka, et al., *Proc. Natl. Acad. Sci. USA,* 1994, 91, 3082-86; Tanaka, et al., *Proc. Natl. Acad. Sci. USA* 1993, 90, 4583). Soluble DPP-IV up-regulates the expression of the costimulatory molecule CD86 on monocytes through its dipeptidyl peptidase IV activity suggesting that soluble DPP-IV enhances T cell immune response to recall antigen via its direct effect on antigen presenting cells (Ohnuma, et al., *J. Immunol.* 2001, 167(12), 6745-55). Consequently, DPP-IV inhibition would be predicted to suppress certain immune responses and thus have therapeutic benefit in the treatment of immunomodulatory diseases. Therefore, the compounds of the present invention, including but not limited to those specified in the examples can be used in the treatment of rheumatoid arthritis, multiple sclerosis, scleraderma, chronic inflammatory bowel disease or syndrome and allograft rejection in transplantation.

Chemokine receptors, especially CCR5 and CXCR4, act as cofactors for HIV-1 entry into CD4+ cells and their corresponding ligands can suppress HIV entry and thus replication. The CXC chemokine, stromal cell derived factor-1 (SDF-1) is a chemokine for resting T-lymphocytes and monocytes. SDF-1 exists as two splice variants, SDF-1alpha and SDF-1beta that differ by four additional C-terminal residues in SDF-1beta. Truncation of the N-terminal Lys-Pro-residues from both SDF-1 alpha and SDF-1 beta results in the loss of their chemotactic and antiviral activities in vitro (Ohtsuki, et al, *FEBS Lett.* 1998, 431, 236-40; Shioda, et al., *Proc. Natl. Acad. Sci. USA* 1998 95(11), 6331-6; Proost, et al., *FEBS Lett.* 1998, 432, 73-6). DPP-IV inactivates SDF-1 alpha as a ligand for CXCR4 that is a T cell chemotactic receptor as well as the major co-receptor for T-tropic HIV-1 strains. DPP-IV inhibition would be predicted to increase full-length SDF-1 levels and thereby suppress HIV-1 entry into CXCR4+ cells. Therefore, the compounds of the present invention, including but not limited to those specified in the examples can be used in the treatment of HIV infection (AIDS).

Synthetic Methods

The compounds and processes of the present invention will be better understood in connection with the following synthetic schemes which together illustrate the methods by which the compounds of the invention may be prepared. Starting materials can be obtained from commercial sources or prepared by well-established literature methods known to those of ordinary skill in the art. The synthesis of compounds of formula (I), wherein the groups R, $R_1$, $R_2$ and $R_3$ are as defined above unless otherwise noted below, are exemplified below.

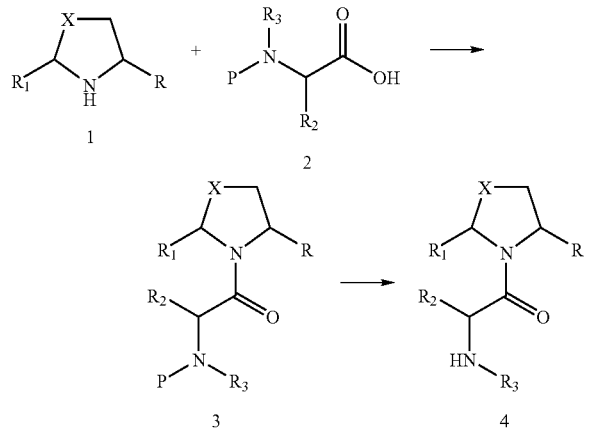

As shown in Scheme 1, compounds of formula 1, which may either be purchased directly or modified from commercially available starting material through methods commonly known to those skilled in the art, may be reacted with compounds of formula 2 (wherein P is a nitrogen protecting group such as but not limited to tert-butyloxycarbonyl, benzyloxycarbonyl and acetyl) along with reagents such as but not limited to 1-(3-(dimethylamino)propyl)-3-ethylcarbodiimide hydrochloride (EDCI) or 2-(1H-benzotriazol-1yl)-1,1,3,3-tetramethyluronium tetrafluoroborate (TBTU) and 4-dimethylaminopyridine (DMAP) in the presence of a base such as but not limited to N-methylmorpholine or diisopropylethylamine in solvents such as but not limited to dichloromethane to provide compounds of formula 3. Compounds of formula 3 may be reacted with reagents known to deprotect the nitrogen protecting group as known to those skilled in the art or demonstrated in Greene, T. W. and Wuts, G. M. "Protective groups in Organic Synthesis", third ed. John Wiley & Sons, 1999, to provide compounds of formula 4, which are representative of compounds of formula (I).

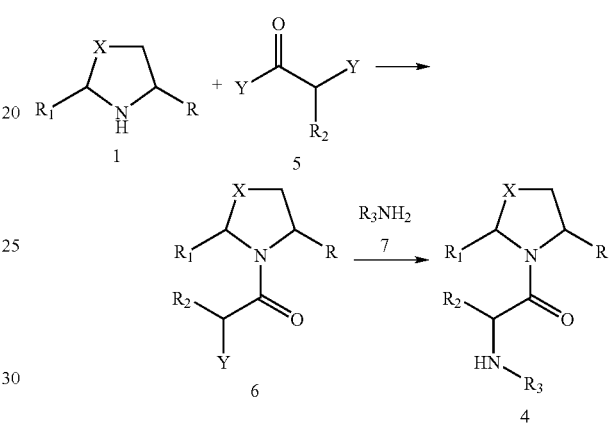

Alternatively, compounds of formula 4 which are representative of compounds of formula (I) can also be synthesized as described in Scheme 2. Compounds of formula 1 can be reacted with compounds of formula 5 (where Y is either bromine or chlorine) in the presence of a base such as, but not limited to, triethylamine or diisopropylethylamine in solvents such as but not limited to THF to provide compounds of formula 6. Compounds of formula 6 can be reacted with amines of formula 7 in solvents such as, but not limited to, acetonitrile to provide compounds of formula 4.

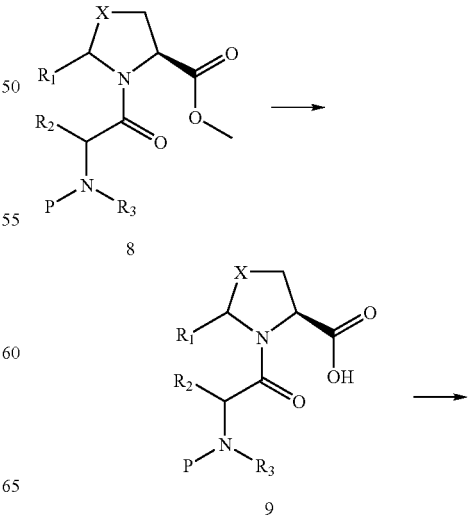

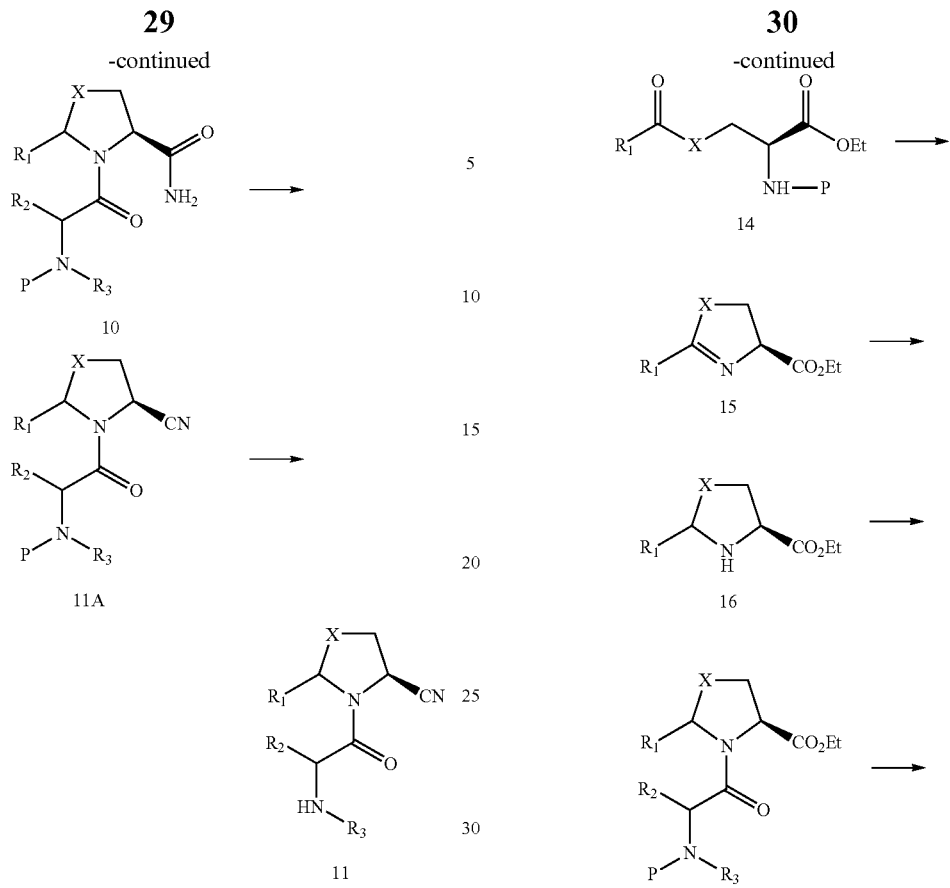

As shown in Scheme 3, compounds of formula 8 which are representative of compounds of formula (I) wherein R is alkoxycarbonyl can be modified through techniques known to those skilled in the art to provide compounds of formula 11 which are representative of compounds of formula (I) wherein R is cyano. Compounds of formula 8 may be reacted with reagents which will effect a hydrolysis of an alkoxycarbonyl group such as, but not limited to, lithium hydroxide or sodium hydroxide in aqueous alcoholic solvents such as but not limited to aqueous methanol or aqueous ethanol to provide of formula 9. Compounds of formula 9 can be reacted with isobutylchloroformate, a base such as N-methylmorpholine in THF at −15° C. for 20 minutes followed by the addition of ammonia in dioxane to provide compounds of formula 10. Compounds of formula 10 can then be reacted with phosphorous oxychloride, pyridine and imidazole at −35° C. or with trifluoroacetic anhydride at 0° C. in a mixture of THF and DMF (1:1) to provide compounds of formula 11A. The nitrogen protecting group of compounds of formula 11A can be removed using conditions known to those skilled in the art to provide compounds of formula 11.

Scheme 4

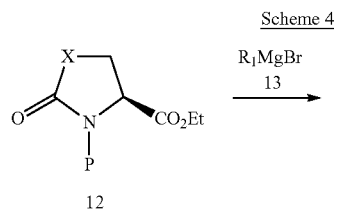

As shown in Scheme 4, compounds of formula 12 (wherein P is a nitrogen protecting group as previously described) can be reacted with organometallic reagents such as but not limited to 13 in solvents such as but not limited to THF at temperatures between −20° C. and −40° C. to provide compounds of formula 14. Compounds of formula 14 can be converted to compounds of formula 15 through the deprotection of the amine protecting group using methods known to those skilled in the art. Compounds of formula 15 can be reduced by hydrogenolysis using 50-60 psi of hydrogen gas and palladium on carbon in solvents such as but not limited to ethanol, methanol, or ethyl acetate or with a hydride source such as sodium borohydride to provide compounds of formula 16. Compounds of formula 16 can be reacted according to the reaction conditions outlined in Scheme 1 or Scheme 2 to provide compounds of formula 8. Compounds of formula 8 can be reacted according to the reaction conditions outlined in Scheme 3 to provide compounds of formula 11 which are representative of compounds of formula (I).

Scheme 5

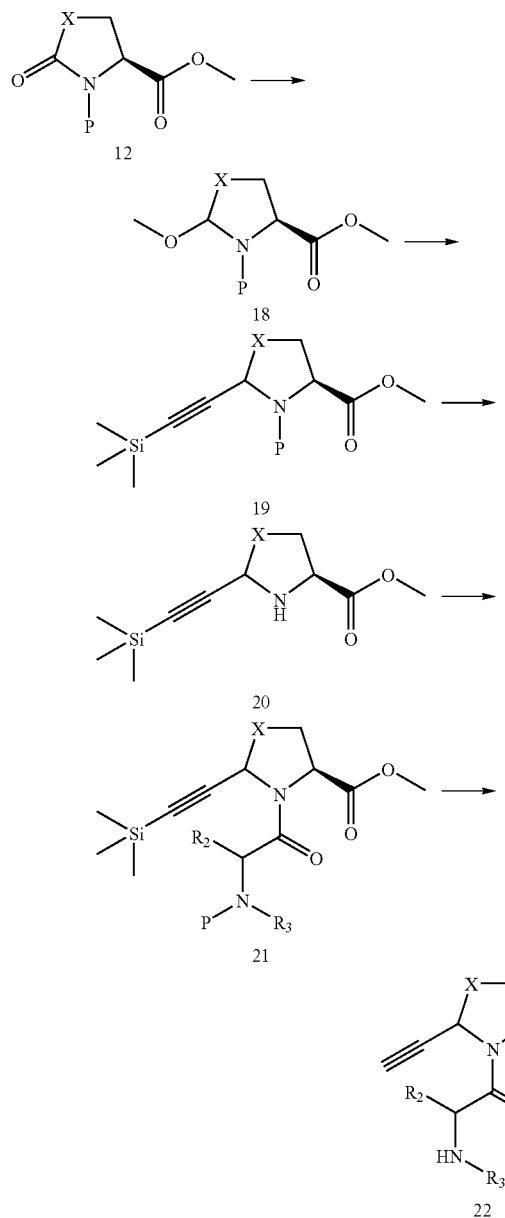

Scheme 6

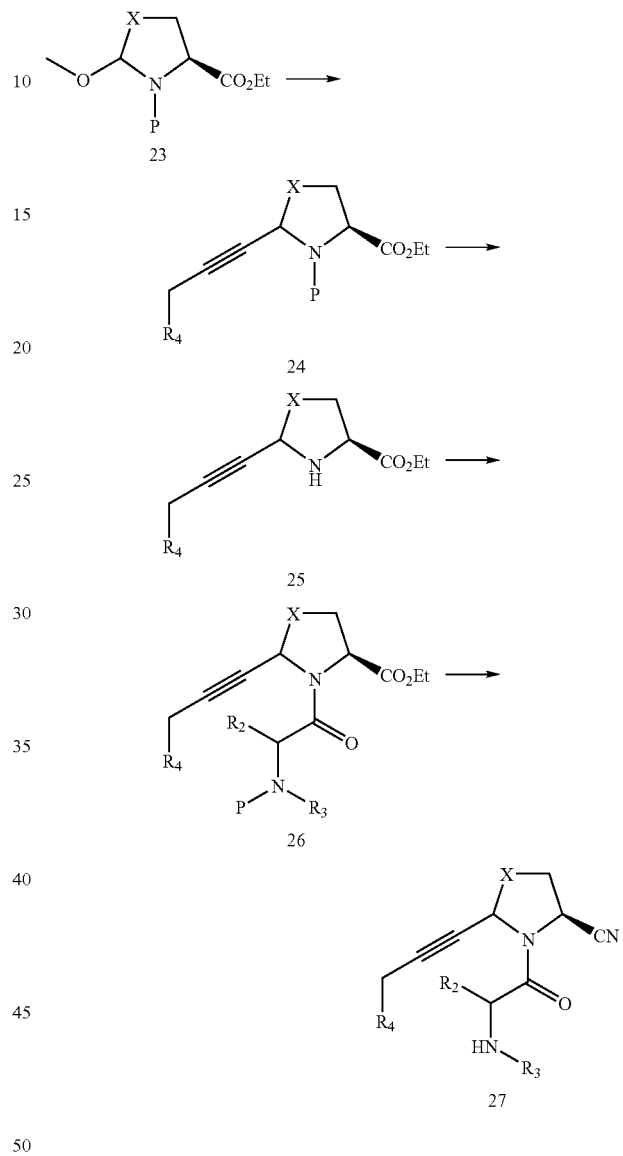

As shown in Scheme 5, compounds of formula 12 can be treated with reducing reagents such as lithium triethylborohydride in THF at ±78° C. to selectively reduce the carbonyl functional group to the alcohol which can then be converted to the methyl ether upon treatment with para-toluensulfonic acid in methanol to provide compounds of formula 18. Compounds of formula 18 can be reacted with bis-trimethylsilylacetylene, tin(IV) chloride and AlCl$_3$, in solvents such as but not limited to dichloromethane to provide compounds of formula 19. Compounds of formula 19 can be converted to compounds of formula 20 using conditions known to those skilled in the art that will deprotect the amine protecting group as previously mentioned in Scheme 1. Compounds of formula 20 can be reacted according to the conditions outlined in Scheme 1 or Scheme 2 to provide compounds of formula 21 which can be further reacted according to the conditions outlined in Scheme 3 to provide compounds of formula 22 which are representative of compounds of formula (I).

As shown in Scheme 6, compounds of formula 23 can be reacted with other acetylene compounds under conditions described in Scheme 5 to provide compounds of formula 24 wherein R$_4$ is a member selected from the group consisting of alkoxy, alkoxyalkyl, alkoxycarbonyl, alkoxycarbonylalkyl, alkylcarbonyl, alkylcarbonylalkyl, heterocycle, and heterocyclealkyl. Compounds of formula 24 can be treated under conditions known to deprotect nitrogen protecting groups as known to those skilled in the art or are described in Scheme 1 or Scheme 2 to provide compounds of formula 25. Compounds of formula 25 can be subjected to conditions outlined in Scheme 1 and 2 provide compounds of formula 26. Compounds of formula 26 can be subjected to conditions outlined in Scheme 3 to convert the ethyl ester to the corresponding nitrile providing compounds of formula 27 which are representative of compounds of formula (I).

Scheme 7

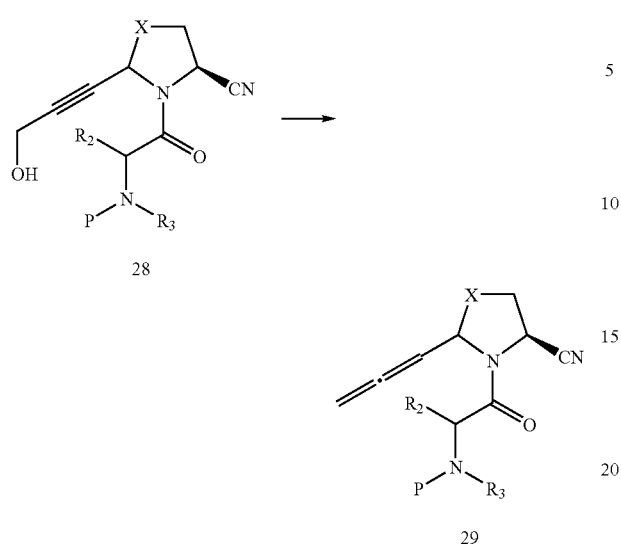

As shown in Scheme 7, compounds of formula 28 may be converted to compounds of formula 29 which are representative of compounds of formula (I). The alcohol functionality of 28 can be reacted with diethyl azodicarboxylate and triphenylphosphine in THF followed by ortho-nitrobenzenesulfonylhydrazine to provide compounds of formula 29. The protecting group of compound of formula 29 can be removed under conditions known to those skilled in the art.

Scheme 8

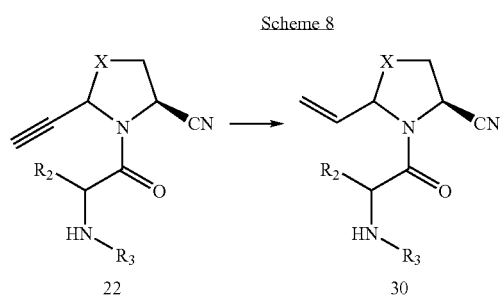

As shown in Scheme 8, compounds of formula 22 can be converted to compounds of formula 30 which are representative of compounds of formula (I) under an atmosphere of hydrogen in the presence of a catalyst such as but not limited to palladium on barium sulfate poisoned with quinoline in a solvent such as but not limited to methanol or ethyl acetate.

Scheme 9

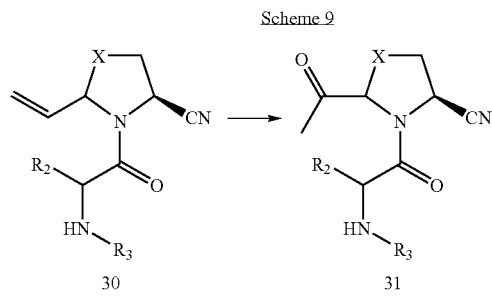

As shown in Scheme 9, compounds of formula 30 can be converted to compounds of formula 31 which are representative of compounds of formula (I) under an atmosphere of oxygen in the presence of a catalyst of palladium chloride in solvents such as but not limited to THF or dioxane.

Scheme 10

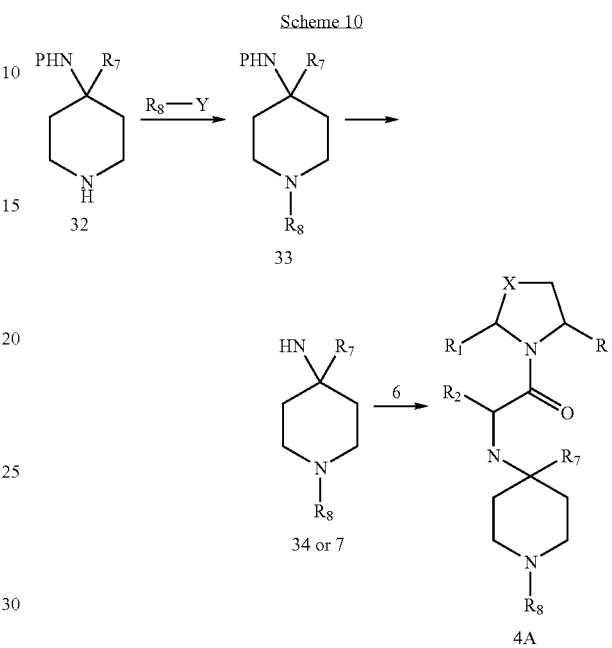

Compounds of the present invention may contain an $R_3$ group that consists of an amino-piperidine ring as described by formula 34 which are within the scope of compounds of formula 7. Such rings can be treated with compounds of general formula 6 according to conditions described in Scheme 2 to provide compounds of general formula 4 wherein $R_3$ consists of a piperidine ring. Scheme 10 describes the synthesis of compounds of formula 34 (or 7) wherein $R_3$ consists of a substituted piperidine ring. Amino-piperidine rings of formula 32, wherein P is an amino protecting group such as but not limited to tert-butyloxycarbonyl, can be treated with a halogen-substituted heterocycle or an aryl halide of formula $R_8$—Y, wherein $R_8$ consists of a heterocycle or aryl moiety and Y consists of a halogen in the presence of a base such as diisopropylethylamine in a solvent such as dioxane with heating between 50° C. and 200° C. from either a convention heat source or from a microwave source under microwave conditions to provide compounds of formula 33. Examples of $R_8$—Y include but are not limited to a 2-chloropyridine, 2-chloropyrimidine and chlorobenzene. Alternatively, compounds of formula 32 and halogen-substituted heterocycle or aryl halides of formula $R_8$—Y, may be coupled using a palladium catalyst such as $Pd_2(dba)_3$ with an appropriate ligand such as XANTHPOS in the presence of a base such as cesium carbonate in a solvent such as dioxane with heating to approximately 100° C. The protecting group can then be removed using conditions known to those skilled in the art to provide a compound of formula 7 which can be treated with compounds of formula 6 as described in Scheme 2 to provide compound of formula 4 wherein $R_3$ is a piperidine ring Alternatively, compound of formula 32 may be reacted with an acid chloride of formula $R_8C(O)Cl$, wherein $R_8$ is defined above, in the presence of a base such as triethylamine in a solvent such as dichloromethane or tetrahydrofuran to supply a compound of formula 33 wherein $R_8C(O)$— is an acyl group appended to the piperidine nitrogen. Alternatively, an acid of formula R₈C(O)OH, may be coupled to the piperidine using a coupling reagent such as but not limited to a carbodiimide or uronium salt with additives such as HOBT or DMAP. The protecting group may be removed to furnish piperidines of formula 34 which can be treated with compounds of formula 6 as described in Scheme 2 to provide compounds of formula 4 wherein $R_3$ is a piperidine.

Scheme 11

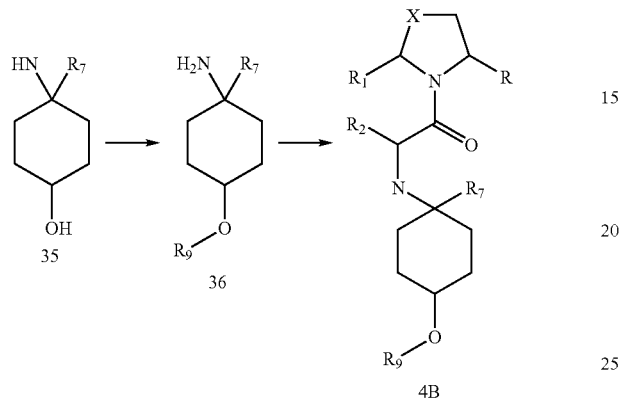

4B

Compounds of the present invention may also contain an $R_3$ group that consists of a cyclohexyl ring that is substituted with an ether group ($R_9O$—) as described by formula 36. Cyclohexyl ethers of formula 36 are synthesized from compounds of formula 35 by treatment with aryl halides or halogen-substituted aromatic heterocycles such as chloropyridines or chloropyrimidines. The appropriate 4-aminocyclohexanol of formula 35 is treated with a base such as sodium hydride in a solvent such as dimethylformamide at approximately 0° C., followed by the addition of an aryl halide or halogen-substituted aromatic heterocycle. The reaction mixture may be heated to approximately 60° C. until complete. Further derivitization of functional groups on either the heterocycle or aryl ring may be accomplished by one skilled in the art to provide compounds of formula 36. Such transformations may require appropriate protection and deprotection of the amine moiety. Compounds of formula 36 can then be treated with compounds of formula 6 as described in Scheme 2 to provide compounds of formula 4 where $R_3$ is a substituted cyclohexyl ring.

Scheme 12

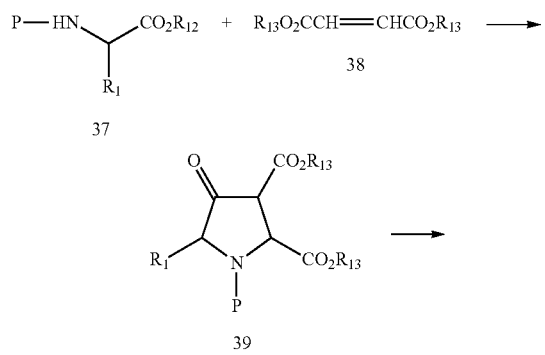

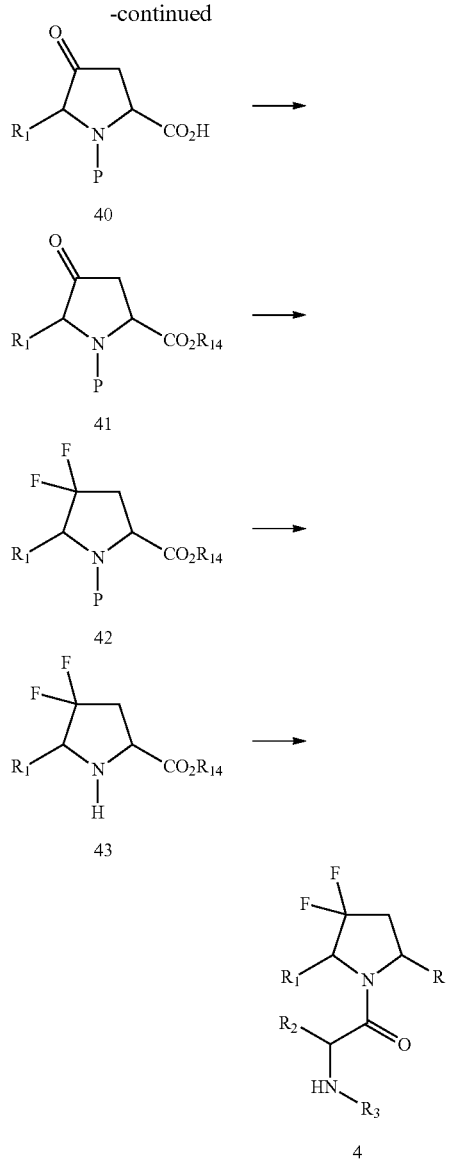

Compounds of the present invention may contain mono or difluoro pyrrolidines as represented by compound of formula 43 in Scheme 12 are also within the scope of the compounds of formula 1 shown in Scheme 1. An amino acid of formula 37 wherein P is a nitrogen protecting group and $R_{12}$ is an alkyl group, may be treated with a fumarate of formula 38 in the presence of a base such as sodium hydride in solvents such as toluene at room temperature to provide a pyrrolidine of formula 39. Compounds of formula 39 can be subjected to conditions known to cleave ester groups to provide the beta-keto dicarboxylic acid which can be subjected to conditions known to decarboxylate beta-keto carboxylic acids to form a monocarboxylic acid as described by compounds of formula 40. Esterification of the carboxylic acid in compounds of formula 40 using conditions known to those skilled in the art will provide compounds of formula 41. Treatment of compounds of formula 41 with N,N-diethylaminosulfur trifluoride (DAST) in dichloromethane at −78° C. produces the fluorinated pyrrolidines of compounds of formula 42. Removal of the protecting group yields the pyrrolidines described by the compounds of formula 43. Compounds of formula 43 which are within the scope of compounds of formula 1 can be treated according to the conditions described in Scheme 1 or 2 to provide compounds of formula 4 which contain a difluoropyrrolidine.

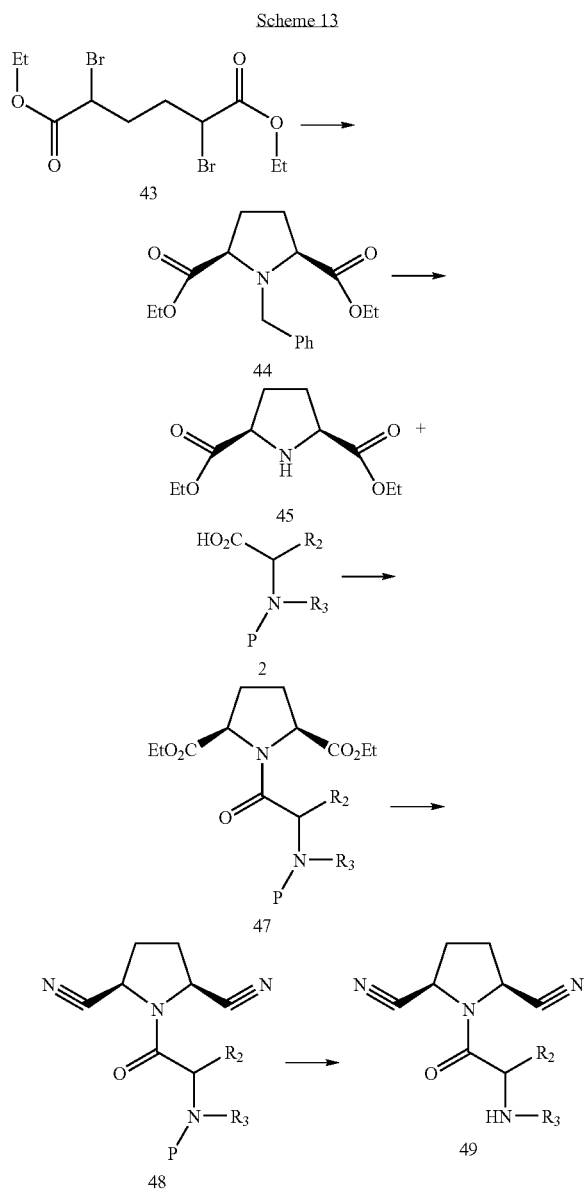

The compounds of the present invention may also contain a 2,5-dicyanopyrrolidine as represented by the compounds of formula 49 in Scheme 13. Compounds of formula 44 may be prepared by thermal cyclization of compounds of formula 43 in the presence of benzyl amine. The benzyl group of compounds of formula 44 may be removed by treatment with an atmosphere of hydrogen in the presence of a catalyst such as but not limited to 5% palladium on carbon in various solvents or by other methods known to one skilled in the art or as described in Greene, T. W. and Wuts, G. M. "Protective groups in Organic Synthesis", third ed. John Wiley & Sons, 1999 to provide compounds of formula 45. The treatment of compounds of formula 45 with a compound of formula 2 according to conditions outlined in Scheme 1 will provide compounds of formula 47. The treatment of compounds of formula 47 which contain ester groups according to the conditions outlined in Scheme 3 will provide the compounds of formula 48 that contain nitrile groups. The removal of the nitrogen protecting group P of compounds of formula 48 can be effected by treatment with reagents known to deprotect the nitrogen protecting group as known to those skilled in the art or demonstrated in Greene, T. W. and Wuts, G. M. "Protective groups in Organic Synthesis", third ed. John Wiley & Sons, 1999, to provide compounds of formula 49 which are representative of compounds of the present invention.

The compounds and processes of the present invention will be better understood by reference to the following examples, which are intended as an illustration of and not a limitation upon the scope of the invention. Further, all citations herein are incorporated by reference.

Compounds of the invention were named by ACD/ChemSketch version 5.01 (developed by Advanced Chemistry Development, Inc., Toronto, ON, Canada) or were given names consistent with ACD nomenclature.

EXAMPLES

Example 1

(2S,5R)-5-ethynyl-1-L-leucylpyrrolidine-2-carbonitrile

Example 1A dimethyl (2S)-5-oxopyrrolidine-1,2-dicarboxylate

To a cold (−78° C.) solution of methyl (S)-(+)-2-pyrrolidone-5-carboxylate (4.80 grams, 33.5 mmol) in tetrahydrofuran (90 mL) was added a solution of lithium bis(trimethylsilyl) amide (1 M solution in hexanes, 40.0 mL, 40.0 mmol) dropwise via syringe over 15 minutes; then methyl chloroformate (2.90 mL, 36.9 mmol) was added dropwise via syringe over 5 minutes. The resulting slurry was stirred at −78° C. for 1 hour after which the reaction was quenched with 1 M HCl (50 mL). The mixture was allowed to come to room temperature, concentrated under reduced pressure and the residue partitioned between ethyl acetate (200 mL) and 1 M HCl (200 mL). The aqueous layer was extracted with ethyl acetate (2×200 mL) and the combined organic layers were dried (sodium sulfate), filtered, and concentrated to provide the titled compound. MS (DCI/NH$_3$) m/e 202 (M+H)$^+$; $^1$H NMR (300 MHz, CDCl$_3$): δ ppm 4.70 (dd, 1H), 3.88 (s, 3H), 3.80 (s, 3H), 2.74-2.30 (m, 3H), 2.15-2.05 (m, 1H).

Example 1B dimethyl (2S)-5-methoxypyrrolidine-1,2-dicarboxylate

To a cold solution (−78° C.) of dimethyl (2S)-5-oxopyrrolidine-1,2-dicarboxylate (5.80 g, 28.8 mmol) in tetrahydrofuran (100 mL) was added a solution of lithium triethylborohydride (1 M in THF, 35 mL, 35 mmol) dropwise via syringe over 10 minutes. The resulting solution was stirred at −78° C. for 30 minutes, quenched by the careful addition of saturated sodium bicarbonate solution (50 mL), allowed to warm to 0° C. and 30% hydrogen peroxide (6 mL) was carefully added dropwise. The mixture was stirred for 30 minutes at room temperature, reduced in volume under reduced pressure, and diluted with ethyl acetate (300 mL) and brine (200 mL). The milky aqueous layer was separated and further extracted with ethyl acetate (2×300 mL). The combined organic layers were dried (sodium sulfate), filtered, and concentrated to a light yellow oil. The yellow oil was taken up in methanol (50 mL) containing para-toluenesulfonic acid hydrate (487 mg, 2.6 mmol) and stirred at room temperature for 16 hours. The reaction was diluted with aqueous sodium bicarbonate solution (40 mL), the volatile solvents were removed under reduced pressure and the residue partitioned between ethyl acetate (200 mL) and brine (200 mL). The aqueous layer was further extracted with ethyl acetate (200 mL), the combined organic layers were dried (sodium sulfate), filtered, and concentrated to an oil which was chromatographed on a Biotage 40M with 60% hexane/40% ethyl acetate to provide the titled compound as a mixture of diastereomers. (mixture of amide bond rotomers) $^1$H NMR (300 MHz, CDCl$_3$): δ ppm 5.37 (d, 1H), 5.33 (dd, 1H), 5.24 (d, 1H), 5.18 (dd, 1H), 4.44-4.31 (m, 2H), 3.76 (s, 3H), 3.73 (s, 3H), 3.72 (s, 3H), 3.42 (s, 3H), 3.34 (s, 3H).

Examples 1C and 1D dimethyl (2S,5R)-5-((trimethylsilyl)ethynyl)pyrrolidine-1,2-dicarboxylate and dimethyl (2S,5S)-5-((trimethylsilyl)ethynyl)pyrrolidine-1,2-dicarboxylate To a cold −45° C. solution of dimethyl (2S)-5-methoxy-pyrrolidine-1,2-dicarboxylate (3.30 g, 15.20 mmol) and bist-rimethylsilylacetylene (5.20 g, 30.4 mmol, 2.0 equiv) in methylene chloride (45 mL) was added a solution of tin (IV) chloride (1 M in methylene chloride, 20.0 mL, 20.0 mmol, 1.3 equiv) dropwise via syringe over 15 minutes. To the dark yellow solution was added solid aluminum chloride (2.77 g, 20.8 mmol, 1.4 equiv) in one portion. The resulting mixture was allowed to warm to room temperature and stirred at room temperature for 48 hours. The reaction mixture was carefully poured into aqueous sodium bicarbonate solution (100 mL) with ice cooling. A white precipitate forms and 1 M HCl (ca. 50 mL) was added until the solids dissolved. This mixture was extracted with ethyl acetate (2×200 mL). The combined organic layers were filtered, dried (sodium sulfate), filtered, and concentrated. The residue was chromatographed on a Biotage flash 40 M eluting with 70% hexane/30% ethyl acetate to afford (2S,5S)-5-((trimethylsilyl)ethynyl)pyrrolidine-1,2-dicarboxylate (trans compound Rf of 0.3 in 70% hexane/30% ethyl acetate) and dimethyl (2S,5R)-5-((trimethylsilyl)ethynyl)pyrrolidine-1,2-dicarboxylate (cis compound Rf of 0.2 in 70% hexane/30% ethyl acetate). Data for example 1D: MS (DCI/NH$_3$) m/e 284 (M+H)$^+$; The compound exists as a mixture of rotomers. $^1$H NMR (300 MHz, CDCl$_3$): δ ppm 4.60 (d, 1H), 4.51 (d, 1H), 4.30 (d, 1H), 4.24 (d, 1H), 3.62 (s, 3H), 3.59 (s, 3H), 3.57 (s, 3H), 3.54 (s, 3H), 2.40-2.28 (m, 2H), 2.11-2.04 (m, 2H), 1.90-1.81 (m, 4H), 0.0 (s, 18H). Data for example 1C: MS (DCI/NH$_3$) m/e 284 (M+H)$^+$; $^1$H NMR (300 MHz, CDCl$_3$): δ ppm 4.55-4.40 (m, 1H), 4.20-4.15 (m, 1H), 3.59 (s, 6H), 2.15-1.89 (m, 4H), 0.00 (s, 9H).

Example 1E methyl (5R)-5-((trimethylsilyl)ethynyl)-L-prolinate

A solution of dimethyl (2S,5R)-5-((trimethylsilyl)ethynyl) pyrrolidine-1,2-dicarboxylate (5.43 g, 19.16 mmol) and iodotrimethylsilane (3 mL, 28.74 mmol) in chloroform (100 mL) was heated to 65° C. for 3 hours, was cooled to room temperature, concentrated under reduced pressure and flash chromatographed with 35% ethyl acetate/65% hexane to provide the titled compound. MS (DCI/NH$_3$) m/e 226 (M+H)$^+$.

Example 1F methyl N-(tert-butoxycarbonyl)-L-leucyl-(5R)-5-((trimethylsilyl)ethynyl)-L-prolinate To a solution of methyl (5R)-5-((trimethylsilyl)ethynyl)-L-prolinate (1.6 grams, 7.48 mmol), dimethylaminopyridine (913 mg, 7.48 mmol), N-methylmorpholine (1.23 mL, 11.22 mmol), and N-(tert-butoxycabonyl)-L-leucine monohydrate (2.24 g, 8.98 mmol) in dichloromethane (30 mL) at room temperature was added 1-(3-dimethylaminopropyl)-3-ethyl-carbodiimide hydrochloride (1.72 g, 8.98 mmol). The resulting mixture was stirred 16 hours at room temperature, and partitioned between ethyl acetate (200 mL) and 1 M HCl (200 mL). The aqueous layer was further extracted with ethyl acetate (200 mL). The combined organic layers were dried (sodium sulfate), filtered, and concentrated. The residue was chromatographed with a Biotage 40 M cartridge with 40% ethyl acetate/hexane provide the titled compound. MS (DCI/NH$_3$) m/e 439 (M+H)$^+$.

Example 1G

N-(tert-butoxycarbonyl)-L-leucyl-(5R)-5-ethynyl-L-proline

To a solution of methyl N-(tert-butoxycarbonyl)-L-leucyl-(5R)-5-((trimethylsilyl)ethynyl)-L-prolinate (1.24 g, 2.83 mmol) in dioxane (12 mL) at room temperature was added a solution of 2 M lithium hydroxide (3 mL, 6.0 mmol). The resulting mixture was stirred at room temperature for 6 hours. The reaction was diluted with 1 M HCl solution (50 mL), and the aqueous mixture was extracted with ethyl acetate (3×50 mL). The combined organic layers were dried (sodium sulfate), filtered, and concentrated to provide the titled compound.

Example 1H

N-(tert-butoxycarbonyl)-L-leucyl-(5R)-5-ethynyl-L-prolinamide

To a cold (0° C.) solution of N-(tert-butoxycarbonyl)-L-leucyl-(5R)-5-ethynyl-L-proline (2.83 mmol) and N-methyl morpholine (0.39 mL, 3.50 mmol) in THF (15 mL) was added isobutyl chloroformate (0.42 mL, 3.25 mmol). The resulting cloudy white mixture was stirred at 0° C. for 30 minutes followed by the addition of a solution of ammonia (0.5 M in dioxane, 10.0 mL, 5.0 mmol). The solution was allowed to warm to room temperature and stirred for 16 hours. The reaction mixture was diluted by the addition of 1 M HCl (100 mL), and extracted with ethyl acetate (3×100 mL). The combined organic layers were dried (sodium sulfate), filtered, and concentrated to provide the titled compound.

Example 1I

N-(tert-butoxycarbonvl)-L-leucyl-(5R)-5-ethynyl-L-pyrrolidine-2-carbonitrile

To a cold solution (−40° C.) of N-(tert-butoxycarbonyl)-L-leucyl-(5R)-5-ethynyl-L-prolinamide (1.07 g, 3.05 mmol) and imidazole (208 mg, 3.05 mmol) in pyridine (15 mL) was added POCl$_3$ (0.57 mL, 6.10 mmol) via syringe. The resulting mixture was stirred, maintaining the temperature below −20° C., for 1 hour followed by the addition of 1 M HCl (100 mL). The aqueous mixture was extracted with ethyl acetate (3×100 mL), and the combined organic layers were dried (sodium sulfate), filtered, concentrated and chromatographed with 30% ethyl acetate/hexane to provide the titled compound. MS (DCI/NH$_3$) m/e 334 (M+H)$^+$; $^1$H NMR (300 MHz, CDCl$_3$): δ ppm 5.15 (t, 1H), 4.95 (d, 1H), 4.71 (t, 1H), 4.53 (ddd, 1H), 2.50 (d, 1H), 2.50-2.28 (m, 4H), 1.75-1.57 (m, 3H).

Example 1

(2S,5R)-5-ethynyl-1-L-leucylpyrrolidine-2-carbonitrile hydrochloride

To a solution of N-(tert-butoxycarbonyl)-L-leucyl-(5R)-5-ethynyl-L-pyrrolidine-2-carbonitrile (250 mg) in ether (1 mL) was added 4 M HCl in dioxane (2 mL). The resulting mixture was stirred at room temperature for 5 hours and the solvents removed under reduced pressure. The white solid was triturated with ether to provide the titled compound. MS (DCI/NH$_3$) m/e 234 (M+H)$^+$; $^1$H NMR (300 MHz, MeOH-d$_4$): δ ppm 5.11 (d, 1H), 4.82 (m, 1H), 4.42 (dd, 1H), 3.19 (d, 1H), 2.58-2.56 (m, 1H), 2.49-2.24 (m, 3H), 2.05-1.95 (m, 1H), 1.87-1.81 (m, 2H), 1.08 (d, 3H), 1.04 (d, 3H).

Example 2

(2S,5R)-5-ethynyl-1-((3S)-1,2,3,4-tetrahydroisoquinolin-3-ylcarbonyl)pyrrolidine-2-carbonitrile hydrochloride Example 2 was prepared using the same procedures as described for Example 1 substituting (3S)-2-(t-butoxycarbonyl)-1,2,3,4-tetrahydroisoquinoline-3-carboxylic acid for N-(t-butoxycarbonyl)-L-leucine monohydrate in the step described in example 1F. MS (DCI/NH$_3$) m/e 280 (M+H)$^+$; $^1$H NMR (300 MHz, MeOH-d$_4$): δ ppm 7.33-7.26 (m, 4H), 5.18 (m, 1H), 4.80 (dd, 1H), 4.49 (m, 2H), 3.75 (m, 1H), 3.30-3.19 (m, 2H), 2.57-2.23 (m, 4H).

Example 3

(2S,5R)-1-((2S)-2-amino-2-cyclopentylethanoyl)-5-ethynylpyrrolidine-2-carbonitrile

Example 3A methyl (5R)-1-{(2S)-2-((tert-butoxycarbonyl)amino)-2-cyclopentylethanoyl}-5-((trimethylsilyl)ethynyl)-L-prolinate To a stirred solution of methyl (5R)-5-((trimethylsilyl)ethynyl)-L-prolinate (1.2 g, 5.32 mmol) in dichloromethane (30 mL) at ambient temperature under nitrogen was added 4-dimethylamino pyridine (0.65 g, 5.32 mmol), 4-methylmorpholine (0.9 mL, 7.98 mmol), 1-(3-(dimethylamino)propyl)-3-ethyl carbodiimide hydrochloride (1.22 g, 6.39 mmol), and (2S)-((tert-butoxycarbonyl)amino)(cyclopentyl)acetic acid dicyclohexylamine salt (1.55 g, 6.39 mmol). The reaction mixture was stirred at room temperature for 16 hours, diluted with ethyl acetate and washed with 1 M HCl. The aqueous layer was further extracted with ethyl acetate (2×) and the combined ethyl acetate layers were dried (Na$_2$SO$_4$) and evaporated. The residue was purified by flash chromatography 30% ethyl acetate/hexane to provide the titled compound. MS (CI) m/e 451 (M+H)$^+$.

Example 3B

(5R)-1-{(2S)-2-((tert-butoxycarbonyl)amino)-2-cyclopentylethanoyl}-5-ethynyl-L-proline To a stirred solution of methyl (5R)-1-{(2S)-2-((tert-butoxycarbonyl)amino)-2-cyclopentylethanoyl}-5-((trimethylsilyl)ethynyl)-L-prolinate (1.65 g, 3.66 mmol) in MeOH (10 mL) and H$_2$O (10 mL) at room temperature was added LiOH.H$_2$O (0.23 g, 5.49 mmol). The reaction mixture was stirred at room temperature for 16 hours and concentrated under reduced pressure. The residue was taken up in water and extracted with diethyl ether (2×). The aqueous layer was acidified to pH ~4 by adding 4% KHSO$_4$ dropwise. The clear solution was extracted with ethyl acetate (3×) and the combined ethyl acetate layers were washed with brine, dried (Na$_2$SO$_4$), filtered and concentrated under reduced pressure to provide the titled compound. MS (CI) m/e 365 (M+H)$^+$.

Example 3C

(5R)-1-{(2S)-2-((tert-butoxycarbonyl)amino)-2-cyclopentylethanoyl}-5-ethynyl-L-prolinamide To a stirred solution of (5R)-1-{(2S)-2-((tert-butoxycarbonyl)amino)-2-cyclopentylethanoyl}-5-ethynyl-L-proline (1.28 g, 3.38 mmol) in THF (25 mL) at −15° C. under nitrogen, was added 4-methylmorpholine (0.44 mL, 4.05 mmol), and isobutylchloroformate (0.5 mL, 3.72 mmol) over 2 minutes. The reaction mixture was stirred at −15° C. under nitrogen for 30 minutes, and a solution of 0.5 M NH$_3$ in dioxane (34 mL, 16.90 mmol) was added. The reaction mixture diluted with water, the pH adjusted to 4 by the addition of 4% KHSO$_4$ and extracted with ethyl acetate (3×). The combined extracts were washed with brine, dried (Na$_2$SO$_4$), filtered and evaporated. The residue was purified by flash column chromatography (5% MeOH/CH$_2$Cl$_2$) to provide the titled compound. MS (CI) m/e 364 (M+H)$^+$.

Example 3D

(5R)-1-{(2S)-2-((tert-butoxycarbonyl)amino)-2-cyclopentylethanoyl}-5-ethynyl-L-pyrrolidine-2-carbonitrile Trifluoroacetic anhydride (0.086 mL, 0.605 mmol), was added dropwise to a stirred ice-cooled solution of (5R)-1-{(2S)-2-((tert-butoxycarbonyl)amino)-2-cyclopentylethanoyl}-5-ethynyl-L-prolinamide (200 mg, 0.55 mmol) in anhydrous dioxane (7 mL) and anhydrous pyridine (0.089 mL, 1.1 mmol) at such a rate that the temperature was kept below 5° C. The reaction mixture was allowed to warm to room temperature and stirred for 16 hours. Ice was added to the residue, the solid product was collected by filtration and washed with water. Purification by flash chromatography (30% ethyl acetate/hexane) provided the titled compound. MS (CI) m/e 346 (M+H)$^+$.

Example 3E

(2S,5R)-1-((2S)-2-amino-2-cyclopentylethanoyl)-5-ethynylpyrrolidine-2-carbonitrile hydrochloride (5R)-1-{(2S)-2-((tert-butoxycarbonyl)amino)-2-cyclopentylethanoyl}-5-ethynyl-L-pyrrolidine-2-carbonitrile (0.03 mg, 0.087 mmol), and 4 M HCl in dioxane (0.15 mL, 0.6 mmol) were stirred at room temperature for 2 hours and evaporated under reduced pressure. Diethyl ether was added to the residue, and the formed precipitate filtered. The solid was washed with diethyl ether (3×15 mL). The precipitate was dried in vacuo to provide the titled compound. MS (CI) m/z 246 (M+H)$^+$; $^1$H NMR (300 MHz, MeOH-d$_4$): δ ppm 5.05 (m, 1H), 4.8 (t, 1H), 4.3 (d, 1H) 3.19 (d, 1H), 2.4-2.68 (m, 3H), 2.2-2.28 (m, 2H), 1.4-1.9 (m, 8H).

Example 4

(2S,5R)-1-((2S)-2-amino-2-cyclopentylethanoyl)-5-vinylpyrrolidine-2-carbonitrile hydrochloride Example 4A tert-butyl (1S)-2-((2S,5R)-2-cyano-5-vinylpyrrolidin-1-yl)-1-cyclopentyl-2-oxoethylcarbamate (5R)-1-{(2S)-2-((tert-butoxycarbonyl)amino)-2-cyclopentylethanoyl}-5-ethynyl-L-pyrrolidine-2-carbonitrile (60 mg) was stirred under hydrogen (60 psi) at room temperature for 7 minutes in a mixture of quinoline (66 uL) and ethyl acetate (6 mL) using 5% Pd/BaSO$_4$ (24 mg). The mixture was filtered and the filtrate concentrated under reduced pressure. Purification by flash column chromatography with 20% ethyl acetate/hexane to provide the titled compound. MS (CI) m/e 348 (M+H)$^+$.

Example 4

(2S,5R)-1-((2S)-2-amino-2-cyclopentylethanoyl)-5-vinylpyrrolidine-2-carbonitrile hydrochloride Example 4 was prepared according to the procedure for Example 3E substituting tert-butyl (1S)-2-((2S,5R)-2-cyano-5-vinylpyrrolidin-1-yl)-1-cyclopentyl-2-oxoethylcarbamate for (5R)-1-{(2S)-2-((tert-butoxycarbonyl)amino)-2-cyclopentylethanoyl}-5-ethynyl-L-pyrrolidine-2-carbonitrile. MS (CI) m/e 248 (M+H)$^+$; $^1$H NMR (300 MHz, MeOH-d$_4$): δ ppm 5.98-6.09 (m, 1H), 5.3-5.39 (m, 2H), 4.7-4.8 (m, 1H), 4.1 (d, 1H), 2.38-2.49 (m, 2H), 2.18-2.33 (m, 2H), 1.96-2.02 (m, 2H), 1.58-1.83 (m, 6H), 1.3-1.47 (m, 2H).

Example 5

(2S,5R)-1-((2S)-2-amino-2-cyclohexylethanoyl)-5-ethynylpyrrolidine-2-carbonitrile hydrochloride Example 5 was prepared according to the procedures for Example 1F-J substituting N-(t-butoxycarbonyl)-(2S)-amino(cyclohexy)acetic acid for N-(t-butoxycarbonyl)-L-leucine monohydrate in the step described in Example 1F. MS (CI) m/e 260 (M+H)$^+$; $^1$H NMR (300 MHz, MeOH-d$_4$): δ ppm 5.58 (m, 1H), 5.0 (t, 1H), 4.24 (d, 1H), 3.2 (d, 1H), 2.3-2.42 (m, 3H), 1.8-1.84 (m, 2H), 1.12-1.4 (m, 10H).

Example 6

(2S,5S)-5-ethyl-1-L-leucylpyrrolidine-2-carbonitrile

Example 6A ethyl (2S)-2-((tert-butoxycarbonyl)amino)-5-oxoheptanoate

Ethyl N-Boc (S)-pyroglutamate (2.33 g, 9.06 mmol, prepared as described in: (a) St-Denis, Y., Augelli-Szafran, C. E.; Bachand, B.; Berryman, K. A.; DiMaio, J.; Doherty, A. M.; Edmunds, J. J.; Leblond, L.; Levesque, S.; Narasimhan, L. S.; Penvose-Yi, J. R.; Rubin, J. R.; Tarazi, M.; Winocour, P. D.; Siddiqui, M. A. *Biorg. Med. Chem. Lett.* 1998, 8, 3193-3198. (b) Jain, R. *Org. Prep. Procd. Intl.* 2001, 33, 405-409.) was dissolved in THF (6 mL) and the mixture was cooled to −40° C. Ethyl magnesiumbromide solution (1.0 M in THF, 10.84 mL, 10.84 mmol) was added slowly via syringe, and the mixture was stirred cold for 2 hours. Then the reaction flask was placed in a freezer (approx −20° C.) for 16 hours, the reaction was allowed to warm to room temperature and aqueous NH$_4$Cl and 1 N HCl were added. The mixture was extracted with ethyl acetate (3×). The combined organic extracts were dried (Na$_2$SO$_4$), filtered, concentrated and purified by flash chromatography (30% ethyl acetate/hexane) to provide the titled compound. MS (ESI) m/z 288 (M+H)$^+$, 310 (M+Na)$^+$.

Example 6B ethyl (2S)-5-ethyl-3,4-dihydro-2H-pyrrole-2-carboxylate

Ethyl (2S)-2-((tert-butoxycarbonyl)amino)-5-oxoheptanoate and trifluoroacetic acid (3 mL) were stirred in dichloromethane (3 mL) at room temperature for 3 hours. The mixture was concentrated under reduced pressure to provide the titled compound. MS (ESI) m/z 170 (M+H)$^+$.

Example 6C ethyl (5S)-5-ethyl-L-prolinate

Ethyl (2S)-5-ethyl-3,4-dihydro-2H-pyrrole-2-carboxylate dissolved in ethanol (32 mL) was stirred with 0.30 g of 10% Pd/C and under hydrogen (60 psi) for 16 hours. The catalyst was removed by filtration, and the filtrate was concentrated under reduced pressure to provide the titled compound. MS (CI) m/z 172 (M+H)$^+$.

Example 6D ethyl N-(tert-butoxycarbonyl)-L-leucyl-(5S)-5-ethyl-L-prolinate

A solution of ethyl (5S)-5-ethyl-L-prolinate (2.5 mmol), 2-(1H-benzotriazol-1yl)-1,1,3,3-tetramethyluronium tetrafluoroborate (1.00 g, 3.13 mmol) and N-(tert-butoxycarbonyl)-L-leucine hydrate (0.779 g, 3.12 mmol) were mixed in 4 mL of dimethylformamide. Triethylamine (approx 1.1 mL) was added until the pH reached about 6 (wet pH paper). After stirring for 16 hours, the mixture was concentrated under reduced pressure and the residue partitioned between 1 N HCl and ethyl acetate. The organic layer was washed with saturated NaHCO$_3$, dried (Na$_2$SO$_4$), filtered, concentrated under reduced pressure and purified by flash chromatography (30% to 50% ethyl acetate/hexane) to provide the titled compound. MS (ESI) m/z 385 (M+H)$^+$.

Example 6E

N-(tert-butoxycarbonyl)-L-leucyl-(5S)-5-ethyl-L-proline

Ethyl N-(tert-butoxycarbonyl)-L-leucyl-(5S)-5-ethyl-L-prolinate (0.965 g, 2.5 mmol) was dissolved in 3 mL of ethanol. The resultant solution was treated with 1.2 M LiOH solution (3.8 mL, 4.52 mmol) at room temperature. After 4 hours, the volatiles were removed under reduced pressure, and 1 N HCl was added. The mixture was extracted with ethyl acetate (3×), and the combined organics were washed with brine, dried (Na$_2$SO$_4$), filtered and concentrated under reduced pressure to provide the titled compound. MS (ESI) m/z 357 (M+H)$^+$.

Example 6F

N-(tert-butoxycarbonyl)-L-leucyl-(5S)-5-ethyl-L-prolinamide

N-(tert-butoxycarbonyl)-L-leucyl-(5S)-5-ethyl-L-proline was mixed with triethylamine (0.426 mL, 3.25 mmol) in THF (4 mL) and cooled to 0° C. followed by the addition of ethyl chloroformate (0.287 mL, 3.0 mmol). After 20 minutes, 0.5 M ammonia in dioxane (6 mL) was added. After 4 hours, the mixture was concentrated, and the residue was partitioned between 1 N HCl and ethyl acetate. The organic extracts were washed with saturated NaHCO$_3$, dried (Na$_2$SO$_4$), filtered, concentrated under reduced pressure and purified by flash chromatography (80% to 100% ethyl acetate/hexane) to provide the titled compound. MS (ESI) m/z 356 (M+H)$^+$.

Example 6G

N-(tert-butoxycarbonyl)-L-leucyl-(5S)-5-ethyl-L-pyrrolidine-2-carbonitrile

N-(tert-butoxycarbonyl)-L-leucyl-(5S)-5-ethyl-L-prolinamide (0.392 g, 1.10 mmol) and imidazole (0.082 g, 1.21 mmol) were mixed in pyridine (4 mL) and cooled to ±35° C. followed by addition of POCl$_3$ (0.206 mL, 2.20 mmol). After 1 hour, aqueous NH$_4$Cl solution was added, and the mixture was concentrated under reduced pressure. 1 N HCl was added to the residue, and the mixture was extracted with ethyl acetate (3×). The combined organic extracts were washed with 1 N HCl and brine, dried (Na$_2$SO$_4$), and concentrated under reduced pressure to provide the titled compound. MS (ESI) m/z 338 (M+H)$^+$. NOE from ROESY spectrum confirmed the cis-relationship between 2-cyano and 5-ethyl groups.

Example 6

(2S,5S)-5-ethyl-1-L-leucylpyrrolidine-2-carbonitrile trifluoroacetate

N-(tert-butoxycarbonyl)-L-leucyl-(5S)-5-ethyl-L-pyrrolidine-2-carbonitrile (299 mg) was mixed with 2 mL each of dichlormethane and trifluoroacetic acid at room temperature. After 3 hours, the volatiles were removed under reduced pressure to provide the titled compound as the trifluoroacetic acid salt. $^1$H NMR (400 MHz, CDCl$_3$) δ 4.76 (t, 1H, J=8.0 Hz), 4.27 (d, 1H, J=8.6 Hz), 4.04 (s, 1H), 2.26-2.38 (m, 2H), 1.87-2.05 (m, 4H), 1.66 (m, 3H), 1.31 (m, 1H), 0.96-1.02 (m, 9H); MS (ESI) m/z 238 (M+H)$^+$.

Example 7

(2S,5S)-1-((2S)-2-amino-2-cyclohexylethanoyl)-5-ethylpyrrolidine-2-carbonitrile trifluoroacetate The titled compound was prepared according to procedure described in Example 6 by substituting N-(tert-butoxycarbonyl)-L-leucine hydrate with N-Boc-L-cyclohexylglycine in step 6D. $^1$H NMR (400 MHz, MeOH-d$_4$) δ 5.09 and 4.16 (m, 1H), 4.83 (t, 1H J=8.2 Hz), 4.00 (t, 1H, J=7.4 Hz), 2.48 (m, 1H), 2.30 (m, 2H), 2.08 (m, 2H), 1.85 (m, 4H), 1.71 (m, 3H), 1.17-1.33 (m, 5H), 1.02 and 0.95 (t, 3H, J=7.5 Hz); $^{13}$C NMR (MeOH-d$_4$, 100 MHz) δ 119.7 and 119.9 ppm for CN group; MS (ESI) m/z 264 (M+H)$^+$.

Example 8

(2S,5R)-1-{N-((1R,2R,4S)-bicyclo(2.2.1)hept-2-yl)glycyl}-5-ethynylpyrrolidine-2-carbonitrile Example 8A methyl (5R)-1-(chloroacetyl)-5-((trimethylsilyl)ethynyl)-L-prolinate To a stirred solution of methyl (5R)-5-((trimethylsilyl)ethynyl)-L-prolinate (2.76 g, 12.2 mmol) and triethylamine (2.13 mL, 15.3 mmol) in dry tetrahydrofuran (50 mL) at 0° C. was gradually added a solution of chloroacetyl chloride (0.97 mL, 12.2 mmol) in dry tetrahydrofuran (10 mL). After stirring at room temperature for 2 hours, the mixture was filtered. The solid cake was washed with THF, and the filtrate and washings were combined, dried over sodium sulfate and concentrated under reduced pressure. The residue taken up in toluene and concentrated to dryness under reduced pressure to provide the titled compound. MS (CI) m/z 302 (M+1)$^+$.

Example 8B (5R)-1-(chloroacetyl)-5-ethynyl-L-proline

To a stirred solution of methyl (5R)-1-(chloroacetyl)-5-((trimethylsilyl)ethynyl)-L-prolinate (3.69 g, 12.2 mmol) in MeOH (24 mL) and H$_2$O (24 mL) at room temperature was added LiOH.H$_2$O (0.8 g, 18 mmol). The reaction mixture was stirred at ambient temperature overnight and concentrated under reduced pressure. The residue was taken up in water and extracted with diethyl ether (2×). The aqueous layer was acidified to pH ~3 by adding 4% KHSO$_4$ dropwise. The solution was extracted with ethyl acetate (3×). Combined ethyl acetate layers were washed with brine, dried (Na$_2$SO$_4$), filtered and concentrated under reduced pressure to provide the titled compound. MS (CI) m/z 216 (M+1)$^+$.

Example 8C (5R)-1-(chloroacetyl)-5-ethynyl-L-prolinamide

To a stirred solution of (5R)-1-(chloroacetyl)-5-ethynyl-L-proline (1.89 g, 8.76 mmol) in THF (50 mL) at ±15° C. under nitrogen was added 4-methylmorpholine (1.16 mL, 10.52 mmol), and then isobutylchloroformate (1.25 mL, 9.64 mmol) over 3 minutes. A white precipitate formed. The reaction mixture was stirred at ±15° C. under nitrogen for 30 minutes, and a solution of NH$_3$ in dioxane (0.5 M, 88 mL, 43.8 mmol) was added. The reaction mixture was stirred at ±15° C. for 30 minutes, warmed to room temperature, and stirred at that temperature for 16 hours. The reaction mixture was diluted with 4% KHSO$_4$ to ~pH 4 and extracted with ethyl acetate (3×). The extracts were combined, washed with brine, dried (Na$_2$SO$_4$), filtered and concentrated under reduced pressure. Purification by flash column chromatography (60-75% ethyl acetate/hexane) provided the titled compound. MS (CI) m/z 215 (M+1)$^+$.

Example 8D

(2S,5R)-1-(chloroacetyl)-5-ethynylpyrrolidine-2-carbonitrile

To a stirred solution of (5R)-1-(chloroacetyl)-5-ethynyl-L-prolinamide (0.16 g, 0.745 mmol) and imidazole (0.05 g, 0.745 mmol) in dry pyridine (4 mL) at −35° C. under nitrogen was added POCl₃ (0.15 mL, 1.49 mmol) dropwise. The reaction mixture was stirred between −35° C. to ±15° C. for 1 hour and evaporated. The residue was diluted with dichloromethane and washed with H₂O (2×), dried (Na₂SO₄), filtered and concentrated under reduced pressure. Purification by flash chromatography (10% ethyl acetate/hexane) provided the titled compound. MS (CI) m/z 197 (M+1)⁺.

Example 8

(2S,5R)-1-{N-((1R,2R,4S)-bicyclo(2.2.1)hept-2-yl)glycyl}-5-ethynylpyrrolidine-2-carbonitrile To a stirred solution of (2S,5R)-1-(chloroacetyl)-5-ethynylpyrrolidine-2-carbonitrile (0.03 g, 0.152 mmol) in acetonitrile (1 mL) at room temperature was added exo-2-aminonorborane (0.036 mL, 0.305 mmol) and a catalytic amount of tetrabutylammonium iodide. The reaction mixture was stirred at room temperature for 18 hours, concentrated under reduced pressure and purified by flash chromatography with 3% methanol:dichloromethane to provide the titled compound. MS (CI) m/z 271 (M+1)⁺; ¹H NMR (300 MHz, MeOH-d₄): δ ppm 4.7-4.8 (m, 2H), 3.61-3.8 (m, 2H), 3.2-3.3 (m, 1H), 3.02-3.11 (1H, s), 2.62-2.72 (m, 1H), 2.37-2.44 (m, 3H), 2.2-2.3 (br s, 2H), 1.0-1.7 (m, 8H).

Example 28

(2S,5S)-1-L-leucyl-5-methylpyrrolidine-2-carbonitrile

The title compound was prepared in the manner described for example 6 except methyl magnesium bromide was substituted for ethyl magnesium bromide in the step corresponding to Example 6A. ¹H NMR (400 MHz, MeOH-d₄) δ 4.79 (dd, 1H, J=8.1 Hz), 4.40 (m, 1H), 4.30 (dd, 1H, J=4.1, 9.4 Hz), 2.37-2.50 (m, 2H), 2.08 (m, 1H), 1.75-1.92 (m, 3H), 1.66 (m, 1H), 1.36 (d, 3H, J=6.5 Hz), 1.05 (d, 3H, J=4.3 Hz), 1.04 (d, 3H, J=4.3 Hz); ¹³C NMR (100 MHz, MeOH-d₄) δ 119.9 for CN group; MS (ESI) m/z 224 (M+H)⁺.

Example 29

(2S,5R)-5-ethynyl-1-(N-(4-methyl-1-pyridin-2-ylpiperidin-4-yl) glycyl)pyrrolidine-2-carbonitrile

Example 29A

4-Methyl-3,4,5,6-tetrahydro-2H-(1,2')bipyridinyl-4-ylamine

A stirred solution of (4-methyl-piperidin-4-yl)-carbamic acid benzyl ester (0.15 g, 0.61 mmol, Example 30B) and 2-fluoropyridine (0.3 mL, 3.5 mmol) was heated to 175° C. under microwave conditions for 1 hour. The reaction mixture was concentrated under reduced pressure and purified by chromatography (silica gel, eluting with 20% to 35% ethyl acetate in hexane) to provide (4-methyl-3,4,5,6-tetrahydro-2H-(1,2')bipyridinyl-4-yl)-carbamic acid benzyl ester. MS (CI) m/z 326 (M+1)⁺; ¹H NMR (300 MHz, CDCl₃) δ ppm 8.06 (dd 1H), 7.52 (m, 1H), 7.37-7.26 (m, 5H), 6.80 (d, 1H), 6.62 (t, 1H), 5.04 (s, 2H), 4.84 (s, 1H), 3.78 (m, 2H), 3.25-3.16 (m, 2H), 2.08 (m, 2H), 1.64-1.55 (m, 2H), 1.35 (s, 3H).

To a stirred solution of (4-methyl-3,4,5,6-tetrahydro-2H-(1,2')bipyridinyl-4-yl)-carbamic acid benzyl ester (0.06 g, 0.185 mmol) in isopropanol (1.8 mL) at room temperature was added ammonium formate (0.047 g, 0.75 mmol) and 5 mg of 10% Pd/C under nitrogen. The reaction mixture was heated under microwave conditions at 150° C. for 30 minutes, cooled, filtered through Celite and concentrated under reduced pressure to provide the titled compound. MS (CI) m/z 192 (M+1).

Example 29B

(2S,5R)-5-ethynyl-1-(N-(4-methyl-1-pyridin-2-ylpiperidin-4-yl) glycyl)pyrrolidine-2-carbonitrile To a stirred solution of (2S,5R)-1-(chloroacetyl)-5-ethynylpyrrolidine-2-carbonitrile (0.039 g, 0.2 mmol, Example 8D) in acetonitrile (3 mL) at room temperature was added 4-methyl-3,4,5,6-tetrahydro-2H-(1,3')bipyridinyl-4-ylamine (0.076 g, 0.4 mmol). The reaction mixture was stirred at 66° C. for 48 hours, concentrated under reduced pressure and purified by chromatography (silica gel, eluting with 2%-5% methanol:dichloromethane). The product was mixed with 4M HCl in dioxane (2 mL), and after 0.5 hours, the solvents were removed under reduced pressure. The residue was solidified by trituration with diethyl ether to provide the titled compound as the HCl salt. MS (CI) m/z 352 (M+1)⁺; ¹H NMR (300 MHz, methanol-d₄) δ ppm 8.10 (m, 1H), 8.01 (d, 1H), 7.46 (d, 1H), 7.07 (t, 1H), 4.93 (m, 1H), 4.77 (m, 1H), 4.39-4.15 (m, 3H), 3.59-3.46 (m, 4H), 3.24 (m, 1H), 2.47-2.23 (m, 4H), 2.13-2.10 (m, 4H), 1.61 (m, 3H).

Example 30

(2S,5R)-5-ethynyl-1-(N-(4-methyl-1-(3-cyano-pyridin-2-yl)piperidin-4-yl)glycyl)pyrrolidine-2-carbonitrile

Example 30A

4-Benzyloxycarbonylamino-4-methyl-piperidine-1-carboxylic acid tert-butyl ester To a solution of the 4-methyl-piperidine-1,4-dicarboxylic acid mono-tert-butyl ester (5 g, 20.6 mmol) in toluene (40 mL) at 23° C. was added triethylamine (4.3 mL, 31 mmol) and diphenylphosphoryl azide (6.1 mL, 28.0 mmol). The resulting mixture was stirred at 23° C. for 45 minutes after which benzyl alcohol (11.1 mL, 103 mmol) was added. The reaction mixture was then heated to 80° C. for 16 hours. The reaction mixture was allowed to cool to room temperature and the excess solvents were removed under reduced pressure. The crude residue was purified by chromatography (silica gel, eluting with 10% ethyl acetate/90% hexane to 30% ethyl acetate/70% hexane) to provide the titled compound (5.6 grams). MS (CI) m/z 249 (M−99)⁺; ¹H NMR (300 MHz, CDCl₃) δ ppm 7.38-7.31 (m, 5H), 5.05 (s, 2H), 4.57 (s, 1H), 3.67-3.60 (m, 2H), 3.18 (m, 2H), 1.98-1.90 (m, 2H), 1.44 (s, 9H), 1.37 (s, 3H).

Example 30B

(4-Methyl-piperidin-4-yl)-carbamic acid benzyl ester

A mixture of Example 30A (4.7 g, 13.4 mmol) in 4 M HCl in dioxane (20 mL) was stirred at 23° C. for 12 hours. The dioxane was removed under reduced pressure and the crude solid was triturated several times with diethyl ether. The resulting white solid was dried in vacuum oven overnight to afford the HCl salt of the titled compound (2.75 g). MS (CI) m/z 249 (M+1)$^+$; $^1$H NMR (300 MHz, methanol-d$_4$) δ ppm 7.37-7.29 (m, 5H), 5.05 (s, 2H), 3.19-3.07 (m, 4H), 1.76-1.70 (m, 4H), 1.37 (s, 3H).

Example 30C (5'-Cyano-4-methyl-3,4,5,6-tetrahydro-2H-(1,2')bipyridinyl-4-yl)-carbamic acid benzyl ester A solution of (4-methyl-piperidin-4-yl)-carbamic acid benzyl ester hydrochloride salt (198 mg, 0.697 mmol), 2-chloro-5-cyanopyridine (90 mg, 0.65 mmol) and diisopropylethylamine (400 μL) in dioxane (2 mL) in a sealed tube was heated to 170° C. under microwave conditions for 20 minutes. The reaction mixture was cooled, concentrated and then purified by chromatography (silica gel, eluting with 10% hexane/ethyl acetate to 60% ethyl acetate/hexane) to provide the titled compound (167 mg) as a white foam. MS (CI) m/z 380 (M+1)$^+$; $^1$H NMR (300 MHz, DMSO-d$_6$) δ ppm 8.45 (s, 1H), 7.80 (dd, 1H), 7.37 (m, 5H), 7.18 (s, 1H), 6.93 (d, 1H), 5.00 (s, 2H), 4.00-3.95 (m, 2H), 3.35-3.26 (m, 2H), 2.19-2.07 (m, 2H), 1.49-1.43 (m, 2H), 1.27 (s, 3H).

Example 30D

4-Amino-4-methyl-3,4,5,6-tetrahydro-2H-(1,2')bipyridinyl-5'-carbonitrile

A solution of (5'-cyano-4-methyl-3,4,5,6-tetrahydro-2H-(1,2')bipyridinyl-4-yl)-carbamic acid benzyl ester (93 mg) and trimethylsilyliodide (62 μL) in acetonitrile (1.5 mL) was heated to 45° C. for 20 minutes. The reaction mixture was cooled and concentrated under reduced pressure. The crude reaction mixture was purified by chromatography (silica gel, eluting with a gradient of 2% MeOH/CH$_2$Cl$_2$/0.1% NH$_4$OH to 6% MeOH/CH$_2$Cl$_2$/0.1% NH$_4$OH) to provide the titled compound (43 mg) as a yellow foam. MS (CI) m/z 217 (M+1)$^+$; $^1$H NMR (300 MHz, DMSO) δ ppm 8.44 (s, 1H), 7.77 (d, 1H), 6.91 (d, 1H), 3.86-3.78 (m, 2H), 3.59-3.55 (m, 2H), 1.48-1.38 (m, 4H), 1.08 (s, 3H).

Example 30

(2S,5R)-5-ethynyl-1-(N-(4-methyl-1-(3-cyano-pyridin-2-yl)piperidin-4-yl)glycyl)pyrrolidine-2-carbonitrile A mixture of Example 30D (60 mg, 0.31 mmol) and (2S,5R)-1-(chloroacetyl)-5-ethynylpyrrolidine-2-carbonitrile (105 mg, 0.49 mmol, Example 8D) in acetonitrile (2 mL) was stirred at 23° C. for 72 hours. The reaction mixture was concentrated under reduced pressure, and the crude residue was purified by chromatography (silica gel, eluting with 96% dichloromethane/4% methanol/0.1% ammonium hydroxide) to provide the titled compound as a white foam. MS (CI) m/z 377 (M+1)$^+$; $^1$H NMR (300 MHz, CDCl$_3$) δ ppm 8.38 (s, 1H), 7.58 (dd, 1H), 6.59 (d, 1H), 4.74 (t, 1H), 4.63-4.57 (m, 1H), 3.78-3.68 (m, 6H), 2.53 (s, 2H), 2.43-2.34 (m, 2H), 1.69-1.50 (m, 4H), 1.19 (s, 3H).

Example 31

(b 2S,5R)-5-ethynyl-1-(N-(1-(3-cyano-pyridin-3-yl)piperidin-4-yl)glycyl)pyrrolidine-2-carbonitrile Example 31A 4-Amino-3,4,5,6-tetrahydro-2H-(1,3')bipyridinyl-5'-carbonitrile Pd$_2$(dba)$_3$ (0.040 g, 0.044 mmol, XANTHPOS (0.070 g, 0.122 mmol), dioxane (5 mL), and Cs$_2$CO$_3$ (1.10 g, 3.15 mmol) were added into a dry Schlenk flask which was purged with nitrogen several times at room temperature. Then piperidin-4-yl-carbamic acid tert-butyl ester (0.50 g, 2.34 mmol) was added followed by 5-bromo-nicotinonitrile (0.52 g, 0.285 mmol) and purging again with nitrogen. The reaction mixture was heated at 100° C. for 48 hours. The reaction was then cooled to room temperature and taken up in ethyl acetate (20 mL), washed with brine (2×) and water (2×), dried over MgSO$_4$, and concentrated under reduced pressure to provide the crude product. The residue was purified by flash chromatography on silica gel eluting with 5% to 35% ethylacetate in hexane. MS (CI) m/z 303 (M+1)$^+$; $^1$H NMR (300 MHz, methanol-d$_4$) δ ppm 8.47 (d, 1H), 8.19 (m, 1H), 7.65 (d, 1H), 4.84 (m, 1H), 3.83 (m, 2H), 3.60 (m, 1H), 3.01 (t, 2H), 1.98 (m, 2H), 1.65-1.51 (m, 2H), 1.44 (s, 9H).

To a stirred solution of (5'-cyano-3,4,5,6-tetrahydro-2H-(1,3')bipyridinyl-4-yl)-carbamic acid tert-butyl ester (0.45 g, 1.49 mmol) in dioxane (3.0 mL) at room temperature was added 4M HCl in dioxane (8 mL). The reaction mixture was stirred at room temperature for 30 minutes. The reaction mixture was concentrated under reduced pressure, and the residue was treated with ether. The solid obtained by filtration provided the titled compound. MS (CI) m/z 203 (M+1)$^+$; $^1$H NMR (300 MHz, methanol-d$_4$) δ ppm 8.68 (d, 1H), 8.52 (s, 1H), 8.35 (m, 1H), 4.15-4.10 (m, 2H), 3.51-3.40 (m, 1H), 3.12 (t, 2H), 2.20-2.15 (m, 2H), 1.82-1.69 (m, 2H).

Example 31B (2S,5R)-5-ethynyl-1-(N-(1-(3-cyano-pyridin-3-yl)piperidin-4-yl)glycyl)pyrrolidine-2-carbonitrile To a stirred solution of (2S,5R)-1-(chloroacetyl)-5-ethynylpyrrolidine-2-carbonitrile (0.050 g, 0.26 mmol, Example 8D) in acetonitrile (1.5 mL), dioxane (0.1.5 mL), dimethylformamide (0.5 mL), and water (0.5 mL) at room temperature was added 4-amino-3,4,5,6-tetrahydro-2H-(1,3')bipyridinyl-5'-carbonitrile hydrochloride salt (0.028 g, 0.125 mmol) and diisopropylethylamine (0.145 mL, 0.41 mmol). The reaction mixture was stirred at room temperature for 48 hours, concentrated under reduced pressure and purified by flash chromatography on silica eluting with 5% methanol in dichloromethane. The product was mixed with 4M HCl in dioxane (4 mL) and after 0.5 hour, the solvents were removed under reduced pressure, and the residue was solidified by trituration with diethyl ether to provide the titled compound as the HCl salt. MS (CI) m/z 363 (M+1)$^+$; $^1$H NMR (300 MHz, methanol-d$_4$) δ ppm 8.48 (d, 1H), 8.19 (d, 1H), 7.66 (m, 1H), 4.81-4.72 (m, 1H), 3.88-3.86 (m, 2H), 3.80-3.60 (q, 2H), 3.09

(d, 1H), 2.97-2.88 (m, 2H), 2.80-2.71 (m, 2H), 2.46-2.26 (m, 5H), 2.04 (m, 2H), 1.54-1.44 (m, 2H).

Example 32

(2S,5R)-5-ethynyl-1-{N-(4-methyl-1-(4-methoxycarbonylbenzoyl) piperidin-4-yl)glycyl}pyrrolidine-2-carbonitrile

Example 32A 4-(4-Benzyloxycarbonylamino-4-methyl-piperidine-1-carbonyl)benzoic acid methyl ester To a stirred solution of (4-methyl-piperidin-4-yl)-carbamic acid benzyl ester hydrochloride salt (0.15 g, 0.53 mmol, Example 30B) in dichloromethane (3 mL) at room temperature was added methyl 4-chlorocarbonylbenzoate (0.125 g, 0.62 mmol) and triethylamine (0.17 mL, 1.2 mmol). The reaction mixture was stirred at room temperature for 3 hours, aqueous ammonium chloride was added, and the mixture was extracted with dichloromethane (2×). The combined organic layers were washed with 10% $KHSO_4$, sat. $NaHCO_3$, brine, dried ($MgSO_4$), and concentrated under reduced pressure to provide the titled compound. MS (CI) m/z 411 (M+1)$^+$; $^1$H NMR (300 MHz, CDCl$_3$) δ ppm 8.07 (d, 2H), 7.46 (d, 2H), 7.33 (m, 5H), 5.06 (s, 2H), 4.63 (m, 1H—NH), 4.18-4.13 (m, 2H), 3.95 (s, 3H), 3.36 (m, 2H), 2.09 (m, 2H), 1.78-1.42 (m, 2H), 1.41 (s, 3H).

Example 32B 4-(4-Amino-4-methyl-piperidine-1-carbonyl)-benzoic acid methyl ester To a stirred solution of Example 32A (0.2 g, 0.49 mmol) in acetonitrile (4.0 mL) at room temperature was added iodotrimethysilane (0.11 mL, 0.75 mmol). The reaction mixture was stirred at 50° C. for 30 minutes and then concentrated under reduced pressure. The solid residue was washed with acetone and ether and filtered to provide titled compound. MS (CI) m/z 277 (M+1)$^+$; $^1$H NMR (300 MHz, DMSO-d$_6$) δ ppm 8.04 (d, 2H), 7.90 (bs, 2H NH$_2$-DMSO solvent), 7.50 (d, 2H), 3.88 (s, 3H), 3.35-3.20 (m, 4H), 1.79-1.58 (m, 4H), 1.35 (s, 3H).

Example 32

(2S,5R)-5-ethynyl-1-{N-(4-methyl-1-(4-methoxycarbonylbenzoyl)piperidin-4-yl)glycyl}pyrrolidine-2-carbonitrile To a stirred solution of (2S,5R)-1-(chloroacetyl)-5-ethynylpyrrolidine-2-carbonitrile (0.03 g, 0.152 mmol, Example 8D) in acetonitrile (3 mL) at room temperature was added Example 32B (0.125 g, 0.31 mmol) and diisopropylethylamine (0.06 mL, 0.31 mmol). The reaction mixture was stirred at room temperature for 48 hours, concentrated under reduced pressure and purified by high pressure liquid chromatography with acetonitrile and water buffered with ammonium acetate to provide the titled compound. MS (CI) m/z 437 (M+1)$^+$; $^1$H NMR (300 MHz, CDCl$_3$) δ ppm 8.07 (d, 2H), 7.45 (d, 2H), 4.75 (m, 1H), 4.59 (m, 1H), 3.94 (s, 3H), 3.17-3.91 (m, 6H), 2.55 (bs, 1H), 2.32-2.46 (m, 5H), 1.40-1.82 (m, 4H), 1.19 (m, 3H).

Example 33

(2S,5R)-5-ethynyl-1-{N-(4-methyl-1-(4-carboxypyridin-2-yl)piperidin-4-yl)glycyl}pyrrolidine-2-carbonitrile Example 33 was prepared in the same manner as Example 40 by substituting 2-fluoroisonicotinic acid for 6-fluoronicotinic acid. MS (CI) m/z 396 (M+1)$^+$; $^1$H NMR (300 MHz, methanol-d$_4$) δ ppm 8.17 (d, 1H), 7.67 (s, 1H), 7.31 (d,d 1H), 4.84 (m, 2H), 4.34-4.15 (m, 4H), 3.41-3.35 (m, 2H), 3.20 (m, 1H), 2.52-2.24 (m, 5H), 2.07-2.00 (m, 4H), 1.59 (s, 3H).

Example 34

(2S,5R)-5-ethynyl-1-(N-{4-methyl-1-(5-(trifluoromethyl)pyridin-2-yl)piperidin-4-yl}glycyl)pyrrolidine-2-carbonitrile

Example 34A

4-Methyl-5'-trifluoromethyl-3,4,5,6-tetrahydro-2H-(1,2')bipyridinyl-4-ylamine

To a stirred solution of (4-methyl-piperidin-4-yl)-carbamic acid benzyl ester hydrochloride salt (0.15 g, 0.53 mmol, Example 30B) in dioxane (1.0 mL) at room temperature was added 2-chloro-5-trifluoromethyl-pyridine (0.11 g, 0.6 mmol) and diisopropylethyl amine (0.21 mL, 1.2 mmol). The reaction mixture was stirred at 150° C. in a microwave for 180 minutes, concentrated under reduced pressure and purified by flash chromatography with 30% ethyl acetate in hexane to provide (4-methyl-5'-trifluoromethyl-3,4,5,6-tetrahydro-2H-(1,2')bipyridinyl-4-yl)-carbamic acid benzyl ester. MS (CI) m/z 394 (M+1)$^+$; $^1$H NMR (300 MHz, CDCl$_3$) δ ppm 8.38 (d, 1H), 7.61 (d,d 1H), 7.40-7.30 (m, 5H), 6.66 (d, 1H), 5.07 (s, 2H), 4.71-4.67 (m, 1H), 3.93 (m, 2H), 3.36 (m, 2H), 2.10 (m, 2H), 1.68 (m, 2H), 1.42 (s, 3H).

To a stirred solution of (4-methyl-5'-trifluoromethyl-3,4,5,6-tetrahydro-2H-(1,2')bipyridinyl-4-yl)-carbamic acid benzyl ester (0.37 g, 0.95 mmol) in acetonitrile (4.0 mL) at room temperature was added iodotrimethysilane (0.2 mL, 0.125 mmol). The reaction mixture was stirred at 50° C. for 30 minutes, concentrated under reduced pressure and purified by flash chromatography with 2% methanol in dichloromethane to provide the titled compound. MS (CI) m/z 260 (M+1)$^+$; $^1$H NMR (300 MHz, methanol-d$_4$) δ ppm 8.31 (d, 1H), 7.67 (d,d 1H), 6.87 (d, 1H), 4.83 (m, 2H), 3.79 (m, 2H), 3.63 (m, 2H), 1.63-1.54 (m, 4H), 1.22 (s, 3H).

Example 34

(2S,5R)-5-ethynyl-1-(N-{4-methyl-1-(5-(trifluoromethyl) pyridin-2-yl)piperidin-4-yl}glycyl)pyrrolidine-2-carbonitrile To a stirred solution of (2S,5R)-1-(chloroacetyl)-5-ethynylpyrrolidine-2-carbonitrile (0.064 g, 0.325 mmol, Example 8D) in acetonitrile (3 mL) at room temperature was added 4-methyl-5'-trifluoromethyl-3,4,5,6-tetrahydro-2H-(1,2')bipyridinyl-4-ylamine (0.110 g, 0.31 mmol) and diisopropylethylamine (0.15 mL, 0.86 mmol). The reaction mixture was stirred at room temperature for 48 hours, concentrated under reduced pressure and purified by flash chromatography with 1.5% methanol:dichloromethane. The product was mixed with 4M HCl in dioxane (2 mL) and after 0.5 h, the solvent were removed under reduced pressure, and the residue was solidified by trituration with diethyl ether to provide the titled compound as the HCl salt. MS (CI) m/z 420 (M+1)$^+$; $^1$H NMR (300 MHz, CDCl$_3$) δ ppm 8.38 (d, 1H), 7.60 (dd 1H), 6.63 (d, 1H), 4.74 (m, 1H), 4.61 (m, 1H), 3.74-3.61 (m, 5H), 3.45 (m, 1H), 2.51 (bs, 1H), 2.31-2.51 (m, 4H), 1.55-1.71 (m, 4H), 1.18 (m, 3H).

Example 35

(2S,5R)-1-{N-(1-(4-chlorobenzoyl)piperidin-4-yl) glycyl}-5-ethynylpyrrolidine-2-carbonitrile Example 35A (1-(4-Chloro-benzoyl)-piperidin-4-yl)-carbamic acid tert-butyl ester To a stirred solution of piperidin-4-yl-carbamic acid tert-butyl ester (1 g, 5 mmol) and triethylamine (1.05 ml, 7.5 mmol) in THF (30 mL) at 0° C. was slowly added 4-chlorobenzoyl chloride (0.77 ml, 6 mmol). The reaction mixture was stirred from 0° C. to room temperature for 2 hours. The reaction mixture was diluted with CH$_2$Cl$_2$ and washed with water (3 times) and brine. The organic layer was dried (sodium sulfate), filtered, and concentrated under reduced pressure to provide the titled compound. MS (DCI) m/z 339 (M+H)$^+$.

Example 35B (4-Amino-piperidin-1-yl)-(4-chloro-phenyl)-methanone

To a stirred solution of (1-(4-chloro-benzoyl)-piperidin-4-yl)-carbamic acid tert-butyl ester (46 g, 0.23 mmol) in CH$_2$Cl$_2$ (0.5 mL) was added trifluoroacetic acid (0.5 ml). The reaction mixture was stirred at room temperature for ½ hour. The reaction mixture was concentrated under reduced pressure to provide the titled compound. MS (DCI) m/z 239 (M+H)$^+$.

Example 35C (2S,5R)-1-{N-(1-(4-chlorobenzoyl)piperidin-4-yl) glycyl}-5-ethynylpyrrolidine-2-carbonitrile To a stirred solution of (2S,5R)-1-(chloroacetyl)-5-propynylpyrrolidine-2-carbonitrile (0.023 g, 0.118 mmol, Example 8D) in acetonitrile (1 mL) at room temperature was added (4-amino-piperidin-1-yl)-(4-chloro-phenyl)methanone (56 mg, 0.235 mmol). The reaction mixture was stirred at room temperature for 18 hours, concentrated under reduced pressure and purified by flash chromatography with 3% methanol: dichloromethane to provide the titled compound. MS (ESI) m/z 399 (M+H)$^+$.

Example 36

(2S,5R)-1-{N-(1-(5-chloropyridin-2-yl)-4-methylpiperidin-4-yl)glycyl}-5-ethynylpyrrolidine-2-carbonitrile Example 36A 5'-Chloro-4-methyl-3,4,5,6-tetrahydro-2H-(1,2')bipyridinyl-4-ylamine To a stirred solution of (4-methyl-piperidin-4-yl)-carbamic acid benzyl ester (0.5 g, 2.02 mmol, Example 30B) in dioxane (5.0 mL) at room temperature was added 2,5-dichloro-pyridine (0.4 g, 2.79 mmol) and diisopropylethyl amine (0.2 mL, 1.1 mmol). The reaction mixture was stirred at 80° C. for 48 hours, concentrated under reduced pressure and purified by flash chromatography with 10% to 40% ethyl acetate in hexane to provide (5'-chloro-4-methyl-3,4,5,6-tetrahydro-2H-(1, 2')bipyridinyl-4-yl)-carbamic acid benzyl ester. MS (CI) m/z 360 (M+1)$^+$; $^1$H NMR (300 MHz, CDCl$_3$) δ ppm 8.01 (d, 1H), 7.49 (dd, 1H), 7.36-7.27 (m, 5H), 7.26 (m, 1H), 6.78 (d, 1H), 5.04 (s, 2H), 3.82 (m, 2H), 3.21 (m, 2H), 2.15 (m, 2H), 1.58 (m, 2H), 1.35 (s, 3H).

To a stirred solution of (5'-chloro-4-methyl-3,4,5,6-tetrahydro-2H-(1,2')bipyridinyl-4-yl)-carbamic acid benzyl ester (0.060 g, 0.17 mmol) in acetonitrile (1.0 mL) at room temperature was added iodotrimethysilane (0.04 mL, 0.25 mmol). The reaction mixture was stirred at 50° C. for 30 minutes, concentrated under reduced pressure, and purified by flash chromatography with 3% methanol in dichloromethane to provide titled compound. MS (CI) m/z 226 (M+1)$^+$.

Example 36

(2S,5R)-1-{N-(1-(5-chloropyridin-2-yl)-4-methylpiperidin-4-yl)glycyl}-5-ethynylpyrrolidine-2-carbonitrile To a stirred solution of (2S,5R)-1-(chloroacetyl)-5-ethynylpyrrolidine-2-carbonitrile (0.013 g, 0.066 mmol, Example 8D) in acetonitrile (0.75 mL) and dioxane (0.75 mL) at room temperature was added 5'-chloro-4-methyl-3,4,5,6-tetrahydro-2H-(1,2')bipyridinyl-4-ylamine (0.028 g, 0.125 mmol). The reaction mixture was stirred at 70° C. for 48 hours, concentrated under reduced pressure and purified by high pressure liquid chromatography with acetonitrile and water containing 0.02% TFA. The residue was solidified by trituration with diethyl ether to provide the titled compound as the TFA salt. MS (CI) m/z 386 (M+1)$^+$; $^1$H NMR (300 MHz, methanol-d$_4$) δ ppm 8.10 (m, 1H), 7.56 (d,d, 1H), 6.87 (d, 1H), 4.93 (m, 1H), 4.81 (m, 2H), 4.34-4.12 (m, 4H), 3.35 (m, 1H), 3.23 (d, 1H), 3.15-3.06 (m, 2H), 2.46-2.31 (m, 4H), 1.88-1.99 (m, 4H), 1.55 (m, 3H).

Example 37

(2S,5R)-5-ethynyl-1-(N-(1-pyridin-2-ylpiperidin-4-yl)glycyl)pyrrolidine-2-carbonitrile Example 37A 3,4,5,6-Tetrahydro-2H-(1,2')bipyridinyl-4-ylamine Pd$_2$(dba)$_3$ (0.040 g, 0.044 mmol), XANTHPOS (0.070 g, 0.122 mmol), dioxane (5 mL), and Cs$_2$CO$_3$ (1.10 g, 3.15 mmol) were added into a dry Schlenk flask which was purged with nitrogen several times at room temperature. Then piperidin-4-yl-carbamic acid tert-butyl ester (0.50 g, 2.34 mmol) was added followed by 2-bromopyridine (0.452 g, 0.285 mmol) and additional nitrogen purges. The reaction mixture was heated at 100° C. for 48 hours. The reaction was then cooled to room temperature, taken up in ethyl acetate (20 mL), washed with brine (2×), water (2×), dried over MgSO$_4$, and concentrated under reduced pressure. The residue was purified by flash chromatography with 5% to 35% ethyl acetate in hexane. MS (CI) m/z 278 (M+1)$^+$; $^1$H NMR (300 MHz, methanol-d$_4$) δ ppm 8.03 (d, 1H), 7.57 (t, 1H), 6.86 (d, 1H), 6.65 (t, 1H), 4.84 (m, 1H), 4.16 (m, 2H), 3.58 (m, 1H), 3.04-2.95 (m, 2H), 1.92 (m, 2H), 1.52-1.47 (m, 2H), 1.44 (s, 9H).

To a stirred solution of (3,4,5,6-tetrahydro-2H-(1,2')bipyridinyl-4-yl)-carbamic acid tert-butyl ester (0.45 g, 1.49 mmol) in dioxane (3.0 mL) at room temperature was added 4M HCl in dioxane (8 mL). The reaction mixture was stirred at room temperature 30 minutes. The reaction mixture was concentrated under reduced pressure, and the residue treated with ether. The titled compound was collected by filtration. MS (CI) m/z 203 (M+1)$^+$.

Example 37

(2S,5R)-5-ethynyl-1-(N-(1-pyridin-2-ylpiperidin-4-yl)glycyl)pyrrolidine-2-carbonitrile To a stirred solution of (2S,5R)-1-(chloroacetyl)-5-ethynylpyrrolidine-2-carbonitrile (0.027 g, 0.14 mmol. Example 8D) in acetonitrile (0.5 mL), dioxane (0.5 mL), and water (0.7 mL) at room temperature was added 3,4,5,6-tetrahydro-2H-(1,2')bipyridinyl-4-ylamine (0.028 g, 0.125 mmol) and diisopropylethylamine (0.072 mL, 0.41 mmol). The reaction mixture was stirred at room temperature for 48 hours, concentrated under reduced pressure and purified by flash chromatography with 5% methanol in dichloromethane. The product was mixed with 4M HCl in dioxane (2 mL), and after 0.5 h, the volatiles were removed under reduced pressure, and the residue was solidified by trituration with diethyl ether to provide the titled compound as the HCl salt. MS (CI) m/z 338 (M+1)$^+$; $^1$H NMR (300 MHz, methanol-d4) δ ppm 8.09 (m, 1H), 7.99 (d, 1H), 7.47 (d, 1H), 7.05 (t, 1H), 4.88 (m, 1H), 4.45-4.19 (m, 5H), 3.61-3.35 (m, 2H), 3.21 (m, 1H), 2.47-2.33 (m, 6H), 1.86-1.82 (m, 2H), 1.37-1.15 (m, 2H).

Example 38

(2S,5R)-5-ethynyl-1-(N-{4-methyl-1-(4-(trifluoromethyl)pyrimidin-2-yl)piperidin-4-yl}glycyl)pyrrolidine-2-carbonitrile

Example 38A

4-Methyl-1-(4-trifluoromethyl-pyrimidin-2-yl)-piperidin-4-ylamine

To a stirred solution of (4-methyl-piperidin-4-yl)-carbamic acid benzyl ester hydrochloride salt (0.15 g, 0.53 mmol, Example 30B) in dioxane (1.0 mL) at room temperature was added 2-chloro-4-trifluoromethyl-pyrimidine (0.1 g, 0.55 mmol) and diisopropylethyl amine (0.2 mL, 1.1 mmol). The reaction mixture was stirred at 150° C. in a microwave for 30 minutes, concentrated under reduced pressure and purified by flash chromatography with 30% ethyl acetate and hexane to provide (4-methyl-1-(4-trifluoromethyl-pyrimidin-2-yl)-piperidin-4-yl)-carbamic acid benzyl ester. MS (CI) m/z 395 (M+1)$^+$; $^1$H NMR (300 MHz, CDCl$_3$) δ ppm 8.48 (d, 1H), 7.37-7.32 (m, 5H), 6.72 (d, 1H), 5.08 (s, 2H), 4.67 (bs, 1H), 4.22 (m, 2H), 3.49 (m, 2H), 2.08 (m, 2H), 1.68-1.60 (m, 2H), 1.35 (s, 3H).

To a stirred solution of (4-methyl-1-(4-trifluoromethyl-pyrimidin-2-yl)-piperidin-4-yl)-carbamic acid benzyl ester (0.060 g, 0.17 mmol) in acetonitrile (1.0 mL) at room temperature was added iodotrimethysilane (0.04 mL, 0.25 mmol). The reaction mixture was stirred at 50° C. for 30 minutes, concentrated under reduced pressure and purified by flash chromatography with 3% methanol in dichloromethane to provide the titled compound. MS (CI) m/z 261 (M+1)$^+$; $^1$H NMR (300 MHz, methanol-d$_4$) δ ppm 8.61 (d, 1H), 6.92 (d, 1H), 4.83 (m, 2H), 4.50 (m, 2H), 3.51 (m, 2H), 1.90-1.74 (m, 4H), 1.51 (s, 3H).

Example 38

(2S,5R)-5-ethynyl-1-(N-{4-methyl-1-(4-(trifluoromethyl)pyrimidin-2-yl)piperidin-4-yl}glycyl)pyrrolidine-2-carbonitrile To a stirred solution of (2S,5R)-1-(chloroacetyl)-5-ethynylpyrrolidine-2-carbonitrile (0.04 g, 0.205 mmol, Example 8D) in acetonitrile (3 mL) at room temperature was added Example 38A (0.140 g, 0.54 mmol) and diisopropylethylamine (0.10 mL, 0.58 mmol). The reaction mixture was stirred at room temperature for 48 hours, concentrated under reduced pressure and purified by flash chromatography with 3% methanol:dichloromethane with 0.03% ammonia. The product was mixed with 4M HCl in dioxane (2 mL), and after 0.5 h, the solvent were removed under reduced pressure and the residue was solidified by trituration with diethyl ether to provide the titled compound as the HCl salt. MS (CI) m/z 421 (M+1)$^+$; $^1$H NMR (300 MHz, methanol-d$_4$) δ ppm 8.61 (d, 1H), 6.95 (d, 1H), 4.85 (m, 2H), 4.21 (q, 2H), 3.12-3.23 (m, 6H), 2.28-2.45 (m, 4H), 1.80-2.03 (m, 4H), 1.6 (m, 3H).

Example 39

(2S,5R)-5-ethynyl-1-(N-(1-isonicotinoyl-4-methylpiperidin-4-yl) glycyl)pyrrolidine-2-carbonitrile

Example 39A (4-Amino-4-methyl-piperidin-1-yl)-pyridin-4-yl-methanone

To a stirred solution of (4-methyl-piperidin-4-yl)-carbamic acid benzyl ester hydrochloride salt (0.15 g, 0.53 mmol, Example 30B) in dichloromethane (3 mL) at room temperature was added isonicotinoyl chloride (0.4 g, 2.79 mmol) and triethylamine (0.17 mL, 1.2 mmol). The reaction mixture was stirred at room temperature for 3 hours, aqueous ammonium chloride was added, and the mixture was extracted with dichloromethane (2×). Combined organic layers were washed with 10% KHSO$_4$, sat. NaHCO$_3$, and brine before drying (MgSO$_4$), and concentration under reduced pressure to provide (4-methyl-1-(pyridine-4-carbonyl)-piperidin-4-yl)-carbamic acid benzyl ester. MS (CI) m/z 354 (M+1)$^+$; $^1$H NMR (300 MHz, CDCl$_3$) δ ppm 8.69 (d, 2H), 7.40-7.31 (m, 7H), 5.06 (s, 2H), 4.15 (m, 1H), 4.62 (m, 4H), 2.12 (m, 2H), 1.77-1.45 (m, 2H), 1.42 (s, 3H).

To a stirred solution (4-methyl-1-(pyridine-4-carbonyl)-piperidin-4-yl)-carbamic acid benzyl ester (0.085 g, 0.24 mmol) in acetonitrile (2.0 mL) at room temperature was added iodotrimethysilane (0.06 mL, 0.36 mmol). The reaction mixture was stirred at 50° C. for 30 minutes and concentrated under reduced pressure. The solid residue was washed with acetone and filtered to provide titled compound. MS (CI) m/z 220 (M+1)$^+$; $^1$H NMR (300 MHz, DMSO-d$_6$) δ ppm 8.89 (d, 2H), 7.74 (d, 2H), 4.04 (m, 2H, NH2), 3.42-3.25 (m, 4H), 1.77-1.45 (m, 4H), 1.42 (s, 3H).

Example 39

(2S,5R)-5-ethynyl-1-(N-(1-isonicotinoyl-4-methylpiperidin-4-yl) glycyl)pyrrolidine-2-carbonitrile To a stirred solution of (2S,5R)-1-(chloroacetyl)-5-ethynylpyrrolidine-2-carbonitrile (0.03 g, 0.152 mmol, Example 8D) in acetonitrile (3 mL) at room temperature was added (4-amino-4-methyl-piperidin-1-yl)-pyridin-4-yl-methanone (0.110 g, 0.31 mmol) and diisopropylethylamine (0.06 mL, 0.31 mmol). The reaction mixture was stirred at room temperature for 48 hours, concentrated under reduced pressure and purified by high pressure liquid chromatography with acetonitrile and water buffered with ammonium acetate. The product was mixed with 4M HCl in dioxane (2 mL) and after 0.5 hours, the solvent were removed under reduced pressure, and the residue was solidified by trituration with ether to provide the titled compound as the HCl salt. MS (CI) m/z 380 (M+1)$^+$; $^1$H NMR (300 MHz, CDCl$_3$) δ ppm 8.69 (d, 2H), 7.27 (d, 2H), 4.78 (m, 1H), 4.59 (m, 1H), 4.01 (m, 1H), 3.2-3.75 (m, 6H), 2.62 (bs, 1H), 2.31-2.58 (m, 4H), 1.41-1.78 (m, 4H), 1.17 (m, 3H).

Example 40

(2S,5R)-5-ethynyl-1-(N-(4-methyl-1-(5-carboxy-pyridin-2-yl)piperidin-4-yl)glycyl)pyrrolidine-2-carbonitrile Example 40A 6-Fluoro-nicotinic acid tert-butyl ester To a stirred and refluxed solution of 6-fluoro-nicotinic acid (0.092 g, 6.52 mmol) in benzene and 2-methyl-propan-2-ol (2:1, 15:7 mL) was added dropwise N,N-dimethylformamide di-tert-butyl acetal (8.2 mL, 29.6 mmol). The reaction mixture was refluxed for 3 hours, cooled to room temperature and partitioned between aqueous NaHCO$_3$ and dichloromethane. The organic layer was washed with water and brine, dried (MgSO$_4$), filtered, concentrated under reduced pressure and purified by flash chromatography with 15% to 30% ethyl acetate in hexane to provide the titled compound. MS (CI) m/z 197 (M+1)$^+$; $^1$H NMR (300 MHz, CDCl$_3$) δ ppm 8.82 (d, 1H), 8.38 (m, 1H), 6.98 (d, 1H), 1.64 (s, 9H).

Example 40B

4-Amino-4-methyl-3,4,5,6-tetrahydro-2H-(1,2')bipyridinyl-5'-carboxylic acid tert-butyl ester To a stirred solution of (4-methyl-piperidin-4-yl)-carbamic acid benzyl ester (0.31 g, 1.28 mmol, Example 30B) in dioxane (5.0 mL) at room temperature was added 6-fluoro-nicotinic acid tert-butyl ester (0.21 g, 1.07 mmol). The reaction mixture was stirred at 80° C. for 18 hours, concentrated under reduced pressure and purified by flash chromatography with 10% to 30% ethyl acetate in hexane to provide 4-benzyloxycarbonylamino-4-methyl-3,4,5,6-tetrahydro-2H-(1,2')bipyridinyl-5'-carboxylic acid tert-butyl ester. MS (CI) m/z 426 (M+1)$^+$; $^1$H NMR (300 MHz, CDCl$_3$) δ ppm 8.74 (d, 1H), 7.97 (dd, 1H), 7.35 (m, 5H), 7.26 (s, 1H), 5.07 (s, 2H), 4.68 (s, 1H), 3.97 (m, 2H), 3.37 (m, 2H), 2.08 (m, 2H), 1.66 (m, 2H), 1.56 (s, 9H), 1.42 (s, 3H).

To a stirred solution of 4-benzyloxycarbonylamino-4-methyl-3,4,5,6-tetrahydro-2H-(1,2')bipyridinyl-5'-carboxylic acid tert-butyl ester (0.29 g, 0.68 mmol) in isopropanol, methanol and ethyl acetate (1:1:1, 5.0 mL) at room temperature was added ammonium formate (0.25 g, 1.07 mmol) and 10% Pd/C (25 mg) under nitrogen. The reaction mixture was stirred at 80° C. for 30 minutes, cooled, filtered through Celite, and concentrated under reduced pressure to provide the titled compound. MS (CI) m/z 292 (M+1)$^+$; $^1$H NMR (300 MHz, methanol-d$_4$) δ ppm 8.61 (d, 1H), 7.95 (d,d 1H), 6.79 (d, 1H), 4.80 (s, 2H), 3.85-3.79 (m, 2H), 3.66-3.60 (m, 2H), 1.67-1.59 (m, 4H), 1.58 (s, 9H), 1.23 (s, 3H).

Example 40

(2S,5R)-5-ethynyl-1-(N-(4-methyl-1-(5-carboxy-pyridin-2-yl)piperidin-4-yl)glycyl)pyrrolidine-2-carbonitrile To a stirred solution of (2S,5R)-1-(chloroacetyl)-5-ethynylpyrrolidine-2-carbonitrile (0.058 g, 0.30 mmol, Example 8D) in dioxane (3.0 mL) and water (1.0 mL) at room temperature was added 4-amino-4-methyl-3,4,5,6-tetrahydro-2H-(1,2')bipyridinyl-5'-carboxylic acid tert-butyl ester (0.170 g, 0.58 mmol). The reaction mixture was stirred at room temperature for 48 hours, concentrated under reduced pressure and purified by flash chromatography with 5% methanol in dichloromethane. The product was mixed with TFA in dichloromethane(1:1, 6 mL), and after 2 h, the volatiles were removed under reduced pressure. The residue was solidified by trituration with diethyl ether to provide the titled compound as the TFA salt. MS (CI) m/z 396 (M+1)$^+$; $^1$H NMR (300 MHz, methanol-d$_4$) δ ppm 8.68 (d, 1H), 8.15 (d,d, 1H), 7.03 (d, 1H), 4.84 (m, 2H), 4.47 (d, 2H), 4.32-4.14 (q, 2H), 3.31-3.25 (m, 2H), 3.20 (d, 1H), 2.51-2.23 (m, 5H), 2.06-1.93 (m, 4H), 1.59 (m, 3H).

Example 41

(2S,5R)-5-ethynyl-1-(N-(4-methyl-1-(5-cyano-pyridin-3-yl)piperidin-4-yl)glycyl)pyrrolidine-2-carbonitrile Example 41A 4-Amino-4-methyl-3,4,5,6-tetrahydro-2H-(1,3')bipyridinyl-5'-carbonitrile Pd(AcO)$_2$ (0.008 g, 0.036 mmol, BINAP (0.032 g, 0.052 mmol) toluene (3 mL), and Cs$_2$CO$_3$ (0.280 g, 0.85 mmol) were added into a dry Schlenk flask which was purged with nitrogen several times at room temperature. Then (4-methyl-piperidin-4-yl)-carbamic acid benzyl ester (0.280 g, 0.85 mmol. Example 30B) was added followed by 5-bromo-nicotinonitrile (0.280 g, 0.85 mmol), and the reaction vessel was purged with nitrogen again. The reaction mixture was heated at 100° C. for 72 hours. The reaction was then cooled to room temperature and taken up in ethyl acetate (20 mL), washed with brine (2×), water (2×), dried over MgSO$_4$, and concentrated under reduced pressure to give crude product. The residue was purified by flash chromatography with 10% to 35% ethylacetate/hexane. MS (CI) m/z 351 (M+1)$^+$.

To a stirred solution of (5'-cyano-4-methyl-3,4,5,6-tetrahydro-2H-(1,3')bipyridinyl-4-yl)-carbamic acid benzyl ester (0.051 g, 0.15 mmol) in isopropanol, (3.0 mL) at room temperature was added ammonium formate (0.050 g, 0.8 mmol) and 10% Pd/C (15 mg) under nitrogen. The reaction mixture was stirred at 90° C. for 18 hours, cooled, filtered through Celite and concentrated under reduced pressure to provide the titled compound. MS (CI) m/z 292 (M+1)$^+$; $^1$H NMR (300 MHz, methanol-d$_4$) δ ppm 8.48 (d, 1H), 8.18 (d, 1H), 7.65 (m, 1H), 3.49-3.36 (m, 2H), 3.32-3.36 (m, 2H), 1.73-1.61 (m, 4H), 1.20 (s, 3H).

Example 41B (2S,5R)-5-ethynyl-1-(N-(4-methyl-1-(5-cyano-pyridin-3-yl)piperidin-4-yl)glycyl)pyrrolidine-2-carbonitrile To a stirred solution of (2S,5R)-1-(chloroacetyl)-5-ethynylpyrrolidine-2-carbonitrile (0.013 g, 0.066 mmol, Example 8D) in acetonitrile (0.8 mL) at room temperature was added 4-amino-4-methyl-3,4,5,6-tetrahydro-2H-(1,3')bipyridinyl-5'-carbonitrile (0.028 g, 0.13 mmol). The reaction mixture was stirred at 70° C. for 48 hours, concentrated under reduced pressure and purified by flash chromatography with 2-4% methanol:dichloromethane. The product was mixed with 4M HCl in dioxane (2 mL) and after 0.5 h, the volatiles were removed under reduced pressure, and the residue was solidified by trituration with diethyl ether to provide the titled compound as the HCl salt. MS (CI) m/z 377 (M+1)$^+$; $^1$H NMR (300 MHz, methanol-$d_4$) δ ppm 8.48 (d, 1H), 8.18 (d, 1H), 7.66 (m, 1H), 5.01 (m, 1H), 4.77-5.0 (m, 2H), 3.78-3.45 (m, 4H), 3.34 (m, 1H), 3.08 (d, 1H), 2.51 (bs, 1H), 2.05-2.41 (m, 4H), 1.70-1.77 (m, 4H), 1.19 (m, 3H).

Example 42

(2S,5R)-5-ethynyl-1-(N-trans(4-hydroxycyclohexyl)glycyl)pyrrolidine-2-carbonitrile To a stirred solution of (2S,5R)-1-(chloroacetyl)-5-ethynylpyrrolidine-2-carbonitrile (0.030 g, 0.15 mmol, Example 8D) in acetonitrile (1 mL) at room temperature was added trans-4-aminocyclohexanol (35 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 276 (M+H)$^+$; $^1$H NMR (CDCl$_3$) δ 4.73 (m, 1H), 4.60 (m, 1H), 3.62 (m, 2H), 3.60 (m, 1H), 2.52 (d, 1H), 2.48 (m, 1H), 2.38 (m, 2H), 1.98 (m, 4H), 1.25 (m, 4H).

Example 43

(2S,5R)-5-ethynyl-1-(N-(4-trans{(4'-fluoro-5-(trifluoromethyl)-1,1'-biphenyl-2-yl)oxy}cyclohexyl)glycyl)pyrrolidine-2-carbonitrile

Example 43A 4-trans(2-bromo-4-trifluoromethyl-phenoxy)-cyclohexylamine

To a stirred solution of trans-4-aminocyclohexanol (115 mg, 1 mmol) in DMF (3 mL) at 0° C. was added 60% NaH in mineral oil (120 mg, 3 mmol). The reaction mixture was stirred at 0° C. for ½ hour and then 3-bromo-4-fluoro-1-trifluoromethyl benzene (0.17 ml, 1.2 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 338 (M+H)$^+$.

Example 43B (4-trans(2-bromo-4-trifluoromethyl-phenoxy)-cyclohexyl)-carbamic acid tert-butyl ester To a cold solution (0° C.) of 4-(2-bromo-4-trifluoromethyl-phenoxy)-cyclohexylamine (1 mmol) and NEt$_3$ (0.42 ml, 3 mmol) in CH$_2$Cl$_2$ (5 mL) was added (Boc)$_2$O (261 mg, 1.2 mmol) in CH$_2$Cl$_2$ (1 mL) solution via syringe. The reaction mixture was stirred from 0° C. to room temperature for 2 hours. It was diluted with CH$_2$Cl$_2$ and washed with water (2 times) and brine. The organic layer was dried (sodium sulfate), filtered, concentrated under reduced pressure and purified by flash chromatography with 30% ethyl acetate/hexane to provide the titled compound. MS (ESI) m/z 438 (M+H)$^+$.

Example 43C (4-trans(4'-fluoro-5-trifluoromethyl-biphenyl-2-yloxy)-cyclohexyl)-carbamic acid tert-butyl ester To a cold solution of (4-(2-bromo-4-trifluoromethyl-phenoxy)-cyclohexyl)-carbamic acid tert-butyl ester (219 mg, 0.5 mmol) in isopropanol (5 mL) was added 4-fluorophenyl-boronic acid (84 mg, 0.6 mmol), Pd(PPh$_3$)$_2$Cl$_2$ (35 mg, 0.05 mmol), and K$_2$CO$_3$ (207 mg, 1.5 mmol). The reaction mixture was heated to 85° C. for 3 hours. It was diluted with ethyl acetate and washed with water (2 times) and brine. The organic layer was dried (sodium sulfate), filtered, concentrated under reduced pressure and purified by flash chromatography with 30% ethyl acetate/hexane to provide the titled compound. MS (ESI) m/z 454 (M+H)$^+$.

Example 43D 4-trans(4'-fluoro-5-trifluoromethyl-biphenyl-2-yloxy)-cyclohexylamine To a solution of (4-(4'-fluoro-5-trifluoromethyl-biphenyl-2-yloxy)-cyclohexyl)-carbamic acid tert-butyl ester (139 mg, 0.31 mmol) in CH$_2$Cl$_2$ (1 mL) was added 4N HCl/dioxane (3 ml). The reaction mixture was stirred at room temperature for 3 hours and concentrated under reduced pressure to provide the titled compound. MS (ESI) m/z 354 (M+H)$^+$.

Example 43

(2S,5R)-5-ethynyl-1-(N-(4-trans{(4'-fluoro-5-(trifluoromethyl)-1,1'-biphenyl-2-yl)oxy}cyclohexyl)glycyl)pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(4'-fluoro-5-trifluoromethyl-biphenyl-2-yloxy)-cyclohexylamine (0.31 mmol) and NEt$_3$ (0.063 ml, 0.45 mmol). The reaction mixture was stirred at room temperature for 18 hours, concentrated under reduced pressure and purified by flash chromatography with 3% methanol:dichloromethane to provide the titled compound. MS (ESI) m/z 514 (M+H)$^+$; $^1$H NMR (DMSO) δ 7.58 (m, 3H), 7.43 (d, 1H), 7.25 (m, 2H), 7.15 (d, 1H), 4.98 (m, 1H), 4.85 (m, 1H), 4.35 (m, 2H), 3.87 (m, 1H), 3.14 (m, 1H), 2.29-2.45 (m, 3H); 2.15 (m, 6H), 1.60 (m, 4H).

Example 44

(2S,5R)-5-ethynyl-1-(N-{4-trans(4-(trifluoromethoxy)phenoxy)cyclohexyl}glycyl)pyrrolidine-2-carbonitrile

Example 44A 4-trans(trifluoromethoxy-phenoxy)-cyclohexylamine

To a stirred solution of trans-4-aminocyclohexanol (230 mg, 2 mmol) in DMF (10 mL) at 0° C. was added 60% NaH in mineral oil (240 mg, 6 mmol). The reaction mixture was stirred at 0° C. for ½ hour and then 1-fluoro-4-(trifluoromethoxy)benzene (432 mg, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 276 (M+H)$^+$.

Example 44

(2S,5R)-5-ethynyl-1-(N-{4-trans(4-(trifluoromethoxy)phenoxy)cyclohexyl}glycyl)pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(trifluoromethoxy-phenoxy)-cyclohexylamine (84 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 436 (M+H)$^+$; $^1$H NMR (CD$_3$OD) δ 7.19 (d, 2H), 6.99 (d, 2H), 4.32 (m, 2H), 4.18 (m, 1H), 3.21 (m, 1H), 2.44 (d, 3H), 2.27 (m, 6H); 1.67 (m, 2H); 1.55 (m, 2H), 1.37 (m, 2H).

Example 45

(2S,5R)-5-ethynyl-1-(N-(4-hydroxy-1-methylcyclohexyl) glycyl)pyrrolidine-2-carbonitrile Example 45A 4-(tert-Butyl-dimethyl-silanyloxy)-cyclohexanecarboxylic acid ethyl ester To a solution of 4-hydroxy-cyclohexanecarboxylic acid ethyl ester (10.32 g, 59.92 mmol) in dimethylformamide (50 mL) was added imidazole (8.16 g, 119.8 mmol), followed by tert-butyldimethylsilyl chloride (9.94 g, 65.9 mmol). The resulting mixture was stirred at room temperature for 16 hours. Diethyl ether was added (150 mL), and the mixture was washed with 1M HCl (150 mL). The aqueous layer was extracted with diethyl ether (150 mL). The combined organic layers were washed with 1M HCl (100 mL) and saturated sodium chloride solution (100 mL), dried over magnesium sulfate, filtered and concentrated to afford a clear oil. MS (CI) m/z 287 (M+1)$^+$ Example 45B 4-(tert-Butyl-dimethyl-silanyloxy)-cyclohexanecarboxylic acid To a solution of Example 45A (6.6 g, 23.0 mmol) in tetrahydrofuran (31 mL) and methanol (20 mL) was added lithium hydroxide monohydrate (1.93 g, 46.1 mmol). The resulting mixture was heated at 60° C. for 2 hours. The heat was removed and the reaction mixture was stirred at room temperature overnight. The solvents were removed in vacuo and the solution was neutralized with 1M HCl. Ethyl acetate (200 mL) was added and the layers were separated. The aqueous layer was further extracted with ethyl acetate (2×200 mL). The combined organic layers were dried over sodium sulfate, filtered and concentrated to give the titled compound (4.5 g). MS (CI) m/z 259 (M+1)$^+$ Example 45C 4-(tert-Butyl-dimethyl-silanyloxy)-1-methyl-cyclohexanecarboxylic acid To a cold (−78° C.) of diisopropylamine (3.44 mL, 24.5 mmol) in tetrahydrofuran (49 mL) was added n-butyl lithium (2.5 M in hexanes, 9.81 mL, 24.5 mmol) dropwise over 10 minutes. The ice bath was removed, and the reaction mixture was allowed to warm to 0° C. and then cooled back to ±78° C. A solution of Example 45B (3.3 g, 12.3 mmol) in tetrahydrofuran (10 mL) was then added. The ice bath was removed and the reaction mixture was heated at 50° C. for 2 hours. The reaction mixture was then cooled back to ±78° C. and methyl iodide (0.84 mL, 13.5 mmol) was added followed by stirring for 2 hours. The cooling bath was removed, and the reaction mixture was stirred at room temperature for 1 hour. The reaction solution was then poured into diethyl ether (200 mL) and 1M HCl (200 mL). The layers were separated and the aqueous layer was further extracted with diethyl ether (2×200 mL). The combined organic layers were dried over sodium sulfate, filtered and concentrated to a crude yellow oil. The crude oil was purified by flash chromatography with 15% ethyl acetate/84% hexane/1% methanol to afford the titled compound (2.37 g) as a light yellow oil. MS (CI) m/z 273 (M+1)$^+$.

Example 45D (4-(tert-Butyl-dimethyl-silanyloxy)-1-methyl-cyclohexyl)-carbamic acid benzyl ester To a solution of example 45C (832 mg, 3.05 mmol) and triethylamine (596 μL, 4.27 mmol) in toluene (15 mL) was added diphenylphosphoryl azide (791 μL, 3.66 mmol) via syringe. The resulting light amber solution was stirred at 23° C. for 1 hour, then benzyl alcohol (1.6 mL, 15.25 mmol) was added. The solution was then heated at 75° C. for 24 hours. The reaction mixture was cooled and the solvents removed in vacuo. The crude oil was purified by flash chromatography using a linear gradient of 95% hexane/5% ethyl acetate to 30% ethyl acetate/70% hexane to give the title compound (995 mg) as an inseparable mixture of diastereomers. MS (CI) m/z 378 (M+1)$^+$; $^1$H NMR (300 MHz, DMSO) δ ppm 7.37-7.28 (m, 10H), 6.86 (s, 1H), 6.82 (s, 1H), 4.96 (s, 2H), 4.95 (s, 2H), 3.80-3.70 (m, 2H), 3.62-3.50 (m, 2H), 2.05 (d, 2H), 1.79-1.75 (m, 2H), 1.64-1.20 (m, 8H), 1.19 (s, 3H), 1.16 (s, 3H), 0.84 (s, 9H), 0.83 (s, 9H), 0.02 (s, 12H).

Example 45E (4-Hydroxy-1-methyl-cyclohexyl)-carbamic acid benzyl ester

To a solution of example 45D (341 mg, 0.91 mmol) in tetrahydrofuran (5 mL) was added tetrabutylammonium fluoride (1 M solution in THF, 2.0 mL, 2 mmol). The resulting brown solution was stirred at room temperature for 24 hours and then concentrated in vacuo and partitioned between ethyl acetate (100 mL) and water (100 mL). The organic layer was dried over sodium sulfate, filtered and concentrated to afford a crude oil. The crude oil was purified by flash chromatography using a linear gradient of 80% hexane/20% ethyl acetate to 80% ethyl acetate/20% hexane to give the title compound (185 mg) as an inseparable mixture of diastereomers. MS (CI) m/z 264 (M+1)$^+$.

Example 45F

4-Amino-4-methyl-cyclohexanol

A mixture of example 45E (169 mg, 0.64 mmol), ammonium formate (105 mg, 1.67 mmol) and 10% palladium on carbon (7 mg) in isopropanol (5 mL) was heated at 80° C. for 1 hour. The reaction mixture was cooled and filtered through a plug of Celite. The filter pad was washed with ethyl acetate (50 mL), and the filtrate was concentrated in vacuo to afford the titled compound as an inseparable mixture of diastereomers. MS (CI) m/z 130 (M+1)$^+$; $^1$H NMR (300 MHz, CDCl$_3$) δ ppm 3.77-3.71 (m, 2H), 3.65-3.61 (m, 2H), 1.87-1.61 (m, 4H), 1.63-1.33 (m, 10H), 1.15 (s, 3H), 1.11 (s, 3H).

Example 45

(2S,5R)-5-ethynyl-1-(N-(4-hydroxy-1-methylcyclohexyl) glycyl)pyrrolidine-2-carbonitrile A mixture of example 45F (66 mg, 0.51 mmol) and example 8D (50 mg, 0.26 mmol) in acetonitrile (1 mL) was stirred at 23° C. for 48 hours. The reaction mixture was concentrated and the crude material was purified by flash chromatography using a step gradient of 3% methanol/97% dichloromethane to 5% methanol/95% dichloromethane to give the free base of the title compound (33 mg) as an inseparable mixture of diastereomers. The HCl salt was prepared by taking the free base up in diethyl ether, adding the appropriate amount of 1M HCl in diethyl ether and removing the solvent in vacuo. MS (CI) m/z 290 (M+1)$^+$; $^1$H NMR (300 MHz, MeOH-d$_4$) δ ppm 3.94-3.83 (m, 8H), 3.80-3.70 (m, 2H), 3.64-3.59 (m, 2H), 3.16 (d, 1H), 3.15 (d, 1H), 2.50-2.28 (m, 8H), 1.95-1.45 (m, 14H), 1.29 (s, 3H), 1.23 (s, 3H).

Example 46

(2S,5R)-5-ethynyl-1-{N-(1-methyl-4-trans(pyridin-3-yloxy)cyclohexyl)glycyl}pyrrolidine-2-carbonitrile Example 46A 1-Methyl-4-trans(pyridin-3-yloxy)-cyclohexylamine To a mixture of sodium hydride (46 mg, 2.0 mmol) in dimethylformamide (5 mL) at 0° C. was added example 45F (116 mg, 0.9 mmol). The resulting mixture was stirred at 23° C. for 30 minutes, then 3-fluoropyridine (73 μL, 0.85 mmol) was added. The mixture was then heated at 80° C. for 1 hour and then cooled. The reaction mixture was poured into saturated sodium bicarbonate solution (50 mL). The solution was then extracted with ethyl acetate (3×50 mL). The combined organic layers were dried over sodium sulfate, filtered and concentrated. The crude material was purified by flash chromatography using a step gradient of 2% methanol/97.9% dichloromethane/0.1% ammonium hydroxide to 6% methanol/93.9% dichloromethane/0.1% ammonium hydroxide to give the title compound (119 mg). MS (CI) m/z 207 (M+1)$^+$; $^1$H NMR (300 MHz, CDCl$_3$) δ ppm 8.31 (d, 1H), 8.19 (t, 1H), 7.19 (d, 2H), 4.41-4.36 (m, 1H), 2.05-1.90 (m, 2H), 1.76-1.70 (m, 2H), 1.50-1.38 (m, 4H), 1.20 (s, 3H).

Example 46

(2S,5R)-5-ethynyl-1-{N-(1-methyl-4-trans(pyridin-3-yloxy)cyclohexyl)glycyl}pyrrolidine-2-carbonitrile A mixture of example 46A (105 mg, 0.51 mmol) and example 8D (50 mg, 0.26 mmol) in acetonitrile (0.75 mL) was stirred at 23° C. for 48 hours. The reaction mixture was concentrated and the crude material was purified by flash chromatography using a linear gradient of 2% methanol/97.9% dichloromethane/0.1% ammonium hydroxide to 6% methanol/93.9% dichloromethane/0.1% ammonium hydroxide to give the title compound (43 mg) as its free base. The HCl salt was prepared by taking the free base up in diethyl ether, adding the appropriate amount of 1M HCl in diethyl ether and removing the solvent in vacuo. MS (CI) m/z 367 (M+1)$^+$; $^1$H NMR (300 MHz, MeOH-d$_4$) δ ppm 8.67 (d, 1H), 8.65 (d, 1H), 8.29 (dd, 1H), 8.02 (dd, 1H), 4.93 (m, 1H), 4.80-4.72 (m, 1H), 4.25 (AB quartet, 2H), 3.24 (d, 1H), 2.50-2.15 (m, 6H), 2.10-1.75 (m, 6H), 1.52 (s, 3H).

Example 47

(2S,5R)-1-(N-{4-trans((5-chloropyridin-3-yl)oxy)cyclohexyl}glycyl)-5-ethynylpyrrolidine-2-carbonitrile Example 47A 4-trans(5-chloro-pyridin-3-yloxy)cyclohexylamine To a stirred solution of trans-4-aminocyclohexanol (230 mg, 2 mmol) in DMF (5 mL) at 0° C. was added 60% NaH in mineral oil (240 mg, 6 mmol). The reaction mixture was stirred at 0° C. for ½ hour and then 3-chloro-5-fluoro-pyridine (0.21 ml, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 227 (M+H)$^+$.

Example 47

(2S,5R)-1-(N-{4-trans((5-chloropyridin-3-yl)oxy)cyclohexyl}glycyl)-5-ethynylpyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(5-chloro-pyridin-3-yloxy)cyclohexylamine (70 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 387 (M+H)$^+$; $^1$H NMR (CDCl$_3$) δ 8.17 (m, 2H), 7.19 (m, 1H), 4.74 (m, 1H), 4.59 (m, 1H), 4.24 (m, 1H), 3.63 (m, 2H), 2.61 (m, 1H), 2.53 (d, 1H), 2.40 (m, 4H), 2.15 (m, 2H), 2.04 (m, 2H), 1.54 (m, 2H), 1.33 (m, 2H).

Example 48

(2S,5R)-1-{N-(4-trans(4-cyanophenoxy)cyclohexyl)
glycyl}-5-ethynylpyrrolidine-2-carbonitrile

Example 48A 4-(4-transaminocyclohexyloxy)-benzonitrile

To a stirred solution of trans-4-aminocyclohexanol (115 mg, 1 mmol) in DMF (6 mL) at 0° C. was added 60% NaH in mineral oil (120 mg, 3 mmol). The reaction mixture was stirred at 0° C. for ½ hour and then 4-fluorobenzonitrile (151 mg, 1.25 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 217 (M+H)$^+$.

Example 48

(2S,5R)-1-{N-(4-trans(4-cyanophenoxy)cyclohexyl)
glycyl}-5-ethynylpyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(4-aminocyclohexyloxy)-benzonitrile (66 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 377 (M+H)$^+$; $^1$H NMR (DMSO) δ 7.74 (d, 2H), 7.14 (d, 2H), 4.95 (m, 1H), 4.84 (m, 1H), 4.39 (m, 1H), 3.92 (m, 1H), 3.44 (m, 2H), 3.16 (m, 1H), 2.28 (m, 2H), 2.17 (m, 6H), 2.14 (d, 1H), 1.53 (m, 4H).

Example 49

(2S,5R)-5-ethynyl-1-(N-(4-trans{(5-(trifluoromethyl)pyridin-2-yl)oxy}cyclohexyl)glycyl)pyrrolidine-2-carbonitrile

Example 49A 4-trans(5-trifluoromethyl-pyridin-2-yloxy)-cyclohexylamine

To a stirred solution of trans-4-aminocyclohexanol (345 mg, 3 mmol) in DMF (10 mL) at 0° C. was added 60% NaH in mineral oil (360 mg, 6 mmol). The reaction mixture was stirred at 0° C. for ½ hour, and then 2-chloro-5-(trifluoromethyl)pyridine (652 mg, 3.6 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 261 (M+H)$^+$.

Example 49

(2S,5R)-5-ethynyl-1-(N-(4-trans{(5-(trifluoromethyl)pyridin-2-yl)oxy}cyclohexyl)glycyl)pyrrolidine-2-carbonitrile To a stirred solution of (2S,5R)-1-(chloroacetyl)-5-propynylpyrrolidine-2-carbonitrile (0.03 g, 0.15 mmol, Example 8D) in acetonitrile (1 mL) at room temperature was added 4-(5-trifluoromethyl-pyridin-2-yloxy)-cyclohexylamine (80 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 421 (M+H)$^+$; $^1$H NMR (DMSO) δ 8.58 (m, 1H), 8.06 (m, 1H), 6.97 (d, 1H), 4.97 (m, 1H), 4.86 (m, 1H), 4.35 (m, 1H), 3.88 (m, 1H), 3.19 (m, 2H), 2.15-2.40 (m, 9H), 1.55 (m, 4H).

Example 50

(2S,5R)-5-ethynyl-1-(N-{4-trans(3-pyridin-4-yl-4-(trifluoromethyl)phenoxy)cyclohexyl}glycyl)pyrrolidine-2-carbonitrile

Example 50A 4-trans(3-bromo-4-trifluoromethyl-phenoxy)-cyclohexylamine

To a stirred solution of trans-4-aminocyclohexanol (115 mg, 1 mmol) in DMF (3 mL) at 0° C. was added 60% NaH in mineral oil (120 mg, 3 mmol). The reaction mixture was stirred at 0° C. for ½ hour and then 2-bromo-4-fluoro-1-(trifluoromethyl)benzene (0.17 ml, 1.2 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 338 (M+H)$^+$.

Example 50B (4-trans(3-bromo-4-trifluoromethyl-phenoxy)-cyclohexyl)-carbamic acid tert-butyl ester To a cold solution (0° C.) of 4-(3-bromo-4-trifluoromethyl-phenoxy)-cyclohexylamine (1 mmol) and NEt$_3$ (0.42 ml, 3 mmol) in CH$_2$Cl$_2$ (5 mL) was added (Boc)$_2$O (261 mg, 1.2 mmol) in CH$_2$Cl$_2$ (1 mL) solution via syringe. The reaction mixture was stirred from 0° C. to room temperature for 2 hours. It was diluted with CH$_2$Cl$_2$ and washed with water (2 times) and brine. The organic layer was dried (sodium sulfate), filtered, concentrated under reduced pressure and purified by flash chromatography with 30% ethyl acetate/hexane to provide the titled compound. MS (ESI) m/z 438 (M+H)$^+$.

Example 50C (4-trans(3-pyridin-4-yl-4-trifluoromethyl-phenoxy)-cyclohexyl)-carbamic acid tert-butyl ester To a solution of (4-(2-bromo-4-trifluoromethyl-phenoxy)-cyclohexyl)-carbamic acid tert-butyl ester (219 mg, 0.5 mmol) in isopropanol (3 mL) was added 4-pyridylboronic acid (74 mg, 0.6 mmol), Pd(PPh$_3$)$_2$Cl$_2$ (35 mg, 0.05 mmol), and K$_2$CO$_3$ (207 mg, 1.5 mmol). The reaction mixture was heated to 85° C. for 3 hours. It was diluted with ethyl acetate and washed with water (2 times) and brine. The organic layer was dried (sodium sulfate), filtered, concentrated under reduced pressure and purified by flash chromatography with 30% ethyl acetate/hexane to provide the titled compound. MS (ESI) m/z 437 (M+H)$^+$.

Example 50D 4-trans(3-pyridin-4-yl-4-trifluoromethyl-phenoxy)-cyclohexylamine To a solution of (4-(3-pyridin-4-yl-4-trifluoromethyl-phenoxy)-cyclohexyl)-carbamic acid tert-butyl ester (135 mg, 0.31 mmol) in CH$_2$Cl$_2$ (1 mL) was added 4N HCl/dioxane (3 ml). The reaction mixture was stirred at room temperature for 3 hours. It was concentrated under reduced pressure to provide the titled compound. MS (ESI) m/z 337 (M+H)$^+$.

Example 50

(2S,5R)-5-ethynyl-1-(N-{4-trans(3-pyridin-4-yl-4-(trifluoromethyl)phenoxy)cyclohexyl}glycyl)pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(3-pyridin-4-yl-4-trifluoromethyl-phenoxy)-cyclohexylamine (0.31 mmol) and NEt$_3$ (0.063 ml, 0.45 mmol). The reaction mixture was stirred at room temperature for 18 hours, concentrated under reduced pressure and purified by flash chromatography with 3% methanol:dichloromethane to provide the titled compound. MS (ESI) m/z 497 (M+H)$^+$; $^1$H NMR (CD$_3$OD) δ 8.94 (d, 2H), 8.10 (d, 2H), 7.85 (d, 1H), 7.31 (m, 1H), 7.08 (d, 1H), 4.94 (m, 1H), 4.85 (m, 1H), 3.18-3.25 (m, 4H), 2.20-2.50 (m, 9H), 1.65 (m, 4H).

Example 51

(2S,5R)-5-ethynyl-1-{N-(4-trans(pyridin-2-yloxy)cyclohexyl) glycyl}pyrrolidine-2-carbonitrile

Example 51A 4-trans(pyridin-2-yloxy)-cyclohexylamine

To a stirred solution of trans-4-aminocyclohexanol (230 mg, 2 mmol) in DMF (10 mL) at 0° C. was added 60% NaH in mineral oil (240 mg, 6 mmol). The reaction mixture was stirred at 0° C. for ½ hour and then 2-bromo-pyridine (0.23 ml, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 193 (M+H)$^+$.

Example 51

(2S,5R)-5-ethynyl-1-{N-(4-trans(pyridin-2-yloxy)cyclohexyl)glycyl}pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(pyridin-2-yloxy)-cyclohexylamine (60 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 353 (M+H)$^+$; $^1$H NMR (CDCl$_3$) δ 8.13 (m, 1H), 7.54 (m, 1H), 6.82 (m, 1H), 6.87 (d, 1H), 5.00 (m, 1H), 4.74 (m, 1H), 4.63 (m, 1H), 3.63 (m, 2H), 2.29-2.60 (m, 4H), 2.19 (m, 2H), 2.00 (m, 2H), 1.72 (m, 2H), 1.26-1.56 (m, 4H).

Example 52

(2S,5R)-5-ethynyl-1-{N-(1-methyl-4-trans(5-cyano-pyridin-2-yloxy)cyclohexyl)glycyl}pyrrolidine-2-carbonitrile

Example 52A 6-(4-Amino-4-transmethyl-cyclohexyloxy)-nicotinonitrile

Example 52A was prepared in the same manner as example 46A, by substituting 2-chloro-5-cyanopyridine for 3-fluoropyridine. MS (CI) m/z 232 (M+1)$^+$; $^1$H NMR (300 MHz, CDCl$_3$) δ ppm 8.45 (t, 1H), 7.75 (dd, 1H), 6.75 (d, 1H), 5.25-5.16 (m, 1H), 2.10-1.40 (m, 8H), 1.21 (s, 3H).

Example 52

(2S,5R)-5-ethynyl-1-{N-(1-methyl-4-trans(5-cyano-pyridin-2-yloxy)cyclohexyl)glycyl}pyrrolidine-2-carbonitrile Example 52 was prepared in the same manner as example 46, by substituting example 52A for example 46A. MS (CI) m/z 392 (M+1)$^+$; $^1$H NMR (300 MHz, MeOH-d$_4$) δ ppm 8.52 (d, 1H), 7.96 (dd, 1H), 6.87 (d, 1H), 5.20-5.10 (m, 1H), 4.90-4.80 (m, 1H), 4.20 (AB quartet, 2H), 3.24 (d, 1H), 2.50-2.20 (m, 6H), 2.15-1.70 (m, 6H), 1.50 (s, 3H).

Example 53

(2S,5R)-5-ethynyl-1-{N-(4-trans (pyrimidin-2-yloxy)cyclohexyl) glycyl}pyrrolidine-2-carbonitrile

Example 53A 4-trans(pyrimidin-2-yloxy)-cyclohexylamine

To a stirred solution of trans-4-aminocyclohexanol (230 mg, 2 mmol) in DMF (10 mL) at 0° C. was added 60% NaH in mineral oil (240 mg, 6 mmol). The reaction mixture was stirred at 0° C. for ½ hour and then 2-chloro-pyrimidine (275 mg, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 194 (M+H)$^+$.

Example 53

(2S,5R)-5-ethynyl-1-{N-(4-trans(pyrimidin-2-yloxy)cyclohexyl)glycyl}pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(pyrimidin-2-yloxy)-cyclohexylamine (60 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 353

(M+H)+; 1H NMR (DMSO) δ 8.58 (d, 2H), 7.09 (m, 1H), 4.91 (m, 1H), 4.75 (m, 1H), 3.57 (m, 1H), 3.52 (m, 2H), 2.20-2.38 (m, 3H); 1.91-2.13 (m, 6H), 1.45 (m, 2H), 1.20 (m, 2H).

Example 54

(2S,5R)-5-ethynyl-1-{N-(4-trans(5-cyano-pyridin-2-yloxy)cyclohexyl)glycyl}pyrrolidine-2-carbonitrile

Example 54A 6-(4-trans-aminocyclohexyloxy)-nicotinonitrile

To a stirred solution of trans-4-aminocyclohexanol (115 mg, 1 mmol) in DMF (6 mL) at 0° C. was added 60% NaH in mineral oil (120 mg, 3 mmol). The reaction mixture was stirred at 0° C. for ½ hour and then 2-chloro-5-cyanopyridine (151 mg, 1.25 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 218 (M+H)+.

Example 54

(2S,5R)-5-ethynyl-1-{N-(4-trans(5-cyano-pyridin-2-yloxy)cyclohexyl)glycyl}pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 6-(4-aminocyclohexyloxy)-nicotinonitrile (66 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 377 (M+H)+; 1H NMR (DMSO-d6) δ 8.69 (m, 1H), 8.15 (m, 1H), 6.96 (m, 1H), 4.99 (m, 1H), 4.86 (m, 1H), 4.35 (m, 1H), 3.88 (m, 1H), 3.19 (m, 2H), 2.29 (m, 2H), 2.25 (d, 1H), 2.18 (m, 6H), 1.54 (m, 4H).

Example 55

(2S,5R)-5-ethynyl-1-(N-{4-(4-trans(trifluoromethyl)phenoxy)cyclohexyl}glycyl)pyrrolidine-2-carbonitrile

Example 55A 4-trans(4-trifluoromethyl-phenoxy)-cyclohexylamine

To a stirred solution of trans-4-aminocyclohexanol (230 mg, 2 mmol) in DMF (10 mL) at 0° C. was added 60% NaH in mineral oil (244 mg, 6 mmol). The reaction mixture was stirred at 0° C. for ½ hour and then 4-fluorobenzotrifluoride (0.32 ml, 2.5 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 260 (M+H)+.

Example 55

(2S,5R)-5-ethynyl-1-(N-{4-(4-trans(trifluoromethyl)phenoxy)cyclohexyl}glycyl)pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(4-trifluoromethyl-phenoxy)-cyclohexylamine (79 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 420 (M+H)+; 1H NMR (DMSO) δ 7.62 (d, 2H); 7.15 (d, 2H), 4.96 (m, 1H), 4.86 (m, 1H), 4.39 (m, 2H), 3.90 (m, 1H), 3.18 (m, 1H), 2.52 (m, 1H), 2.29 (m, 2H), 2.19 (d, 1H), 2.15 (m, 6H), 1.50 (m, 4H).

Example 56

(2S,5R)-5-ethynyl-1-(N-{4-((5-fluoropyridin-3-yl)oxy)-1-methylcyclohexyl}glycyl)pyrrolidine-2-carbonitrile Example 56 was prepared in the same manner as example 46, by substituting 3,5-difluoropyridine for 3-fluoropyridine. MS (ESI) m/z 385 (M+H)+; 1H NMR (CDCl3) δ 8.13 (m, 1H); 8.08 (d, 1H); 6.94 (m, 1H); 4.75 (m, 1H); 4.64 (m, 1H); 4.30 (m, 1H); 3.58 (m, 2H); 2.40 (m, 4H); 1.65-2.04 (m, 7H); 1.45 (m, 2H); 1.14 (s, 3H).

Example 57

(2S,5R)-5-ethynyl-1-(N-(4-trans(4-carboxy-phenoxy)cyclohexyl) glycyl)pyrrolidine-2-carbonitrile

Example 57A 4-(4-trans-aminocyclohexyloxy)-benzoic acid tert-butyl ester

To a stirred solution of trans-4-aminocyclohexanol (345 mg, 3 mmol) in DMF (9 mL) at 0° C. was added 60% NaH in mineral oil (360 mg, 9 mmol). The reaction mixture was stirred at 0° C. for ½ hour and then tert-butyl 4-fluorobenzoate (706 mg, 3.6 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 292 (M+H)+.

Example 57B (2S,5R)-trans-4-{4-(2-(2-Cyano-5-ethynyl-pyrrolidin-1-yl)-2-oxo-ethylamino)-cyclohexyloxy}-benzoic acid tert-butyl ester To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(4-aminocyclohexyloxy)-benzoic acid tert-butyl ester (89 mg, 0.31 mmol). The reaction mixture was stirred at room temperature for 18 hours, concentrated under reduced pressure and purified by flash chromatography with 3% methanol/ 97% dichloromethane to provide the titled compound. MS (ESI) m/z 452 (M+H)$^+$; $^1$H NMR (CDCl$_3$) δ 7.91 (d, 2H), 6.86 (d, 2H), 4.74 (m, 1H), 4.60 (m, 1H), 4.28 (m, 1H), 3.64 (m, 2H), 2.32-2.59 (m, 6H), 2.17 (m, 2H), 2.04 (m, 2H), 1.24-1.54 (m, 4H).

Example 57

(2S,5R)-5-ethynyl-1-(N-(4-trans(4-carboxy-phenoxy)cyclohexyl)glycyl)pyrrolidine-2-carbonitrile To a solution of Example 57B (40 mg, 0.088 mmol) in CH$_2$Cl$_2$ (0.5 mL) was added 4N HCl/dioxane (1 ml). The reaction mixture was stirred at room temperature for 3 hours. It was concentrated under reduced pressure to provide the titled compound. MS (ESI) m/z 396 (M+H)$^+$, $^1$H NMR (MeOD) δ 7.95 (d, 2H), 6.98 (d, 2H), 4.45 (m, 1H), 4.24 (m, 2H), 3.18 (m, 2H), 2.20-2.45 (m, 6H); 1.50-1.74 (m, 4H).

Example 58

(2S,5R)-5-ethynyl-1-(N-{4-(2-(2-oxopyrrolidin-1-yl)-4-trans(trifluoromethyl)phenoxy)cyclohexyl}glycyl)pyrrolidine-2-carbonitrile Example 58A 4-trans(2-bromo-4-trifluoromethyl-phenoxy)-cyclohexylamine To a stirred solution of trans-4-aminocyclohexanol (115 mg, 1 mmol) in DMF (3 mL) at 0° C. was added 60% NaH in mineral oil (120 mg, 3 mmol). The reaction mixture was stirred at 0° C. for ½ hour and then 3-bromo-4-fluoro-1-trifluoromethyl benzene (0.17 ml, 1.2 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 338 (M+H)$^+$.

Example 58B (4-trans(2-bromo-4-trifluoromethyl-phenoxy)-cyclohexyl)-carbamic acid tert-butyl ester To a cold solution (0° C.) of 4-(2-bromo-4-trifluoromethyl-phenoxy)-cyclohexylamine (1 mmol) and NEt$_3$ (0.42 ml, 3 mmol) in CH$_2$Cl$_2$ (5 mL) was added (Boc)$_2$O (261 mg, 1.2 mmol) in CH$_2$Cl$_2$ (1 mL) solution via syringe. The reaction mixture was stirred from 0° C. to room temperature for 2 hours. It was diluted with CH$_2$Cl$_2$ and washed with water (2 times) and brine. The organic layer was dried (sodium sulfate), filtered, concentrated under reduced pressure and purified by flash chromatography with 30% ethyl acetate/hexane to provide the titled compound. MS (ESI) m/z 438 (M+H)$^+$.

Example 58C

{4-trans(3-(2-oxo-pyrrolidin-1-yl)-4-trifluoromethyl-phenoxy)-cyclohexyl}-carbamic acid tert-butyl ester To a cold solution of (4-(2-bromo-4-trifluoromethyl-phenoxy)-cyclohexyl)-carbamic acid tert-butyl ester (220 mg, 0.5 mmol) in pyridine (5 mL) was added 2-pyrrolidinone (0.08 ml, 1 mmol), Cu powder (64 mg, 1 mmol), and K$_2$CO$_3$ (414 mg, 3 mmol). The reaction mixture was heated to 85° C. for 16 hours. It was diluted with ethyl acetate and washed with water (2 times) and brine. The organic layer was dried (sodium sulfate), filtered, concentrated under reduced pressure and purified by flash chromatography with 50% ethyl acetate/ hexane to provide the titled compound. MS (ESI) m/z 444 (M+H)$^+$.

Example 58D 1-(2-(4-trans-amino-cyclohexyloxy)-5-trifluoromethyl-phenyl)-pyrrolidine-2-one To a solution of {4-(3-(2-oxo-pyrrolidin-1-yl)-4-trifluoromethyl-phenoxy)-cyclohexyl}-carbamic acid tert-butyl ester (80 mg, 0.18 mmol) in CH$_2$Cl$_2$ (1 mL) was added 4N HCl/dioxane (2 ml). The reaction mixture was stirred at room temperature for 3 hours. It was concentrated under reduced pressure to provide the titled compound. MS (ESI) m/z 344 (M+H)$^+$.

Example 58

(2S,5R)-5-ethynyl-1-(N-{4-trans-(2-(2-oxopyrrolidin-1-yl)-4-(trifluoromethyl)phenoxy)cyclohexyl}glycyl)pyrrolidine-2-carbonitrile To a stirred solution of (2S,5R)-1-(chloroacetyl)-5-ethynylpyrrolidine-2-carbonitrile (0.024 g, 0.12 mmol) in acetonitrile (1 mL) at room temperature was added 1-(2-(4-aminocyclohexyloxy)-5-trifluoromethyl-phenyl)-pyrrolidine-2-one (0.18 mmol) and NEt$_3$ (0.050 ml, 0.36 mmol). The reaction mixture was stirred at room temperature for 18 hours, concentrated under reduced pressure and purified by flash chromatography with 3% methanol:dichloromethane to provide the titled compound. MS (ESI) m/z 504 (M+H)$^+$; $^1$H NMR (CD$_3$OD) δ 7.62 (m, 1H), 7.59 (m, 1H), 7.30 (d, 1H), 4.85 (m, 1H), 4.35 (m, 1H), 3.78 (m, 2H), 3.23 (m, 1H), 3.14 (m, 1H), 2.53 (m, 2H), 2.44 (m, 2H), 2.20-2.33 (m, 7H), 1.62 (m, 4H).

Example 59

(2S,5R)-1-{N-(4-trans(4-cyano-2-methoxyphenoxy)cyclohexyl)glycyl}-5-ethynylpyrrolidine-2-carbonitrile Example 59A 4-(4-trans-amino-cyclohexyloxy)-3-methoxy-benzonitrile To a stirred solution of trans-4-aminocyclohexanol (115 mg, 1 mmol) in DMF (5 mL) at 0° C. was added 60% NaH in mineral oil (120 mg, 3 mmol). The reaction mixture was stirred at 0° C. for ½ hour and then 4-fluoro-3-methoxybenzonitrile (182 mg, 1.2 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 247 (M+H)$^+$.

Example 59

(2S,5R)-1-{N-(4-trans(4-cyano-2-methoxyphenoxy) cyclohexyl)glycyl}-5-ethynylpyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(4-amino-cyclohexyloxy)-3-methoxy-benzonitrile (75 mg, 0.31 mmol). The reaction mixture was stirred at room temperature for 18 hours, concentrated under reduced pressure and purified by flash chromatography with 3% methanol: dichloromethane to provide the titled compound. MS (ESI) m/z 407 (M+H)$^+$; $^1$H NMR (DMSO) δ 7.40 (s, 1H), 7.37 (d, 1H), 7.25 (d, 1H), 4.95 (m, 1H), 4.84 (m, 1H), 4.39 (m, 2H), 3.90 (m, 1H), 3.79 (s, 3H), 3.44 (m, 2H), 3.16 (m, 1H), 2.28 (m, 2H), 2.16 (d, 1H), 2.13 (m, 6H), 1.53 (m, 4H).

Example 60

(2S,5R)-1-(N-{4-trans ((5-chloropyridin-2-yl)oxy) cyclohexyl}glycyl)-5-ethynylpyrrolidine-2-carbonitrile

Example 60A 4-trans(5-chloro-pyridin-2-yloxy)-cyclohexylamine

To a stirred solution of trans-4-aminocyclohexanol (230 mg, 2 mmol) in DMF (10 mL) at 0° C. was added 60% NaH in mineral oil (240 mg, 6 mmol). The reaction mixture was stirred at 0° C. for ½ hour and then 2,5-dichloro-pyridine (356 mg, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 227 (M+H)$^+$.

Example 60

(2S,5R)-1-(N-{4-trans ((5-chloropyridin-2-yl)oxy) cyclohexyl}glycyl)-5-ethynylpyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 445-chloro-pyridin-2-yloxy)-cyclohexylamine (70 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 387 (M+H)$^+$; $^1$H NMR (CDCl$_3$) δ 8.07 (d, 1H), 7.49 (m, 1H); 6.63 (d, 1H), 4.93 (m, 1H), 4.74 (m, 1H), 4.62 (m, 1H), 3.63 (m, 2H); 2.31-2.59 (m, 6H); 2.15 (m, 2H), 1.71 (m, 2H); 1.30-1.54 (m, 4H).

Example 61

(2S,5R)-5-ethynyl-1-{N-(1-methyl-4-trans(pyridin-2-yloxy)cyclohexyl)glycyl}pyrrolidine-2-carbonitrile

Example 61A

1-Methyl-4-trans(pyridin-2-yloxy)-cyclohexylamine

Example 61A was prepared in the same manner as example 46A, by substituting 2-chloropyridine for 3-fluoropyridine. MS (CI) m/z 207 (M+1)$^+$.

Example 61

(2S,5R)-5-ethynyl-1-{N-(1-methyl-4-trans(pyridin-2-yloxy)cyclohexyl)glycyl}pyrrolidine-2-carbonitrile Example 61 was prepared in the same manner as example 46, by substituting example 61A for example 46A. MS (CI) m/z 367 (M+1)$^+$; $^1$H NMR (300 MHz, MeOH-d$_4$) δ ppm 8.38-8.30 (m, 2H), 7.58 (d, 1H), 7.41 (t, 1H), 5.10-4.98 (m, 1H), 4.95-4.90 (m, 1H), 4.23 (AB quartet, 2H), 3.24 (d, 1H), 2.50-2.20 (m, 6H), 2.15-1.70 (m, 6H), 1.53 (s, 3H).

Example 62

(2S,5R)-5-ethynyl-1-(N-{4-trans ((5-fluoropyridin-3-yl)oxy)cyclohexyl}glycyl)pyrrolidine-2-carbonitrile

Example 62A 4-trans(5-fluoro-pyridin-3-yloxy)cyclohexylamine

To a stirred solution of trans-4-aminocyclohexanol (460 mg, 4 mmol) in DMF (5 mL) at 0° C. was added 60% NaH in mineral oil (480 mg, 12 mmol). The reaction mixture was stirred at 0° C. for ½ hour and then 3,5-difluoro-pyridine (560 mg, 4.8 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 211 (M+H)$^+$.

Example 62

(2S,5R)-5-ethynyl-1-(N-{4-trans ((5-fluoropyridin-3-yl)oxy)cyclohexyl}glycyl)pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(5-fluoro-pyridin-3-yloxy)cyclohexylamine (65 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 371 (M+H)$^+$; $^1$H NMR (CD$_3$OD) δ 8.52 (s, 2H), 8.14 (d, 1H), 4.65 (m, 1H), 4.34 (m, 1H), 4.17 (m, 1H), 3.35 (m, 2H), 3.21 (m, 1H), 2.61-2.30 (m, 9H), 1.60-1.80 (m, 4H).

Example 63

(2S,5R)-1-(N-{4-trans ((5-bromopyridin-2-yl)oxy) cyclohexyl}glycyl)-5-ethynylpyrrolidine-2-carbonitrile

Example 63A 4-trans(5-bromo-pyridin-2-yloxy)-cyclohexylamine

To a stirred solution of trans-4-aminocyclohexanol (345 mg, 3 mmol) in DMF (10 mL) at 0° C. was added 60% NaH in mineral oil (360 mg, 9 mmol). The reaction mixture was stirred at 0° C. for ½ hour and then 5-bromo-2-chloro-pyridine (700 mg, 3.6 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 271 (M+H)+.

Example 63

(2S,5R)-1-(N-{4-trans ((5-bromopyridin-2-yl)oxy) cyclohexyl}glycyl)-5-ethynylpyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(5-bromo-pyridin-2-yloxy)-cyclohexylamine (84 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 430 (M+H)+; $^1$H NMR (CD$_3$OD) δ 8.19 (d, 1H), 7.80 (m, 1H), 6.72 (d, 1H), 4.95 (m, 1H), 4.87 (m, 1H), 3.49 (m, 1H), 3.43 (m, 2H), 3.21 (m, 1H), 2.37-2.47 (d, 3H), 2.20-2.36 (m, 6H), 1.60 (m, 4H).

Example 64

(2S,5R)-5-ethynyl-1-{N-(4-trans(pyridin-3-yloxy) cyclohexyl) glycyl}pyrrolidine-2-carbonitrile

Example 64A 4-trans(pyridin-3-yloxy)cyclohexylamine

To a stirred solution of trans-4-aminocyclohexanol (230 mg, 2 mmol) in DMF (5 mL) at 0° C. was added 60% NaH in mineral oil (240 mg, 6 mmol). The reaction mixture was stirred at 0° C. for ½ hour and then 3-fluoro-pyridine (0.21 ml, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 193 (M+H)+.

Example 64

(2S,5R)-5-ethynyl-1-{N-(4-trans(pyridin-3-yloxy) cyclohexyl)glycyl}pyrrolidine-2-carbonitrile To a stirred solution of (2S,5R)-1-(chloroacetyl)-5-ethynylpyrrolidine-2-carbonitrile (0.03 g, 0.15 mmol, Example 8D) in acetonitrile (1 mL) at room temperature was added 4-(pyridin-3-yloxy)cyclohexylamine (59 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 353 (M+H)+; $^1$H NMR (CDCl$_3$) δ 8.29 (s, 1H), 8.19 (m, 1H), 7.19 (m, 2H), 4.74 (m, 1H), 4.60 (m, 1H), 4.25 (m, 1H), 3.63 (m, 2H), 2.29-2.64 (m, 4H), 2.16 (m, 2H); 2.03 (m, 3H), 1.72 (m, 2H), 1.53 (m, 2H), 1.32 (m, 2H).

Example 65

(2S,5R)-5-ethynyl-1-(N-(1,1,3,3-tetramethylbutyl) glycyl)pyrrolidine-2-carbonitrile To a stirred solution of (2S,5R)-1-(chloroacetyl)-5-ethynylpyrrolidine-2-carbonitrile (0.04 g, 0.20 mmol, Example 8D) in acetonitrile (3 mL) at room temperature under nitrogen was added 1,1,3,3-tetramethylbutylamine (0.066 g, 0.406 mmol). The reaction mixture was stirred for two days and then concentrated under reduced pressure. The residue was flash chromatographed with 2% MeOH/CH$_2$Cl$_2$ to provide the titled compound. MS (DCI) m/z 290 (M+H)+; $^1$H NMR (300 MHz, DMSO-d$_6$) δ 1.5-2.02 (10H, m), 2.07-2.21 (2H, m), 2.45-2.50 (2H, m), 3.03-3.5 (6Hs), 3.76 (1H, d), 3.78-4.53 (2H, m), 4.53-4.55 (1H, t), 5.06 (1H, m), 5.1 (1H, m).

Example 66

(2S,5R)-1-{N-(1,1-dimethyl-2-(5-cyano-pyridin-2-yloxy)ethyl)glycyl}-5-ethynylpyrrolidine-2-carbonitrile

Example 66A 6-(2-amino-2-methyl-propoxy)-nicotinonitrile

To a solution of 2-amino-2-methyl-1-propanol (0.5 ml, 5.60 mmol), in DMF (20 mL) was added NaH 60% (0.67 g, 16.80 mmol) and then 6-chloronicotinonitrile (2.03 g, 11.22 mmol). The mixture heated to 70° C. for 2 hours and then stirred at room temperature overnight. The reaction mixture was taken up in H$_2$O and extracted with EtOAc. The organic phase was washed with water (3×), dried over Na$_2$SO$_4$ and concentrated under reduced pressure to provide the titled compound as a pale yellow solid. MS (DCI) m/z 235 (M+H)+.

Example 66

(2S,5R)-1-{N-(1,1-dimethyl-2-(5-cyano-pyridin-2-yloxy)ethyl)glycyl}-5-ethynylpyrrolidine-2-carbonitrile To a stirred solution of (2S,5R)-1-(chloroacetyl)-5-ethynylpyrrolidine-2-carbonitrile (0.05 g, 0.25 mmol, Example 8D) in acetonitrile (3 mL) at room temperature under nitrogen, was added 6-(2-amino-2-methyl-propoxy)-nicotinonitrile (0.1 g, 0.508 mmol). The reaction mixture was stirred overnight and then concentrated under reduced pressure. The residue was flash chromatographed with 2% MeOH/CH$_2$Cl$_2$ to provide the desired compound as a white solid. MS (DCI) m/z 352 (M+H)+; $^1$H NMR (300 MHz, DMSO-d$_6$) δ 2.01-2.04 (2H, m), 2.05 (2H, s), 2.07 (2H, s), 3.03 (1H, m), 3.04 (6H, s), 3.5-4.57 (2H, m), 4.57-4.58 (1H, m), 4.58-5.59 (1H, m), 7.0-7.08 (3H, m).

Example 67

(2S,5R)-1-(N-(tert-butyl)glycyl)-5-ethynylpyrrolidine-2-carbonitrile

To a stirred solution of (2S,5R)-1-(chloroacetyl)-5-ethynylpyrrolidine-2-carbonitrile (0.04 g, 0.203 mmol, Example 8D) in acetonitrile (3 mL) at room temperature under nitrogen was added tert-butylamine (0.043 ml, 0.406 mmol). The reaction mixture was stirred at ambient temperature overnight. The reaction mixture was concentrated under reduced pressure. The residue was flash chromatographed with 3% MeOH/$CH_2Cl_2$ to provide the desired compound as a pale yellow oil. MS (DCI) m/z 234 (M+H)$^+$.

The free base and 1 M HCl in ether were stirred at room temperature for 2 h and then concentrated under reduced pressure. The residue was triturated with diethyl ether to provide the desired hydrochloride salt as a white powder. $^1$H NMR (DMSO-$d_6$) (major rotamer) δ 5.20 (m, 1H), 4.86 (m, 1H), 4.33 (s, 1H), 3.78 (s, 1H), 3.76 (s, 1H), 2.45 (m, 1H), 2.26 (m, 1H), 2.31 (m, 1H), 2.13 (m, 1H), 1.33 (s, 1H).

Example 68

(2S,5R)-1-{N-(1,1-dimethyl-2-(quinolin-4-ylamino)ethyl)glycyl}-5-ethynylpyrrolidine-2-carbonitrile Example 68 was prepared using the same procedure as described for Example 155 substituting 6-chloronicotinonitrile with 4-chloroquinoline. MS (DCI/$NH_3$) m/z 376 (M+H)$^+$.

Example 69

(2S,5R)-5-ethynyl-1-{N-(2-(4-fluorophenyl)-1,1-dimethylethyl)glycyl}pyrrolidine-2-carbonitrile To a stirred solution of (2S,5R)-1-(chloroacetyl)-5-ethynylpyrrolidine-2-carbonitrile (0.05 g, 0.25 mmol, Example 8D) in acetonitrile (3 mL) at room temperature under nitrogen was added 1-(4-fluorophenyl)-2-methyl-2-propylamine (0.09 g, 0.508 mmol). The reaction mixture was stirred for two days and then concentrated under reduced pressure. The residue was flash chromatographed with 1-2% MeOH/$CH_2Cl_2$ to provide the desired compound as a white powder. MS (DCI) m/z 328 (M+H)$^+$; $^1$H NMR (300 MHz, DMSO-$d_6$) δ 2.01-2.04 (2H, m), 2.05 (2H, s), 2.07 (2H, s), 3.03 (1H, m), 3.04 (6H, s), 3.5-4.57 (2H, m), 4.57-4.58 (1H, m), 4.58-5.59 (1H, m), 7.0-7.03 (4H, m).

Example 70

(2S,5R)-1-(N-(1,1-dimethylpropyl)glycyl)-5-ethynylpyrrolidine-2-carbonitrile

To a stirred solution of (2S,5R)-1-(chloroacetyl)-5-ethynylpyrrolidine-2-carbonitrile (0.03 g, 0.152 mmol, Example 8D) in acetonitrile (3 mL) at room temperature under nitrogen was added tert-amylamine (0.027 g, 0.228 mmol). The reaction mixture was stirred for two days and then concentrated under reduced pressure. The residue was flash chromatographed with 5% MeOH/$CH_2Cl_2$ to provide the titled compound. MS (DCI) m/z 248 (M+H)$^+$.

Example 71

(2S,5R)-1-{N-(2-(1,3-benzothiazol-2-ylamino)-1,1-dimethylethyl)glycyl}-5-ethynylpyrrolidine-2-carbonitrile Example 71 was prepared using the same procedure as described for Example 155 substituting 6-chloronicotinonitrile with 2-chlorobenzothiazole. MS (DCI/$NH_3$) m/z 382 (M+H)$^+$.

Example 74

(2S,5R)-1-(N-1-adamantylglycyl)-5-ethynylpyrrolidine-2-carbonitrile

To a stirred solution of (2S,5R)-1-(chloroacetyl)-5-ethynylpyrrolidine-2-carbonitrile (0.03 g, 0.20 mmol) in acetonitrile (3 mL) at room temperature under nitrogen was added 1-adamantanamine (0.06 g, 0.408 mmol). The reaction mixture was stirred for two days and then concentrated under reduced pressure. The residue was flash chromatographed with 2% MeOH/$CH_2Cl_2$ to provide the titled compound. MS (DCI) m/z 312 (M+H)$^+$.

Example 75

(2S,5R)-1-(N-cyclohexylglycyl)-5-ethynylpyrrolidine-2-carbonitrile

To a stirred solution of (2S,5R)-1-(chloroacetyl)-5-ethynylpyrrolidine-2-carbonitrile (0.035 g, 0.178 mmol, Example 8D) in acetonitrile (3 mL) at room temperature under nitrogen was added cyclohexylamine (0.041 ml, 0.356 mmol). The reaction mixture was stirred at room temperature overnight and then concentrated under reduced pressure. The residue was flash chromatographed with 2-3% MeOH/$CH_2Cl_2$ to provide the desired compound as a pale yellow oil. MS (DCI) m/z 260 (M+H)$^+$; $^1$H NMR (300 MHz, DMSO) δ 1.5-2 (10H, m), 2.13-2.31 (2H, m), 2.41-2.48 (2H, m), 3.76 (1H, d), 3.8-4.5 (2H, m), 4.53-4.55 (1H, t), 4.9 (1H, m), 5.05 (1H, m).

Example 76

(2S,5R)-5-ethynyl-1-{N-(1-(methoxymethyl)cyclopentyl)glycyl}pyrrolidine-2-carbonitrile

Example 76A (1-hydroxymethyl-cyclopentyl)-carbamic acid benzyl ester

To a stirred solution of 1-amino-1-cyclopentanemethanol (1.15 g, 10 mmol) and $NaHCO_3$ (0.84 g, 10 mmol) in acetone (14 mL)/water (14 ml) at room temperature was added benzyl succinimidyl carbonate (2.5 g, 10 mmol). The reaction mixture was stirred at room temperature for 18 hours, concentrated under reduced pressure and purified by flash chromatography with 3% methanol:dichloromethane to provide the titled compound. MS (DCI) m/z 250 (M+H)$^+$.

Example 76B (1-methoxymethyl-cyclopentyl)-carbamic acid benzyl ester

To a cold solution (0° C.) of (1-hydroxymethyl-cyclopentyl)-carbamic acid benzyl ester (250 mg, 1 mmol) and 48% aqueous HBF₄ (0.13 ml, 1 mmol) in CH₂Cl₂ (4 mL) was added TMSCHN₂ (2N in hexane, 2 mL, 4 mmol) via syringe. The resulting mixture was stirred, at 0° C., for ½ hour followed by the addition of water (10 mL). The aqueous mixture was extracted with CH₂Cl₂ (2×50 mL), and the combined organic layers were dried (sodium sulfate), filtered, concentrated and chromatographed with 30% ethyl acetate/hexane to provide the titled compound. MS (DCI) m/e 264 (M+H)⁺.

Example 76C 1-methoxymethyl-cyclopentylamine

To a solution of (1-methoxymethyl-cyclopentyl)-carbamic acid benzyl ester (150 mg, 0.57 mmol) in MeOH (5 mL) was added HCO₂NH₄ (216 mg, 3.42 mmol), followed by Pd/C (10%, 6 mg, 0.057 mmol). The resulting mixture was heated, to 70° C., for 2 hours. The reaction mixture was filtered and concentrated to provide the titled compound. MS (DCI) m/e 130 (M+H)⁺.

Example 76

(2S,5R)-5-ethynyl-1-{N-(1-(methoxymethyl)cyclopentyl)glycyl}pyrrolidine-2-carbonitrile To a stirred solution of (2S,5R)-1-(chloroacetyl)-5-ethynylpyrrolidine-2-carbonitrile (0.018 g, 0.09 mmol, Example 8D) in acetonitrile (1 mL) at room temperature was added 1-methoxymethyl-cyclopentylamine (17 mg, 0.13 mmol). The reaction mixture was stirred at room temperature for 18 hours, concentrated under reduced pressure and purified by flash chromatography with 3% methanol:dichloromethane to provide the titled compound. MS (ESI) m/z 290 (M+H)⁺; ¹H NMR (CD₃OD) δ 4.84 (m, 2H), 3.48 (m, 2H), 3.41 (s, 3H), 3.31 (m, 2H), 2.43 (d, 1H), 2.30-2.48 (m, 4H), 1.72-1.96 (m, 8H).

Example 77

(2S,5R)-5-ethynyl-1-(N-tetrahydro-2H-pyran-4-ylglycyl)pyrrolidine-2-carbonitrile Example 77 was prepared in the same manner as Example 46, by substituting tetrahydro-pyran-4-ylamine for Example 46A. MS (CI) m/z 262 (M+1)⁺.

Example 78

(2S,5R)-5-ethynyl-1-{N-((2S)-2-hydroxycyclopentyl)glycyl}pyrrolidine-2-carbonitrile To a stirred solution of (2S,5R)-1-(chloroacetyl)-5-ethynylpyrrolidine-2-carbonitrile (0.040 g, 0.20 mmol, Example 8D) in acetonitrile (1 mL) at room temperature was added trans-2-aminocyclopentanol hydrochloride (56 mg, 0.41 mmol) and triethylamine (0.14 ml, 1.02 mmol). The reaction mixture was stirred at room temperature for 18 hours, concentrated under reduced pressure and purified by flash chromatography with 3% methanol:dichloromethane to provide the titled compound. MS (ESI) m/z 262 (M+H)⁺; ¹H NMR (MeOH) 4.79 (m, 1H), 4.17-4.40 (m, 3H), 3.18 (m, 1H), 2.48 (m, 4H); 2.00-2.30 (m, 4H), 1.80 (m, 2H), 1.66 (2H, m).

Example 79

(2S,5R)-1-(N-cyclopentylglycyl)-5-ethynylpyrrolidine-2-carbonitrile

To a stirred solution of (2S,5R)-1-(chloroacetyl)-5-ethynylpyrrolidine-2-carbonitrile (0.04 g, 0.203 mmol, Example 8D) in acetonitrile (3 mL) at ambient temperature under nitrogen was added cyclopentylamine (0.04 ml, 0.406 mmol). The reaction mixture was stirred at room temperature overnight and then concentrated under reduced pressure. The residue was flash chromatographed with 3% MeOH/CH₂Cl₂ to provide the desired compound as a pale yellow oil. MS (DCI) m/z 246 (M+H)⁺; ¹H NMR (300 MHz, DMSO) δ 1.5-2 (8H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m).

Example 80

(2S,5R)-5-ethynyl-1-{N-(1-(hydroxymethyl)cyclopentyl)glycyl}pyrrolidine-2-carbonitrile To a stirred solution of (2S,5R)-1-(chloroacetyl)-5-ethynylpyrrolidine-2-carbonitrile (0.030 g, 0.15 mmol, Example 8D) in acetonitrile (1 mL) at room temperature was added 1-amino-1-cyclopentanemethanol (35 mg, 0.31 mmol). The reaction mixture was stirred at room temperature for 18 hours, concentrated under reduced pressure and purified by flash chromatography with 3% methanol:dichloromethane to provide the titled compound. MS (ESI) m/z 276 (M+H)⁺; ¹H NMR (DMSO) δ 4.99 (m, 1H), 4.86 (t, 1H), 4.28 (m, 1H), 4.00 (m, 1H), 3.50 (d, 2H), 3.51 (m, 2H), 2.27 (m, 2H), 2.14 (m, 1H), 1.75 (m, 6H), 1.55 (m, 2H).

Example 84

(2S,5S)-1-((2S)-2-amino-2-cyclopentylethanoyl)-5-methylpyrrolidine-2-carbonitrile Example 84A 5-Methyl-pyrrolidine-1,2-dicarboxylic acid 1-tert-butyl ester 2-ethyl ester The ethyl (5S)-5-methyl-L-prolinate was prepared as the trifluoroacetic acid salt as described in Example 6 by substituting methyl magnesium bromide for ethyl magnesiumbromide. Ethyl (5S)-5-methyl-L-prolinate trifluoroacetic acid salt (18.08 mmol), triethyl amine (36.16 mmol) and DMAP (0.906 mmol) were mixed in 40 mL of dichloromethane and then cooled to 0° C. Boc₂O (19.89 mmol) was added and the mixture was stirred overnight. The mixture was then diluted with dichloromethane, washed with 1N HCl and then with saturated NaHCO₃ solution. The organic layer was dried with Na₂SO₄, and then concentrated. The crude product was purified by chromatography (silica gel, 50% then 75-80% EtOAc/hexane) to give the desired titled compound. MS (CI) m/z+ 258 (M+H)⁺. $(\alpha)^{20}_{D}=-35.9$ (c 1.45, MeOH).

Example 84B (2S,5S)-5-Methyl-pyrrolidine-1,2-dicarboxylic acid 1-tert-butyl ester Example 84A (3.69 g, 14.34 mmol) in 15 mL of EtOH was treated with 14.3 mL of 1.7 N LiOH solution at room temperature. After 4 h, the mixture was concentrated, acidified with 1N HCl and then extracted with EtOAc (3×). The combined organic extracts were dried with Na$_2$SO$_4$, and then concentrated to give the crude acid. MS (ESI) m/z 228 (M−H)⁻.

Example 84C (2S,5S)-2-Carbamoyl-5-methyl-pyrrolidine-1-carboxylic acid tert-butyl ester Example 84B (2.055 g, 8.96 mmol) and Et$_3$N (2.24 mL, 1.8 equiv.) were mixed in 15 mL of THF and then cooled to 0° C. Isobutyl chloroformate (1.51 mL, 1.3 equiv.) was added. After stirring for 35 min, 0.5 M NH$_3$ in dioxane (35.8 mL, 2 equiv.) was added. After stirring at 0° C. for 3 h, the mixture was warmed to room temperature and stirred overnight. The volatiles were evaporated, and 1N HCl was added. The mixture was extracted with EtOAc (3×). The combined organic extracts were dried with Na$_2$SO$_4$ and then concentrated. The crude product was purified by chromatography (silica gel, 50% then 75-80% EtOAc/hexane) to give the desired amide. MS (ESI) m/z 229 (M+H)⁺.

Example 84D (2S,5S)-5-Methyl-pyrrolidine-2-carboxylic acid amide trifluoroacetate Example 84C (2.03 g, 8.89 mmol) in 4 mL of CH$_2$Cl$_2$ was treated with 6 mL of TFA at room temperature. After stirring for 5 h, toluene was added to azeotrope off all the volatiles to afford the crude amine. MS (CI) m/z 129 (M+H)⁺.

Example 84E ((1S)-2-((2S,5S)-2-Carbamoyl-5-methyl-pyrrolidin-1-yl)-1-cyclopentyl-2-oxo-ethyl)-carbamic acid tert-butyl ester Example 84D (296 mg, 0.66 mmol), L-tert-butoxycarbonylamino-cyclopentyl-acetic acid dicyclohexylamine salt (308 mg, 0.726 mmol), and TBTU (275 mg, 0.858 mmol) were mixed in 2.5 ml of DMF. Then 0.275 mL of NEt$_3$ (1.98 mmol) were added. Approximately another 0.1 ml of NEt$_3$ was added until the pH of the mixture reached 6-7 (by wet pH paper). The mixture was stirred for 10 h, then purified by reverse-phase HPLC to give the desired amide (195 mg, 84%). (ESI) m/z 354 (M+H)⁺.

Example 84E ((1S)-2-((2S,5S)-2-Cyano-5-methyl-pyrrolidin-1-yl)-1-cyclopentyl-2-oxo-ethyl)-carbamic acid tert-butyl ester The dehydration of the above amide was performed in a similar manner as described in Example 6G to provide the desired nitrile. MS (ESI) m/z 336 (M+H)⁺.

Example 84

(2S,5S)-1-((2S)-2-amino-2-cyclopentylethanoyl)-5-methylpyrrolidine-2-carbonitrile The removal of Boc group was performed in a similar manner as described in Example 6 to give the title compound. $^1$H NMR (400 MHz, MeOH-d$_4$) δ 1.37 (d, J=6.75 Hz, 3H) 1.43 (m, 2H) 1.6-1.8 (m, 6H) 1.90 (m, 1H) 2.13 (ddd, J=12.12, 7.36, 4.76 Hz, 1H) 2.39 (m, 4H) 4.11 (d, J=8.29 Hz, 1H) 4.40 (m, 1H) 4.78 (t, J=8.44 Hz, 1H) ppm. MS (ESI) m/z 236 (M+H)⁺.

Example 85

(2S,5R)-1-((2S)-2-amino-2-cyclopentylethanoyl)-5-prop-1-ynylpyrrolidine-2-carbonitrile

Example 85A dimethyl (2S,5R)-5-propenyl-pyrrolidine-1,2-dicarboxylate

To a cold −45° C. solution of dimethyl (2S)-5-methoxy-pyrrolidine-1,2-dicarboxylate (10 g, 46.08 mmol, Example 1B) and trimethylsilylpropyne (14.24 ml, 92.16 mmol, 2.0 equiv) in methylene chloride (180 mL) was added a solution of tin (IV) chloride (1 M in methylene chloride, 60.0 mL, 60.0 mmol, 1.3 equiv) dropwise via an addition funnel over 30 minutes. To the dark yellow solution was added solid aluminum chloride (8.58 g, 64.52 mmol, 1.4 equiv) in one portion. The resulting mixture was allowed to warm to room temperature and stirred at room temperature for 48 hours. The reaction mixture was carefully quenched by saturated aqueous NH$_4$OH (100 mL) with ice cooling. A white precipitate formed and was removed by filtration. The crude product was obtained after concentration. The residue was chromatographed on a Biotage flash 40 M eluting with 70% hexane/30% ethyl acetate to afford the titled compound. MS (DCI/NH$_3$) m/e 226 (M+H)⁺.

Example 85B methyl (5R)-5-propenyl-L-prolinate

A solution of dimethyl (2S,5R)-5-propynyl-pyrrolidine-1,2-dicarboxylate (4.25 g, 18.90 mmol) and iodotrimethylsilane (3.23 mL, 22.7 mmol, Example 85A) in chloroform (60 mL) was heated to 65° C. for 3 hours, was cooled to room temperature, concentrated under reduced pressure and flash chromatographed with 35% ethyl acetate/65% hexane to provide the titled compound. MS (DCI/NH$_3$) m/e 168 (M+H)⁺.

Example 85C

Methyl-N-(tert-butoxycarbonyl)-cyclopentyl-L-glycyl-(5R)-5-propynyl-L-prolinate

To a solution of methyl (5R)-5-propynyl-L-prolinate (334 mg, 2 mmol), dimethylaminopyridine (244 mg, 2 mmol), N-methylmorpholine (0.33 mL, 3 mmol), and Boc-cyclopentyl-L-glycine.dicyclohexylamine (1.02 g, 2.4 mmol) in dichloromethane (10 mL) at room temperature was added 1-(3-dimethylaminopropyl)-3-ethylcarbodiimide hydrochloride (383 g, 2.4 mmol). The resulting mixture was stirred 16 hours at room temperature, and partitioned between ethyl acetate (100 mL) and 1 M HCl (20 mL). The aqueous layer was further extracted with ethyl acetate (100 mL). The combined organic layers were dried (sodium sulfate), filtered, and concentrated. The residue was chromatographed with 70% ethyl acetate/hexane provide the titled compound (67%). MS (ESI) m/e 393 (M+H)⁺.

Example 85D

N-(tert-butoxycarbonyl)-cyclopentyl-L-glycyl-(5R)-5-propynyl-L-proline

To a solution of methyl N-(tert-butoxycarbonyl)-cyclopentyl-L-glycyl-(5R)-5-propynyl-L-prolinate (1.34 g, 3.42 mmol) in THF (10 mL)/water (5 ml) at room temperature was added lithium hydroxide (358 mg, 7.52 mmol). The resulting mixture was stirred at room temperature for 6 hours. The reaction was diluted with 1 M HCl solution, and the aqueous mixture was extracted with ethyl acetate (3×10 mL). The combined organic layers were dried (sodium sulfate), filtered, and concentrated to provide the titled compound. MS (ESI) m/e 379 (M+H)$^+$.

Example 85E

N-(tert-butoxycarbonyl)-cyclopentyl-L-glycyl-(5R)-5-propynyl-L-prolinamide

To a cold (0° C.) solution of N-(tert-butoxycarbonyl)-cyclopentyl-L-glycyl-(5R)-5-propynyl-L-proline (3.42 mmol) and N-methyl morpholine (0.44 mL, 3.94 mmol) in THF (15 mL) was added isobutyl chloroformate (0.56 mL, 4.26 mmol). The resulting cloudy white mixture was stirred at 0° C. for 30 minutes followed by the addition of a solution of ammonia (0.5 Min dioxane, 19.7 mL, 9.84 mmol). The solution was allowed to warm to room temperature and stirred for 16 hours. The reaction mixture was diluted by the addition of 1 M HCl (50 mL), and extracted with ethyl acetate (3×100 mL). The combined organic layers were dried (sodium sulfate), filtered, and concentrated to provide the crude compound. The residue was chromatographed with 95% $CH_2Cl_2$/MeOH to provide the titled compound. MS (ESI) m/e 378 (M+H)$^+$.

Example 85F

N-(tert-butoxycarbonyl)-cyclopentyl-L-glycyl-(5R)-5-propynyl-L-pyrrolidine-2-carbonitrile To a cold solution (−35° C.) of N-(tert-butoxycarbonyl)-cyclopentyl-L-glycyl-(5R)-5-propynyl-L-prolinamide (280 mg, 0.743 mmol) and imidazole (51 mg, 0.743 mmol) in pyridine (6 mL) was added $POCl_3$ (0.14 mL, 1.49 mmol) via syringe. The resulting mixture was stirred, maintaining the temperature below −20° C., for 1 hour followed by the addition of 1 M HCl (10 mL). The aqueous mixture was extracted with ethyl acetate (3×50 mL), and the combined organic layers were dried (sodium sulfate), filtered, concentrated and chromatographed with 30% ethyl acetate/hexane to provide the titled compound. MS (ESI) m/e 348 (M+H)$^+$; $^1$H NMR (300 MHz, $CDCl_3$) δ ppm 5.15 (t, 1H), 4.95 (d, 1H), 4.71 (t, 1H), 4.53 (ddd, 1H), 2.50 (d, 1H), 2.50-2.28 (m, 4H), 1.75-1.57 (m, 3H).

Example 85

(2S,5R)-1-((2S)-2-amino-2-cyclopentylethanoyl)-5-prop-1-ynylpyrrolidine-2-carbonitrile To a solution of N-(tert-butoxycarbonyl)-cyclopentyl-L-glycyl-(5R)-5-propynyl-L-pyrrolidine-2-carbonitrile (490 mg) in ether (1 mL) was added 4 M HCl in dioxane (8 mL). The resulting mixture was stirred at room temperature for 2 hours and the solvents removed under reduced pressure. The white solid was triturated with ether to provide the titled compound. MS (ESI) m/e 260 (M+H)$^+$; $^1$H NMR (DMSO) δ ppm 5.16 (m, 1H), 4.73 (m, 1H), 4.04 (m, 1H), 3.42 (m, 1H), 2.03-2.47 (m, 4H), 1.85 (d, 3H), 1.39-1.70 (8H, m).

Example 86

(2S,5R)-5-prop-1-ynyl-1-(N-{4-(4-(trifluoromethyl)phenoxy)cyclohexyl}glycyl)pyrrolidine-2-carbonitrile To a stirred solution of (2S,5R)-1-(chloroacetyl)-5-propynylpyrrolidine-2-carbonitrile (0.030 g, 0.15 mmol, Example 88D) in acetonitrile (1 mL) at room temperature was added 4-(4-trifluoromethyl-phenoxy)-cyclohexylamine (79 mg, 0.31 mmol, Example 55A). The reaction mixture was stirred at room temperature for 18 hours, concentrated under reduced pressure and purified by flash chromatography with 3% methanol:dichloromethane to provide the titled compound. MS (ESI) m/z 434 (M+H)$^+$; $^1$H NMR (DMSO) δ ppm 7.63 (d, 2H), 7.15 (d, 2H), 4.86 (m, 1H), 4.20-4.41 (m, 2H), 3.94 (m, 1H), 2.09-2.43 (m, 8H), 1.88 (d, 3H), 1.41-1.65 (m, 4H).

Example 87

(2S,5R)-1-{N-(1-(hydroxymethyl)cyclopentyl)glycyl}-5-prop-1-ynylpyrrolidine-2-carbonitrile To a stirred solution of (2S,5R)-1-(chloroacetyl)-5-propynylpyrrolidine-2-carbonitrile (0.03 g, 0.14 mmol, Example 88D) in acetonitrile (1 mL) at room temperature was added 1-amino-1-cyclopentanemethanol (35 mg, 0.28 mmol). The reaction mixture was stirred at room temperature for 18 hours, concentrated under reduced pressure and purified by flash chromatography with 3% methanol/97% dichloromethane to provide the titled compound. MS (ESI) m/z 290 (M+H)$^+$; $^1$H NMR (DMSO) δ ppm 4.86 (m, 1H), 4.16 (m, 1H), 3.52 (m, 2H), 3.44 (m, 2H), 2.06-2.39 (m, 4H), 1.96 (m, 2H), 1.86 (d, 3H), 1.75 (m, 6H), 1.56 (m, 2H).

Example 88

(2S,5R)-1-(N-cyclopentylglycyl)-5-prop-1-ynylpyrrolidine-2-carbonitrile

Example 88A methyl (5R)-1-(chloroacetyl)-5-propynyl-L-prolinate

To a stirred solution of methyl (5R)-5-propynyl)-L-prolinate (1.5 g, 8.98 mmol, Example 85B) and triethylamine (1.87 mL, 13.47 mmol) in dry tetrahydrofuran (20 mL) at 0° C. was gradually added chloroacetyl chloride (0.86 mL, 10.78 mmol). After stirring at room temperature for 2 hours, the mixture was filtered. The solid cake was washed with THF, and the filtrate and washings were combined, dried over sodium sulfate and concentrated under reduced pressure. The residue taken up in toluene and concentrated to dryness under reduced pressure to provide the titled compound. MS (DCI) m/z 244 (M+H)$^+$.

Example 88B (5R)-1-(chloroacetyl)-5-propynyl-L-proline

To a stirred solution of methyl (5R)-1-(chloroacetyl)-5-propynyl)-L-prolinate (1.26 g, 5.19 mmol) in THF (12 mL)

and H₂O (6 mL) at room temperature was added LiOH.H₂O (326 mg, 7.78 mmol). The reaction mixture was stirred at ambient temperature overnight and concentrated under reduced pressure. The reaction mixture was acidified to pH ~3 by adding 1M HCl dropwise. The solution was extracted with ethyl acetate (3×). Combined ethyl acetate layers were washed with brine, dried (Na₂SO₄), filtered and concentrated under reduced pressure to provide the titled compound. MS (DCI) m/z 230 (M+H)⁺.

Example 88C (5R)-1-(chloroacetyl)-5-propynyl-L-prolinamide

To a stirred solution of (5R)-1-(chloroacetyl)-5-propynyl-L-proline (1.10 g, 4.8 mmol) in CH₂Cl₂ (24 mL) at −15° C. under nitrogen was added 4-methylmorpholine (0.64 mL, 5.76 mmol), and then isobutyl chloroformate (0.81 mL, 6.24 mmol) over 10 minutes. A white precipitate formed. The reaction mixture was stirred at −15° C. under nitrogen for 30 minutes, and a solution of NH₃ in dioxane (0.5 M, 29 mL, 14.4 mmol) was added. The reaction mixture was stirred at −15° C. for 30 minutes, warmed to room temperature, and stirred at that temperature for 16 hours. The reaction mixture was diluted with 1M HCl to pH 4 and extracted with ethyl acetate (3×). The extracts were combined, washed with brine, dried (Na₂SO₄), filtered and concentrated under reduced pressure. Purification by flash column chromatography (60-75% ethyl acetate/hexane) provided the titled compound. MS (DCI) m/z 229 (M+H)⁺.

Example 88D (2S,5R)-1-(chloroacetyl)-5-propynylpyrrolidine-2-carbonitrile

To a stirred solution of (5R)-1-(chloroacetyl)-5-propynyl-L-prolinamide (0.28 g, 1.23 mmol) and imidazole (0.084 g, 1.23 mmol) in dry pyridine (6 mL) at −35° C. under nitrogen was added POCl₃ (0.23 mL, 2.46 mmol) dropwise. The reaction mixture was stirred between −35° C. to −15° C. for 1 hour and evaporated. The residue was diluted with dichloromethane and washed with H₂O (2×), dried (Na₂SO₄), filtered and concentrated under reduced pressure. Purification by flash chromatography (10% ethyl acetate/hexane) provided the titled compound. MS (DCI) m/z 211 (M+H)⁺.

Example 88

(2S,5R)-1-(N-cyclopentylglycyl)-5-prop-1-ynylpyrrolidine-2-carbonitrile

To a stirred solution of (2S,5R)-1-(chloroacetyl)-5-propynylpyrrolidine-2-carbonitrile (0.018 g, 0.086 mmol) in acetonitrile (1 mL) at room temperature was added cyclopentyl amine (0.017 mL, 0.17 mmol). The reaction mixture was stirred at room temperature for 18 hours, concentrated under reduced pressure and purified by flash chromatography with 3% methanol/97% dichloromethane to provide the titled compound. MS (ESI) m/z 260 (M+H)⁺; ¹H NMR (DMSO) δ ppm 4.89 (m, 1H), 4.84 (m, 1H), 4.07-4.13 (m, 2H), 3.52 (m, 1H), 2.05-2.42 (m, 4H), 1.96 (m, 2H), 1.87 (d, 3H), 1.70 (m, 4H), 1.52 (m, 2H).

Example 91

(2S,5S)-1-(N-cyclopentylglycyl)-5-methylpyrrolidine-2-carbonitrile

Example 91A (2S,5S)-1-(2-Chloro-acetyl)-5-methyl-pyrrolidine-2-carboxylic acid amide (2S,5S)-5-Methyl-pyrrolidine-2-carboxylic acid amide trifluoroacetate (2.0 g, 8.2 mmol, Example 84D) and triethyl amine (1.9 mL, 24.6 mmol) were dissolved in CH₂Cl₂ (6 mL), and the mixture was cooled to 0° C. Chloroacetyl chloride (0.39 mL, 9.0 mmol) was added slowly via syringe. After 2 h, saturated NaHCO₃ was added, and the mixture was extracted with EtOAc (3×). The combined organic extracts were dried (Na₂SO₄), concentrated and purified by flash chromatography (10% MeOH/EtOAc) to give the title compound. MS (DCI) m/z 205 (M+H)⁺.

Example 91B (2S,5S)-1-(2-Chloro-acetyl)-5-methyl-pyrrolidine-2-carbonitrile (2S,5S)-1-(2-Chloro-acetyl)-5-methyl-pyrrolidine-2-carboxylic acid amide (0.25 g, 1.2 mmol) and imidazole (85 mg, 1.25 mmol) ware mixed in pyridine (5 mL). The mixture was cooled to −35° C. and POCl₃ (0.18 mL, 1.8 mmol) was added slowly. The mixture was stirred at −35° C. for 1 h. Saturated NH₄Cl (20 mL) was added, and the mixture was extracted with EtOAc (3×). The combined organic layers were dried (Na₂SO₄), filtered and concentrated under reduced pressure. The oil was purified by flash chromatography (hexane:EtOAC, 2:1) to yield the title compound. MS (DCI) m/z 187 (M+H)⁺.

Example 91

(2S,5S)-1-(N-cyclopentylglycyl)-5-methylpyrrolidine-2-carbonitrile (2S,5S)-1-(2-Chloro-acetyl)-5-methyl-pyrrolidine-2-carbonitrile (50 mg, 0.30 mmol) and cyclopentylamine (0.059 mL, 0.6 mmol) were dissolved in acetonitrile (2 mL) and stirred overnight. The product was purified by reverse phase HPLC eluting with 0% to 70% acetonitrile/0.1% aqueous trifluoroacetic acid. ¹H NMR (300 MHz, methanol-d₄) δ ppm 1.36 (d, J=6.44 Hz, 3H), 1.68 (m, 5H), 1.85 (m, 3H), 2.16 (m, 3H), 2.38 (m, 3H), 3.60 (m, 1H), 4.20 (m, 1H), 4.77 (m, 1H). MS (ESI) m/z 236 (M+H)⁺.

Example 92

(2S,5S)-4,4-difluoro-5-methyl-1-L-valylpyrrolidine-2-carbonitrile

This compound was prepared from 51 mg (0.23 mmol) of (S)—N-tert-butoxycarbonylvaline and 50 mg (0.23 mmol) of (2,5-cis) 4,4-difluoro-5-methyl-pyrrolidine-2-carboxylic acid methyl ester hydrochloride (Example 95G) according to the same five step sequence as for (2S,5S)-4,4-difluoro-1-L-leucyl-5-methylpyrrolidine-2-carbonitrile (example 95H through example 95L) to give the titled compound as a colorless foam. ¹H NMR (500 MHz, DMSO-d₆) (mixture of rotamers, major rotamer only) δ ppm 0.99 (m, 6H) 1.37 (m, 3H) 2.11 (m, 1H) 2.96 (m, 1H) 3.09 (m, 1H) 4.09 (bs, 1H) 4.65 (m, 1H) 5.06 (t, J=8.6 Hz, 1H) 8.31 (bs, 3H) MS (ESI) m/z=246 (M+H)+.

Example 94

(2S,5S)-1-{N-(1-(hydroxymethyl)cyclopentyl)glycyl}-5-methylpyrrolidine-2-carbonitrile The title compound was prepared using the conditions described in Example 91 substituting 1-amino-1-cyclopentanemethanol for cyclopentylamine. $^1$H NMR (300 MHz, methanol-$d_4$) δ ppm 1.38 (d, J=6.44 Hz, 3H), 1.80 (m, 8H), 2.32 (m, 2H), 3.29 (m, 4H), 3.62 (s, 2H), 3.96 (m, 1H), 4.20 (m, 1H), 4.77 (m, 1H). MS (ESI) m/z 266 (M+H)+.

Example 95

(2S,5S)-4,4-difluoro-1-L-leucyl-5-methylpyrrolidine-2-carbonitrile

Example 95A

Dibenyzyl fumarate

To 13.92 g (120 mmol) of fumaric acid was added 250 mL of toluene and 41.8 mL (240 mmol) of N,N-diethylisopropylamine. The mixture was stirred until only a small amount of solid was present, then 28.5 mL (240 mmol) of benzyl bromide was added. The reaction was stirred at 80° C. for 5 h, then it was cooled and extracted with water (1×50 mL), 1M HCl$_{(aq.)}$(2×50 mL), saturated NaHCO$_{3(aq)}$, and brine (1×50 mL), dried over MgSO$_4$, filtered, and concentrated to a solid. This was recrystallized from 75 mL of hexanes to give the titled compound as colorless crystals. $^1$H NMR (300 MHz, DMSO-$d_6$) δ ppm 5.24 (s, 4H) 6.86 (s, 2H) 7.38 (m, 10H).

Example 95B (R)—N-tert-butoxycarbonylalanine benzyl ester

To a solution of 11.19 g (59.1 mmol) of (R)—N-tert-butoxycarbonylalanine in 70 mL of N,N-dimethylformamide was added 6.7 g (48.5 mmol) of K$_2$CO$_3$, and 6.9 mL (58.0 mmol) of benzyl bromide. The reaction was stirred at 80° C. for 40 min, then poured into 350 mL of H$_2$O. The aqueous mixture was extracted with diethyl ether (3×50 mL), then the combined ether layers were back extracted with H$_2$O (2×50 mL), and brine (1×50 mL), dried over MgSO$_4$, filtered, and concentrated in vacuo to furnish the titled compound as a colorless oil. MS (ESI) m/z=280 (M+H)+, 297 (M+NH$_4$)+, 302 (M+Na)+: $^1$H NMR (300 MHz, DMSO-$d_6$) δ ppm 1.25 (d, J=7.5 Hz, 3H) 1.37 (s, 9H) 4.06 (m, 1H) 5.07 (d, J=12.9 Hz, 1H) 5.15 (d, J=12.5 Hz, 1H) 7.34 (m, 6H).

Example 95C

5-Methyl-4-oxo-pyrrolidine-1,2,3-tricarboxylic acid 2,3-dibenzyl ester 1-tert-butyl ester To a solution of 5.59 g (20.0 mmol) of (R)—N-tert-butoxycarbonylalanine benzyl ester and 5.92 g (20.0 mmol) of dibenzyl fumarate in 60 mL of toluene was added 1.60 g (40 mmol) of 60% NaH in mineral oil. The reaction was stirred at ambient temperature under N$_2$ for 24 h, then diluted with 300 mL of diethyl ether. The solution was extracted with 1M HCl$_{(aq.)}$(1×50 mL), saturated NaHCO$_{3(aq)}$ (3×50 mL), and brine (1×50 mL), dried over MgSO$_4$, filtered, and concentrated to provide the titled compound as an oil.

Example 95D

5-Methyl-4-oxo-pyrrolidine-1,2-dicarboxylic acid 1-tert-butyl ester

To a suspension of 600 mg of 10% Pd—C in 25 mL of 2-propanol was added a solution of 8.9 g of crude 5-methyl-4-oxo-pyrrolidine-1,2,3-tricarboxylic acid 2,3-dibenzyl ester 1-tert-butyl ester in 100 mL of 2-propanol. The reaction was shaken under 60 psi of H$_2$ for 1.5 h, then filtered and concentrated to an oil. This was taken up in 20 mL of 2M NaOH$_{(aq.)}$ and extracted with diethyl ether (3×15 mL) to remove the mineral oil introduced in the previous step. The ether layers were set aside, and the aqueous layer was cooled with an ice bath, then acidified with 10 mL of 6M HCl$_{(aq.)}$. The suspension was extracted with diethyl ether (3×15 mL), then the ether layers were extracted with brine (1×15 mL), dried over MgSO$_4$, filtered, and concentrated to an oil.

Example 95E

5-Methyl-4-oxo-pyrrolidine-1,2-dicarboxylic acid 1-tert-butyl ester 2-methyl ester To a solution of 3.0 g of crude 5-methyl-4-oxo-pyrrolidine-1,2-dicarboxylic acid 1-tert-butyl ester in 25 mL of N,N-dimethylformamide was added 1.2 g (8.7 mmol) of K$_2$CO$_3$, and 1.2 mL (19.3 mmol) of methyl iodide. The mixture was stirred at 80° C. for 20 min, cooled to ambient temperature, then diluted with 125 mL of 0.2M HCl$_{(aq.)}$. This was extracted with diethyl ether (3×20 mL), then the combined ether layers were extracted with water (1×20 mL), and brine (1×20 mL), dried over MgSO$_4$, filtered, and concentrated to an oil. The product was purified via silica gel chromatography, eluting with 20% ethyl acetate/hexanes to give the 2,5-cis isomer. The 2,5-trans isomer eluted slightly faster than the desired cis isomer. $^1$H NMR (300 MHz, DMSO-$d_6$) δ ppm 1.30 (d, J=7.1 Hz, 3H) 1.40 (m, 9H) 2.59 (dd, J=19.2, 3.2 Hz, 1H) 3.12 (dd, J=18.3, 11.2 Hz, 1H) 3.66 (s, 3H) 3.92 (q, J=6.8 Hz, 1H) 4.63 (dd, J=10.7, 3.6 Hz, 1H), NOE observed between H-2 and H-5, not observed in the corresponding trans isomer; MS (ESI) m/z=256 (M−H)+.

Example 95F (2,5-cis) 4,4-Difluoro-5-methyl-pyrrolidine-1,2-dicarboxylic acid 1-tert-butyl ester 2-methyl ester To a solution of 710 mg (2.76 mmol) of (2,5-cis)-5-methyl-4-oxo-pyrrolidine-1,2-dicarboxylic acid 1-tert-butyl ester 2-methyl ester in 10 mL of CH$_2$Cl$_2$ at −78° C. was added 800 μL (6.05 mmol) of N,N-diethylaminosulfur trifluoride (DAST). The reaction was put under N$_2$, warmed to ambient temperature, and stirred for 18 h. The excess DAST was quenched by slowly adding the reaction mixture to 20 mL of ice cooled saturated NaHCO$_{3(aq)}$. After vigorously stirring the biphasic mixture for 10 min, the layers were separated. The aqueous layer was extracted with CH$_2$Cl$_2$ (1×10 mL), then the combined organic layers were back extracted with brine (1×10 mL), dried over MgSO$_4$, filtered, and concentrated to an oil. The product was purified via silica gel chromatography, (75 mL silica gel) eluting with 10% ethyl acetate/hexanes, then stepping to 20% ethyl acetate/hexanes after collection of the forerun to give the titled compound as a colorless oil. $^1$H NMR (300 MHz, CDCl$_3$) δ ppm 1.35 (dd, J=6.78, 3.05 Hz, 3H) 1.49 (s, 9H) 2.37 (m, 1H) 2.65 (m, 1H) 3.76 (m, 3H) 4.09 (bs, 1H) 4.36 (bs, 1H); MS (ESI) m/z=280 (M+H)$^+$, 297 (M+NH$_4$)$^+$, 302 (M+Na)$^+$.

Example 95G (2,5-cis) 4,4-Difluoro-5-methyl-pyrrolidine-2-carboxylic acid methyl ester hydrochloride To 363 mg (1.30 mmol) of 2,5 cis-difluoro-5-methyl-pyrrolidine-1,2-dicarboxylic acid 1-tert-butyl ester 2-methyl ester was added 3 mL of 4M HCl in dioxane. The solution was stirred at ambient temperature for 2 h, then concentrated in vacuo to furnish the titled compound as a white solid. $^1$H NMR (300 MHz, DMSO-d$_6$) δ ppm 1.34 (dd, J=7.0, 1.5 Hz, 3H) 2.72 (m, 1H) 2.91 (m, 1H) 3.78 (s, 3H) 3.93 (m, 1H) 4.76 (t, J=9.3 Hz, 1H) 10.49 (bs, 2H); MS (ESI) m/z=180 (M+H)$^+$.

Example 95H 1-((S)-2-tert-Butoxycarbonylamino-4-methyl-pentanoyl)-(2,5-cis)-4,4-difluoro-5-methyl-pyrrolidine-2-carboxylic acid methyl ester To 58 mg (0.23 mmol) of N-(tert-butoxycarbonyl)-S-leucine and 100 mg of (dimethylamino-((1,2,3)triazolo(4,5-b)pyridin-3-yloxy)-methylene)-dimethyl-ammonium hexafluorophosphate (HATU) was added 1 mL of N,N-dimethylformamide, then 90 µL (0.52 mmol) of N,N-diisopropylethylamine. The mixture was stirred for 1 min, then added to another flask containing 50 mg (0.23 mmol) of (2,5-cis) 4,4-difluoro-5-methyl-pyrrolidine-2-carboxylic acid methyl ester hydrochloride. After 2 h, the reaction was diluted with 5 mL of H$_2$O and extracted with diethyl ether (3×5 mL). The combined ether layers were back extracted with 1M HCl$_{(aq.)}$, saturated NaHCO$_{3(aq)}$, and brine (1×5 mL), dried over MgSO$_4$, filtered, and concentrated to an oil. The product was purified via silica gel chromatography, eluting with 30% ethyl acetate/hexanes to give the titled compound as a colorless foam. $^1$H NMR (300 MHz, DMSO-d$_6$) δ ppm 0.88 (m, 6H) 1.31 (m, 3H) 1.36 (s, 9H) 1.55 (m, 3H) 2.50 (m, 1H) 2.82 (m, 1H) 3.64 (m, 3H) 4.18 (m, 1H) 4.44 (t, J=9.0 Hz, 1H) 4.71 (m, 1H) 7.32 (d, J=8.1 Hz, 1H); MS (ESI) m/z=393 (M+H)$^+$, 410 (M+NH$_4$)$^+$, 415 (M+Na)$^+$.

Example 95I 1-((S)-2-tert-Butoxycarbonylamino-4-methyl-pentanoyl)-(2,5-cis)-4,4-difluoro-5-methyl-pyrrolidine-2-carboxylic acid To a solution of 69 mg (0.18 mmol) of 1-((S)-2-tert-butoxycarbonylamino-4-methyl-pentanoyl)-(2,5-cis)-4,4-difluoro-5-methyl-pyrrolidine-2-carboxylic acid methyl ester in 2 mL of ethanol was added 0.4 mL (0.8 mmol) of 2M KOH$_{(aq)}$. The reaction was stirred at ambient temperature for 1.5 h, then concentrated in vacuo. The residue was taken up in 5 mL of H$_2$O, and acidified with 2 mL of 1M HCl$_{(aq.)}$, then the suspension was extracted with diethyl ether (3×5 mL). The combined ether layers were back extracted with brine (1×5 mL), dried over MgSO$_4$, filtered, and concentrated to provide the titled compound as a colorless foam. $^1$H NMR (300 MHz, DMSO-d$_6$) δ ppm 0.88 (m, 6H) 1.31 (m, 3H) 1.37 (m, 9H) 1.57 (m, 3H) 2.48 (m, 1H) 2.81 (m, 1H) 4.18 (m, 1H) 4.33 (t, J=9.2 Hz, 1H) 4.72 (m, 1H) 7.30 (d, J=7.8 Hz, 1H), 12.80 (bs, 1H); MS (ESI) m/z=377 (M–H)$^+$.

Example 95J (1-(S)((2,5-cis)-5-Carbamoyl-3,3-difluoro-2-methyl-pyrrolidine-1-carbonyl)-3-methyl-butyl)-carbamic acid tert-butyl ester To a solution of 60 mg (0.159 mmol) of 1-((S)-2-tert-butoxycarbonylamino-4-methyl-pentanoyl)-(2,5-cis)-4,4-difluoro-5-methyl-pyrrolidine-2-carboxylic acid in 1 mL of tetrahydrofuran was added 24 µL (0.22 mmol) of N-methylmorpholine, then 24 µL (0.19 mmol) of isobutyl chloroformate. The mixture was stirred at ambient temperature for 1.5 h, then 0.3 mL of 15M NH$_4$OH was added. After 3.5 h, the reaction was concentrated in vacuo. The residue was taken up in 10 mL of ethyl acetate and extracted with H$_2$O (1×3 mL), 1M HCl (1×3 mL), saturated NaHCO$_3$(aq.) (1×3 mL), and brine (1×3 mL), dried over MgSO$_4$, filtered, and concentrated in vacuo to furnish the titled compound as a colorless foam. TLC 75% ethyl acetate/hexanes, stains with ninhydrin. $^1$H NMR (300 MHz, DMSO-d$_6$) δ ppm 0.88 (m, 6H) 1.30 (m, 3H) 1.36 (s, 9H) 1.55 (m, 3H) 2.31 (m, 1H) 2.64 (m, 1H) 4.13 (m, 1H) 4.37 (t, J=9.0 Hz, 1H) 4.64 (m, 1H) 7.08 (s, 1H) 7.27 (d, J=8.1 Hz, 1H) 7.38 (s, 1H); MS (ESI) m/z=378 (M+H)$^+$, 395 (M+NH$_4$) 400 (M+Na)$^+$.

Example 95K (1-(S)-((2,5-cis)-5-Cyano-3,3-difluoro-2-methyl-pyrrolidine-1-carbonyl)-3-methyl-butyl)-carbamic acid tert-butyl ester To 58 mg (0.15 mmol) of (1-(S)((2,5-cis)-5-carbamoyl-3,3-difluoro-2-methyl-pyrrolidine-1-carbonyl)-3-methyl-butyl)-carbamic acid tert-butyl ester was added 1 mL of pyridine, then 11 mg (0.16 mmol) of imidazole. After the imidazole had dissolved, the reaction was cooled with an ice bath, and 30 mL (0.32 mmol) of phosphorous oxychloride was added. The reaction was stirred for 2 h, then concentrated in vacuo. The residue was taken up in 10 mL of ethyl acetate and extracted with 1M HCl$_{(aq.)}$(2×5 mL), saturated NaHCO$_3$ (1×5 mL), and brine (1×5 mL), dried over MgSO$_4$, filtered, and concentrated to a foam. The product was purified via silica gel chromatography, eluting with 20% ethyl acetate/hexanes to give the titled compound as a colorless foam. $^1$H NMR (300 MHz, DMSO-d$_6$) (mixture of rotamers, major rotamer only) δ ppm 0.90 (m, 6H) 1.28 (m 1H) 1.40 (m, 12H) 1.61 (m, 2H) 2.99 (m, 2H) 4.16 (m, 1H) 4.77 (m, 1H) 4.92 (m, 1H) 7.43 (d, J=7.8 Hz, 1H); MS (ESI) m/z=360 (M+H)$^+$, 377 (M+NH$_4$)$^+$, 382 (M+Na)$^+$.

Example 95

(2S,5S)-4,4-difluoro-1-L-leucyl-5-methylpyrrolidine-2-carbonitrile

To 34 mg (0.095 mmol) of (1-(S)-((2,5-cis)-5-cyano-3,3-difluoro-2-methyl-pyrrolidine-1-carbonyl)-3-methyl-butyl)-carbamic acid tert-butyl ester was added 0.5 mL of trifluoroacetic acid. The solution was allowed to stand at ambient temperature for 10 min, then concentrated in vacuo to give the titled compound as a colorless foam. $^1$H NMR (300 MHz, DMSO-d$_6$) (mixture of rotamers, major rotamer only) δ ppm 0.95 (m, 6H) 1.35 (m, 3H) 1.72 (m, 2H) 3.07 (m, 2H) 4.28 (m, 2H) 4.76 (m, 1H) 5.03 (t, J=8.65 Hz, 1H) 8.31 (s, 3H); MS (ESI) m/z=260 (M+H)+.

Example 96

(2S,5R)-1-((2S)-2-amino-2-cyclohexylethanoyl)-5-vinylpyrrolidine-2-carbonitrile

Example 96A (2S,5R)-1-((2S)-2-tert-Butoxycarbonylamino-2-cyclohexyl-acetyl)-5-trimethylsilanylethynyl-pyrrolidine-2-carboxylic acid methyl ester To a stirred solution of methyl (5R)-5-((trimethylsilyl) ethynyl)-L-prolinate (2 g, 8.87 mmol, Example 1E) in dichloromethane (50 mL) at room temperature under nitrogen was added 4-dimethylaminopyridine (1.08 g, 8.87 mmol), 4-methylmorpholine (1.46 mL, 13.31 mmol), 1-(3-(dimethylamino)propyl)-3-ethyl carbodiimide hydrochloride (2.04 g, 10.65 mmol), and Boc-Gly(cyclohexyl).OH. (2.7 g, 10.65 mmol). The reaction mixture was stirred at room temperature overnight. The reaction mixture was diluted with ethyl acetate and washed with 1M HCl. The aqueous layer was further extracted with ethyl acetate (2×). The combined ethyl acetate layers were dried ($Na_2SO_4$) and evaporated. Purification by flash chromatography 30% EtOAc/hexane gave the desired compound as a white powder. MS (DCI) m/z 465 (M+H)+.

Example 96B (2S,5R)-1-((2S)-2-tert-Butoxycarbonylamino-2-cyclohexyl-acetyl)-5-ethynyl-pyrrolidine-2-carboxylic acid To a stirred solution of 96A (4.3 g, 9.25 mmol), in MeOH (30 mL) and $H_2O$ (30 mL) at room temperature was added LiOH—$H_2O$ (0.58 g, 13.88 mmol). The reaction mixture was stirred at ambient temperature overnight and then evaporated. Water was added to the residue, and the mixture was extracted with $Et_2O$ (2×). The aqueous layer was acidified to pH ~4 by adding 4% $KHSO_4$ dropwise. The clear solution was extracted with EtOAc (3×). Combined EtOAc layers were washed with brine, dried over ($Na_2SO_4$) and evaporated to give the desired compound as a white solid. MS (DCI) m/z 379 (M+H)+.

Example 96C ((2S)-2-((2S,5R)-2-Carbamoyl-5-ethynyl-pyrrolidin-1-yl)-1-cyclohexyl-2-oxo-ethyl)-carbamic acid tert-butyl ester To a stirred solution of the compound from Example 96B (3.07 g, 8.11 mmol) in THF (60 mL) at −15° C. under nitrogen was added 4-methylmorpholine (1.07 mL, 9.73 mmol) and then isobutylchloroformate (1.2 mL, 8.92 mmol) over 2 minutes. A white precipitate was formed. The reaction mixture was stirred at −15° C. under nitrogen for 30 minutes, and a solution of $NH_3$ in dioxane (81.10 mL, 40.55 mmol) was added. The reaction mixture was quenched with 4% $KHSO_4$ to ~pH 4 and extracted with EtOAc (3×). The organic extracts were combined, washed with brine, dried ($Na_2SO_4$) and evaporated. Purification by flash column chromatography (5% MeOH/$CH_2Cl_2$) gave the desired compound. MS (DCI) m/z 378 (M+H)+.

Example 96D ((2S)-2-((2S,5R)-2-Cyano-5-ethynyl-pyrrolidin-1-yl)-1-cyclohexyl-2-oxo-ethyl)-carbamic acid tert-butyl ester To a stirred solution of Example 96E (1 g, 2.46 mmol) and imidazole (0.18 g, 2.64 mmol) in dry pyridine at −35° C. under $N_2$ was added $POCl_3$ dropwise. The reaction mixture was stirred between −35 and −20° C. for 2 hours and then permitted to warm to room temperature. The reaction mixture was concentrated, $CH_2Cl_2$ was added, the white solids were removed by filtration, and the filterate was concentrated. The white solid was purified (30% EtOAc/hexane) to give the desired compound as a foam. MS (DCI) m/z 360 (M+H)+.

Example 96E ((2S)-2-((2S,5R)-2-Cyano-5-vinyl-pyrrolidin-1-yl)-1-cyclohexyl-2-oxo-ethyl)-carbamic acid tert-butyl ester To a solution of ((2S)-2-((2S,5R)-2-cyano-5-ethynyl-pyrrolidin-1-yl)-1-cyclohexyl-2-oxo-ethyl)-carbamic acid tert-butyl ester (0.2 g, 0.53 mmol) and quinoline (0.22 ml) in EtOAc (20 ml) was stirred under hydrogen (20 psi) over 5% Pd/$BaSO_4$ (80 mg). The mixture was stirred at room temperature for 7 minutes. The mixture was diluted with EtOAc and washed with 1.0M HCl. The organic layer was dried over $Na_2SO_4$ and concentrated. Purification by flash chromatography (3% MeOH—$CH_2Cl_2$) gave the desired compound as an oil. MS (DCI) m/z 379 (M+H)+.

Example 96

(2S,5R)-1-((2S)-2-amino-2-cyclohexylethanoyl)-5-vinylpyrrolidine-2-carbonitrile

The reaction mixture of ((2S)-2-((2S,5R)-2-cyano-5-vinyl-pyrrolidin-1-yl)-1-cyclohexyl-2-oxo-ethyl)-carbamic acid tert-butyl ester (0.03 mg, 0.087 mmol) and 4 M HCl in dioxane (0.15 mL, 0.6 mmol) was stirred at room temperature for 2 h and evaporated under reduced pressure. The residue was triturated with ether to provide the titled compound as a white powder. MS (DCI) m/z 362 (M+H)+; $^1$H NMR (300 MHz, MeOH) δ 1.4-1.9 (10H, m), 2.2-2.28 (2H, m), 2.4-2.68 (3H, m), 3.19 (1H, d), 4.3 (1H, d), 4.8 (1H, t), 5.05 (1H, m), 5.9-6.04 (2H, m).

Example 98

(2S,5S)-1-{N-((2R,5S)-hexahydro-2,5-methanopentalen-3a(1H)-yl)glycyl}-5-methylpyrrolidine-2-carbonitrile The title compound was prepared using the conditions described in Example 91 substituting 1-adamantaneamine for cyclopentylamine. 1H NMR (300 MHz, Methanol-d4) δ ppm 1.36 (d, J=6.44 Hz, 3H) 1.67 (m, 4H) 1.98 (m, 8H) 2.43 (m, 5H) 3.88 (m, 1H) 4.21 (m, 2H) 4.78 (t, J=7.80 Hz, 1H). MS (ESI) m/z 288 (M+H)+.

Example 99

(2S,5R)-5-ethynyl-1-(N-(1-tert-butoxy carbonyl-piperidin-4-yl)glycyl)pyrrolidine-2-carbonitrile Example 99 was prepared in the same way as Example 42 by substituting 4-amino-piperidine-1-carboxylic acid tert-butyl ester for trans-4-aminocyclohexanol. MS (ESI) m/z 361 (M+H)$^+$.

Example 100

(2S,5R)-5-ethynyl-1-(N-(1-(5-cyano-pyridin-2-yl)\piperidin-4-yl)glycyl)pyrrolidine-2-carbonitrile Example 100 was prepared in the same manner as Example 31 by substituting 2-chloro-5-cyanopyridine for 5-bromonicotinitrile. MS (CI) m/z 363 (M+1)$^+$.

Example 101

(2S,5R)-1-{N-(1-(4-chlorobenzoyl)-4-methylpiperidin-4-yl)glycyl}-5-ethynylpyrrolidine-2-carbonitrile The titled compound was prepared in the same manner as Example 32 by substituting 4-chlorobenzoyl chloride for 4-chlorocarbonyl-benzoic acid methyl ester. MS (CI) m/z 413 (M+1)$^+$.

Example 102

(2S,5R)-1-{N-(1-(3-cyanophenyl)-4-methylpiperidin-4-yl)glycyl}-5-ethynylpyrrolidine-2-carbonitrile The titled compound was prepared in the same manner as described in Examples 30 and 31 by substituting 3-bromobenzonitrile for 5-bromonicotinonitrile and (4-methyl-piperidin-4-yl)carbamic acid benzyl ester for piperidin-4-ylcarbamic acid tert-butyl ester. MS (CI) m/z 376 (M+1)$^+$.

Example 103

(2S,5R)-1-{N-(1-(4-cyanobenzoyl)-4-methylpiperidin-4-yl)glycyl}-5-ethynylpyrrolidine-2-carbonitrile The titled compound was prepared in the same manner as example 39 by substituting isonicotinyl chloride with 4-cyanobenzoyl chloride. MS (CI) m/z 404 (M+1)$^+$.

Example 105

(2S,5R)-1-{N-(1-(4-bromobenzoyl)-4-methylpiperidin-4-yl)glycyl}-5-ethynylpyrrolidine-2-carbonitrile The titled compound was prepared in the same manner as example 39 by substituting isonicotinyl chloride with 4-bromobenzoyl chloride. MS (CI) m/z 458 (M+1)$^+$.

Example 106

(2S,5R)-5-ethynyl-1-(N-{4-methyl-1-(4-(trifluoromethyl)pyridin-2-yl)piperidin-4-yl}glycyl)pyrrolidine-2-carbonitrile The titled compound was prepared in the same manner as example 29 by substituting 2-fluoropyridine with 2-chloro-4-(trifluoromethyl)pyridine. MS (CI) m/z 420 (M+1)$^+$.

Example 107

(2S,5R)-1-{N-(4-trans(4-cyano-2-fluorophenoxy)cyclohexyl)glycyl}-5-ethynylpyrrolidine-2-carbonitrile The titled compound was prepared in the same way as example 48 by substituting 3,4-difluorobenzonitrile for 4-fluorobenzonitrile. MS (ESI) m/z 395 (M+H)$^+$.

Example 108

(2S,5R)-5-ethynyl-1-{N-(4-trans(3-fluorophenoxy)-1-methylcyclohexyl)glycyl}pyrrolidine-2-carbonitrile The titled compound was prepared in the same way as example 46 by substituting 1,3-difluorobenzene for 3-fluoropyridine. MS (ESI) m/z 384 (M+H)$^+$.

Example 109

(2S,5R)-1-{N-(4-trans(3-cyanophenoxy)cyclohexyl)glycyl}-5-ethynylpyrrolidine-2-carbonitrile The titled compound was prepared in the same way as example 48 by substituting 3-fluorobenzonitrile for 4-fluorobenzonitrile. MS (ESI) m/z 377 (M+H)$^+$.

Example 111

(2S,5R)-1-(N-{4-trans ((5-chloropyridin-2-yl)oxy)cyclohexyl}glycyl)-5-ethynylpyrrolidine-2-carbonitrile The titled compound was prepared in the same way as example 48 by substituting 2,5-dichloropyridine for 4-fluorobenzonitrile. MS (ESI) m/z 387 (M+H)$^+$.

Example 112

(2S,5R)-5-ethynyl-1-(N-(4-trans{(4'-fluoro-2-(trifluoromethyl)-1,1'-biphenyl-4-yl)oxy}cyclohexyl)glycyl)pyrrolidine-2-carbonitrile The titled compound was prepared in the same way as example 43 by substituting 1-bromo-4-fluoro-2-trifluoromethyl benzene for 3-bromo-4-fluoro-1-trifluoromethyl benzene. MS (ESI) m/z 514 (M+H)$^+$.

Example 113

(2S,5R)-5-ethynyl-1-(N-(4-trans{(4'-fluoro-6-(trifluoromethyl)-1,1'-biphenyl-3-yl)oxy}cyclohexyl)glycyl)pyrrolidine-2-carbonitrile The titled compound was prepared in the same way as example 43 by substituting 2-bromo-4-fluoro-1-trifluoromethyl benzene for 3-bromo-4-fluoro-1-trifluoromethyl benzene. MS (ESI) m/z 514 (M+H)$^+$.

Example 114

(2S,5R)-1-(N-{4-(3-cyano-4-trans (trifluoromethyl)phenoxy)cyclohexyl}glycyl)-5-ethynylpyrrolidine-2-carbonitrile The titled compound was prepared in the same way as example 48 by substituting 5-fluoro-2-trifluoromethyl-benzonitrile for 4-fluorobenzonitrile. MS (ESI) m/z 445 (M+H)$^+$.

Example 115

(2S,5R)-1-{N-(4-trans(3-bromophenoxy)cyclohexyl)glycyl}-5-ethynylpyrrolidine-2-carbonitrile The titled compound was prepared in the same way as example 48 by substituting 1-bromo-3-fluoro-benzene for 4-fluorobenzonitrile. MS (ESI) m/z 431 (M+H)$^+$.

Example 116

(2S,5R)-1-{N-(4-trans(4-cyano-3-fluorophenoxy)cyclohexyl)glycyl}-5-ethynylpyrrolidine-2-carbonitrile The titled compound was prepared in the same way as example 48 by substituting 2,4-difluorobenzonitrile for 4-fluorobenzonitrile. MS (ESI) m/z 395 (M+H)$^+$.

Example 117

(2S,5R)-1-(N-{4-(2-cyano-4-trans(trifluoromethyl)phenoxy)cyclohexyl}glycyl)-5-ethynylpyrrolidine-2-carbonitrile The titled compound was prepared in the same way as example 48 by substituting 2-fluoro-5-trifluoromethyl-benzonitrile for 4-fluorobenzonitrile. MS (ESI) m/z 445 (M+H)$^+$.

Example 118

(2S,5R)-1-{N-(4-trans(3-cyanophenoxy)-1-methylcyclohexyl)glycyl}-5-ethynylpyrrolidine-2-carbonitrile The titled compound was prepared in the same way as example 46 by substituting 3-fluorobenzonitrile for 3-fluoropyridine. MS (ESI) m/z 391 (M+H)$^+$.

Example 119

(2S,5R)-1-{N-(4-trans(4-chlorophenoxy)cyclohexyl)glycyl}-5-ethynylpyrrolidine-2-carbonitrile The titled compound was prepared in the same way as example 48 by substituting 1-chloro-4-fluoro-benzene for 4-fluorobenzonitrile. MS (ESI) m/z 386 (M+H)$^+$.

Example 120

(2S,5R)-5-ethynyl-1-(N-(4-trans{(6-methyl-4-(trifluoromethyl)pyridin-2-yl)oxy}cyclohexyl)glycyl)pyrrolidine-2-carbonitrile The titled compound was prepared in the same way as example 48 by substituting 2-chloro-6-methyl-4-trifluoromethyl-pyridine for 4-fluorobenzonitrile. MS (ESI) m/z 435 (M+H)$^+$.

Example 121

(2S,5R)-1-(N-{4-trans(2-cyano-3-(trifluoromethyl)phenoxy)cyclohexyl}glycyl)-5-ethynylpyrrolidine-2-carbonitrile The titled compound was prepared in the same way as example 48 by substituting 2-fluoro-6-trifluoromethyl-benzonitrile for 4-fluorobenzonitrile. MS (ESI) m/z 445 (M+H)$^+$.

Example 122

(2S,5R)-5-ethynyl-1-(N-{4-trans(4-pyridin-4-yl-3-(trifluoromethyl)phenoxy)cyclohexyl}glycyl)pyrrolidine-2-carbonitrile The titled compound was prepared in the same way as example 43 by substituting 4-pyridyl boronic acid for 4-fluorophenyl boronic acid and 2-bromo-5-fluorobenzotrifluoride for 3-bromo-4-fluoro-1-trifluoromethylbenzene. MS (ESI) m/z 497 (M+H)$^+$.

Example 123

(2S,5R)-1-(N-{4-trans(3-cyano-5-(trifluoromethyl)phenoxy)cyclohexyl}glycyl)-5-ethynylpyrrolidine-2-carbonitrile The titled compound was prepared in the same way as example 48 by substituting 3-fluoro-5-trifluoromethyl-benzonitrile for 4-fluorobenzonitrile. MS (ESI) m/z 445 (M+H)$^+$.

Example 124

(2S,5R)-5-ethynyl-1-{N-(4-(4-fluorophenoxy)-1-methylcyclohexyl)glycyl}pyrrolidine-2-carbonitrile The titled compound was prepared in the same way as example 46 by substituting 1,4-difluorobenzene for 3-fluoropyridine. MS (ESI) m/z 384 (M+H)$^+$.

Example 125

(2S,5R)-5-ethynyl-1-{N-(4-(3-fluorophenoxy)-1-methylcyclohexyl)glycyl}pyrrolidine-2-carbonitrile The titled compound was prepared in the same way as example 46 by substituting 1,3-difluorobenzene for 3-fluoropyridine. MS (ESI) m/z 384 (M+H)$^+$.

Example 127

(2S,5R)-5-ethynyl-1-(N-{4-trans(3-(trifluoromethyl)phenoxy)cyclohexyl}glycyl)pyrrolidine-2-carbonitrile The titled compound was prepared in the same way as example 48 by substituting 1-fluoro-3-trifluoromethyl-benzene for 4-fluorobenzonitrile. MS (ESI) m/z 420 (M+H)$^+$.

Example 128

(2S,5R)-1-(N-{4-trans ((3-bromopyridin-2-yl)oxy)cyclohexyl}glycyl)-5-ethynylpyrrolidine-2-carbonitrile The titled compound was prepared in the same way as example 48 by substituting 3-bromo-2-chloro-pyridine for 4-fluorobenzonitrile. MS (ESI) m/z 432 (M+H)$^+$.

Example 129

(2S,5R)-5-ethynyl-1-(N-(4-trans{(4-(trifluoromethyl)pyridin-2-yl)oxy}cyclohexyl)glycyl)pyrrolidine-2-carbonitrile The titled compound was prepared in the same way as example 48 by substituting 2-chloro-4-trifluoromethyl-pyridine for 4-fluorobenzonitrile. MS (ESI) m/z 421 (M+H)+.

Example 130

(2S,5R)-1-(N-{4-trans ((5-chloropyridin-2-yl)oxy)-1-methylcyclohexyl}glycyl)-5-ethynylpyrrolidine-2-carbonitrile The titled compound was prepared in the same way as example 46 by substituting 2,5-dichloropyridine for 3-fluoropyridine. MS (ESI) m/z 401 (M+H)+.

Example 131

(2S,5R)-1-{N-(4-trans(3-cyanophenoxy)-1-methyl-cyclohexyl)glycyl}-5-ethynylpyrrolidine-2-carbonitrile The titled compound was prepared in the same way as example 46 by substituting 3-fluorobenzonitrile for 3-fluoropyridine. MS (ESI) m/z 391 (M+H)+.

Example 132

(2S,5R)-5-ethynyl-1-(N-{4-trans(4-(trifluoromethyl)-5-(carboxy)phenoxy)cyclohexyl}glycyl)pyrrolidine-2-carbonitrile The titled compound was prepared in the same way as example 48 by substituting 2-fluoro-5-trifluoromethyl-benzoic acid for 4-fluorobenzonitrile. MS (ESI) m/z 464 (M+H)+.

Example 133

(2S,5R)-1-{N-(4-trans(3-chlorophenoxy)cyclohexyl)glycyl}-5-ethynylpyrrolidine-2-carbonitrile The titled compound was prepared in the same way as example 48 by substituting 1-chloro-3-fluoro-benzene for 4-fluorobenzonitrile. MS (ESI) m/z 386 (M+H)+.

Example 134

(2S,5R)-5-ethynyl-1-(N-(1-methyl-4-trans{(5-(trifluoromethyl)pyridin-2-yl)oxy}cyclohexyl)glycyl)pyrrolidine-2-carbonitrile The titled compound was prepared in the same manner as example 46 by substituting 2-chloro-5-trifluoromethylpyridine for 3-fluoropyridine. The titled compound is a mixture of diastereomers at the ether bearing carbon. MS (CI) m/z 435 (M+1)+.

Example 135

(2S,5R)-1-{N-(4-trans(4-bromophenoxy)cyclohexyl)glycyl}-5-ethynylpyrrolidine-2-carbonitrile The titled compound was prepared in the same way as example 48 by substituting 1-bromo-4-fluorobenzene for 4-fluorobenzonitrile. MS (ESI) m/z 431 (M+H)+.

Example 136

(2S,5R)-1-(N-{1,1-dimethyl-2-((3-cyano-6-methylpyridin-2-yl)amino)ethyl}glycyl)-5-ethynylpyrrolidine-2-carbonitrile The titled compound was prepared using the same procedure as described for Example 155 by substituting 6-chloronicotinonitrile with 2-chloro-3-cyano-6-methylpyridine. MS (DCI/NH3) m/z 365 (M+H)+.

Example 137

(2S,5R)-1-(N-(1,1-dimethyl-2-{(5-(trifluoromethyl)pyridin-2-yl)oxy}ethyl)glycyl)-5-ethynylpyrrolidine-2-carbonitrile The titled compound was prepared using the same procedure as described for Example 66 substituting 2-chloro-5-(trifluoromethyl)pyridine for 6-chloronicotinonitrile. MS (DCI/NH3) m/z 394 (M+H)+.

Example 138

(2S,5R)-1-(N-{1,1-dimethyl-2-((3-cyano-6-methylpyridin-2-yl)oxy)ethyl}glycyl)-5-ethynylpyrrolidine-2-carbonitrile The titled compound was prepared using the same procedure as described for Example 66 substituting 2-chloro-3-cyano-6-methylpyridine for 6-chloronicotinonitrile. MS (DCI/NH3) m/z 366 (M+H)+.

Example 139

(2S,5R)-5-ethynyl-1-(N-(tetrahydrofuran-2-ylmethyl)glycyl)pyrrolidine-2-carbonitrile The titled compound was prepared in the same way as example 42 by substituting C-(tetrahydro-furan-2-yl)-methylamine for trans-4-aminocyclohexanol. MS (ESI) m/z 262 (M+H)+.

Example 140

(2S,5R)-5-ethynyl-1-(N-(pyridin-2-ylmethyl)glycyl)pyrrolidine-2-carbonitrile

The titled compound was prepared in the same manner as example 42 by substituting C-pyridin-2-yl-methylamine for trans-4-aminocyclohexanol. MS (CI) m/z 435 (M+1)+.

Example 141

(2S,5R)-5-ethynyl-1-(N-(2-pyridin-4-ylethyl)glycyl) pyrrolidine-2-carbonitrile

The titled compound was prepared in the same manner as example 42 by substituting 2-pyridin-4-yl-ethylamine for trans-4-aminocyclohexanol. MS (CI) m/z 283 (M+1)$^+$.

Example 142

(2S,5R)-5-ethynyl-1-{N#1-tert-butoxycarbonylpiperidin-4-yl)methyl)glycyl}pyrrolidine-2-carbonitrile The titled compound was prepared in the same way as example 42 by substituting 4-aminomethyl-piperidine-1-carboxylic acid tert-butyl ester for trans-4-aminocyclohexanol. MS (ESI) m/z 375 (M+H)$^+$.

Example 143

(2S,5R)-5-ethynyl-1-{N-(3-(methylamino)propyl) glycyl}pyrrolidine-2-carbonitrile The titled compound was prepared by treating Example 151 with 4 M HCl in dioxane. MS (ESI) m/z 249 (M+H)$^+$.

Example 144

(2S,5R)-5-ethynyl-1-(N-(4-tert-butyloxycarbonylbutyl)glycyl)pyrrolidine-2-carbonitrile The titled compound was prepared in the same way as example 42 by substituting 4-amino-butyric-acid tert-butyl ester for trans-4-aminocyclohexanol. MS (ESI) m/z 320 (M+H)$^+$.

Example 145

(2S,5R)-5-ethynyl-1-(N-(3-hydroxy-2,2-dimethyl-propyl)glycyl)pyrrolidine-2-carbonitrile The titled compound was prepared as described in Example 160 substituting neopentanolamine for cyclopropylamine. MS (DCI/NH$_3$), m/z=264 (M+H)$^+$.

Example 146

2-{[2-({2-[(2S,5R)-2-cyano-5-ethynylpyrrolidin-1-yl]-2-oxoethyl}amino)-2-methylpropyl] amino}isonicotinonitrile The titled compound was prepared using the same procedure as described for Example 155 by substituting 6-chloronicotinonitrile with 2-chloro-4-cyanopyridine. MS (DCI/NH$_3$) m/z 351 (M+H)$^+$.

Example 147

(2S,5R)-1-(N-(1,1-dimethyl-2-{(4-(trifluoromethyl) pyrimidin-2-yl)amino}ethyl)glycyl)-5-ethynylpyrrolidine-2-carbonitrile The titled compound was prepared using the same procedure as described for Example 155 by substituting 6-chloronicotinonitrile with 2-chloro-4-(trifluoromethyl)pyrimidine. MS (DCI/NH$_3$) m/z 395 (M+H)$^+$.

Example 148 methyl 6-{[2-({2-[(2S,5R)-2-cyano-5-ethynylpyrrolidin-1-yl]-2-oxoethyl}amino)-2-methylpropyl] amino}nicotinate The titled compound was prepared using the same procedure as described for Example 155 substituting 6-chloronicotinonitrile with methyl 6-chloronicotinate. MS (DCI/NH$_3$) m/z 424 (M+H)$^+$.

Example 149

(2S,5R)-1-{N-(2-(2-cyano-5-fluorophenoxy)-1,1-dimethylethyl)glycyl}-5-ethynylpyrrolidine-2-carbonitrile The titled compound was prepared using the same procedure as described for Example 66 by substituting 2,4-difluorobenzonitrile for 6-chloronicotinonitrile. MS (DCI/NH3) m/z 369 (M+H)$^+$.

Example 150

(2S,5R)-5-ethynyl-1-(N-(4-iodobenzyl)glycyl)pyrrolidine-2-carbonitrile

The titled compound was prepared in the same way as example 42 by substituting 4-iodo-benzylamine for trans-4-aminocyclohexanol. MS (ESI) m/z 394 (M+H)$^+$.

Example 151

(2S,5R)-5-ethynyl-1-{N-(3-(methylamino)-3-tert butyloxy carbonylpropyl)glycyl}pyrrolidine-2-carbonitrile The titled compound was prepared in the same way as example 42 by substituting (3-amino-propyl)methyl carbamic acid tert-butyl ester for trans-4-aminocyclohexanol. MS (ESI) m/z 349 (M+H)$^+$.

Example 152

(2S,5R)-5-ethynyl-1-(N-(4-carboxybutyl)glycyl) pyrrolidine-2-carbonitrile

The titled compound was prepared by treating Example 144 with 4 M HCl in dioxane. MS (ESI) m/z 263 (M+H)$^+$.

Example 153

(2S,5R)-1-(N-(2-{(3-chloro-5-(trifluoromethyl)pyridin-2-yl)amino}ethyl)glycyl)-5-ethynylpyrrolidine-2-carbonitrile Example 153 was prepared in the same way as example 42 by substituting N1-(3-chloro-5-trifluoromethyl-pyridin-2-yl)-ethane-1,2-diamine for trans-4-aminocyclohexanol. MS (ESI) m/z 400 (M+H)$^+$.

Example 154

(2S,5R)-5-ethynyl-1-(N-(3-isopropoxypropyl)glycyl)pyrrolidine-2-carbonitrile

The titled compound was prepared in the same way as example 42 by substituting 3-isopropoxy propylamine for trans-4-aminocyclohexanol. MS (ESI) m/z 278 (M+H)$^+$.

Example 155

(2S,5R)-1-{N-(1,1-dimethyl-2-(5-cyanopyridin-2-ylamino)ethyl)glycyl}-5-ethynylpyrrolidine-2-carbonitrile

Example 155A 6-(2-Amino-2-methyl-propylamino)-nicotinonitrile

A mixture of 1,2-diamino-2-methylpropane (3.14 ml, 30 mmol), and 6-chloronicotinonitrile (2.77 g, 20 mmol) were heated to 120° C. for 2 days. The reaction mixture was filtered, and the inorganic salt was rinsed with EtOAc. The filterate was concentrated under reduced pressure to provide the titled compound as a pale yellow solid. MS (DCI) m/z 191 (M+H)$^+$.

Example 155

(2S,5R)-1-{N-(1,1-dimethyl-2-(5-cyanopyridin-2-ylamino)ethyl)glycyl}-5-ethynylpyrrolidine-2-carbonitrile To a stirred solution of (2S,5R)-1-(chloroacetyl)-5-ethynylpyrrolidine-2-carbonitrile (0.05 g, 0.255 mmol, Example 8D) in acetonitrile (3 mL) at room temperature under nitrogen was added 6-(2-amino-2-methyl-propylamino)-nicotinonitrile (0.1 g, 0.51 mmol). The reaction mixture was stirred overnight and then concentrated under reduced pressure. The residue was flash chromatographed with 2% MeOH/CH$_2$Cl$_2$ to provide the desired compound as a white solid. MS (DCI) m/z 351 (M+H)$^+$; $^1$H NMR (300 MHz, DMSO-d$_6$) δ 2.03-2.5 (2H, m), 2.55 (2H, s), 2.1 (2H, s), 3.5 (1H, m), 3.82 (6H, s), 3.9-4.6 (2H, m), 4.7-4.82 (1H, m), 4.88-5.5 (1H, m), 7.3-7.5 (3H, m).

Example 156

(2S,5R)-1-(N-(2-(4-carboxyanilino)-1,1-dimethylethyl)glycyl)-5-ethynylpyrrolidine-2-carbonitrile

Example 156A (2S,5R)-1-(N-(2-(4-tert-butoxycarbonyl)-anilino-1,1-dimethylethyl)glycyl)-5-ethynylpyrrolidine-2-carbonitrile The titled compound was prepared using the same procedure as described for Example 155 substituting tert-butyl 4-fluorobenzoate for 6-chloronicotinonitrile. MS (DCI/NH$_3$) m/z 424 (M+H)$^+$.

Example 156

(2S,5R)-1-(N-(2-(4-carboxyanilino)-1,1-dimethylethyl)glycyl)-5-ethynylpyrrolidine-2-carbonitrile A mixture of the tert-butylbenzoate described above in 4 M HCl in dioxane was stirred at 23° C. for 2 hours. The dioxane was removed in vacuo, and the crude solid was triturated several times with diethyl ether. The resulting white solid was dried in vacuum oven overnight to afford the HCl salt of the titled compound. MS (DCI/NH$_3$) m/e 368 (M+H)$^+$.

Example 157

(2S,5R)-5-ethynyl-1-{N-(1-(1-hydroxy-1-methylethyl)cyclopentyl)glycyl}pyrrolidine-2-carbonitrile The titled compound was prepared in the same way as example 42 by substituting 2-(1-amino-cyclopentyl)-propan-2-ol for trans-4-aminocyclohexanol. MS (ESI) m/z 304 (M+H)$^+$.

Example 158

(2S,5R)-5-ethynyl-1-{N-((2R,5S)-hexahydro-2,5-methanopentalen-3a(1H)-yl)glycyl}pyrrolidine-2-carbonitrile The titled compound was prepared in the same way as example 42 by substituting 3-noradamantanamine for trans-4-aminocyclohexanol. MS (ESI) m/z 334 (M+H)$^+$.

Example 159

(2S,5R)-1-(N-cyclopentylglycyl-(N-methyl1-aminocyclopentanecarboxy)-5-ethynylpyrrolidine-2-carbonitrile The titled compound was prepared in the same way as example 42 by substituting 1-amino-cyclopentane carboxylic acid methyl ester for trans-4-aminocyclohexanol. MS (ESI) m/z 304 (M+H)$^+$.

Example 160

(2S,5R)-1-(N-cyclopropylglycyl)-5-ethynylpyrrolidine-2-carbonitrile

To a stirred solution of Example 8D (0.045 g, 0.228 mmol) in acetonitrile (2 mL) at room temperature under nitrogen was added cyclopropylamine (0.032 ml, 0.457 mmol). The reaction mixture was stirred overnight and then concentrated under reduced pressure. The residue was flash chromatographed with 3% MeOH/CH$_2$Cl$_2$ to provide the desired compound as a pale yellow oil. MS m/z 218 (M+H)$^+$; $^1$H NMR (300 MHz, DMSO-d$_6$) δ 1.5-2 (4H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m).

Example 161

(2S,5R)-5-ethynyl-1-(N-piperidin-4-ylglycyl)pyrrolidine-2-carbonitrile

The titled compound was prepared by treating Example 99 with 4 M HCl in dioxane. MS (ESI) m/z 261 (M+H)$^+$.

Example 162

(2S,5R)-5-ethynyl-1-{N-((5R,7S)-3-hydroxy-1-adamantyl)glycyl}pyrrolidine-2-carbonitrile To a stirred solution of Example 8D (0.06 g, 0.305 mmol) in acetonitrile (3 mL) at room temperature under nitrogen, was added 3-amino-1-adamantanol (0.1 g, 0.61 mmol). The reaction mixture was stirred for two days and then concentrated under reduced pressure. The residue was flash chromatographed with 5-7% MeOH/CH$_2$Cl$_2$ to provide the desired compound as a pale yellow oil. MS (DCI) m/z 328 (M+H)$^+$; $^1$H NMR (300 MHz, DMSO-d$_6$) δ 1.5-2 (14H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m).

Example 163

(2S,5R)-5-ethynyl-1-((3R)—N-tetrahydrofuran-3-ylglycyl)pyrrolidine-2-carbonitrile To a stirred solution of Example 8D (0.03 g, 0.153 mmol) and potassium carbonate (0.2 g, 1.53 mmol) in acetonitrile (2 mL), at room temperature under nitrogen was added R(+)-3-aminotetrahydrofuran toluene-4-sulfonate (0.08 g, 0.32 mmol). The reaction mixture was stirred overnight and then concentrated under reduced pressure. The residue was flash chromatographed with 2% MeOH/CH$_2$Cl$_2$ to provide the desired compound as a pale yellow oil. MS (DCI) m/z 248 (M+H)$^+$; $^1$H NMR (300 MHz, DMSO-d$_6$) δ 1.5-2 (2H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m), 5.43-5.9 (4H, m).

Example 164

(2S,5R)-1-(N-cycloheptylglycyl)-5-ethynylpyrrolidine-2-carbonitrile

The titled compound was prepared as described in Example 160 substituting cyclopropylamine with cycloheptylamine. MS (DCI) m/z 274 (M+H)$^+$; $^1$H NMR (300 MHz, DMSO-d$_6$) δ 1.5-2 (12H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m).

Example 165

(2S,5R)-1-(N-cyclobutylglycyl)-5-ethynylpyrrolidine-2-carbonitrile

The titled compound was prepared as described in Example 160 substituting cyclopropylamine with cyclobutylamine. MS (DCI) m/z 232 (M+H)$^+$; $^1$H NMR (300 MHz, DMSO-d$_6$) δ 1.5-2 (6H, m), 2.11-2.21 (2H, m), 2.45-2.48 (2H, m), 3.78 (1H, d), 3.8-4.5 (2H, m), 4.53-4.55 (1H, t), 5.01 (1H, m), 5.05 (1H, m).

Example 166

(2S,5R)-5-ethynyl-1-(3-methyl-L-valyl)pyrrolidine-2-carbonitrile

The titled compound was prepared according to the procedures for Example 1F-J substituting N-(t-butoxycarbonyl)-L-t-butylglycine for N-(t-butoxycarbonyl)-L-leucine monohydrate in the step described in Example 1F. MS (DCI/NH$_3$) m/z 233 (M+H)$^+$.

Example 167

(2S,5R)-5-ethynyl-1-(3-pyridin-4-yl-L-alanyl)pyrrolidine-2-carbonitrile

The titled compound was prepared in the same manner as example 1 by substituting (2S)-tert-butoxycarbonylamino-3-pyridin-4-yl-propionic acid for N-(tert-butoxycabonyl)-L-leucine monohydrate. MS (CI) m/z 269 (M+1)$^+$.

Example 168

(2S,5R)-1-L-leucyl-5-prop-1-ynylpyrrolidine-2-carbonitrile

The titled compound was prepared in the same way as example 85 by substituting t-Boc-L-Leucine for Boc-cyclopentyl-L-glycine.dicyclohexylamine. MS (ESI) m/z 248 (M+H)$^+$.

Example 169

(2S,5R)-1-(3-methyl-L-valyl)-5-prop-1-ynylpyrrolidine-2-carbonitrile

The titled compound was prepared in the same way as example 85 by substituting Boc-L-tert-leucine for Boc-cyclopentyl-L-glycine.dicyclohexylamine. MS (ESI) m/z 248 (M+H)$^+$.

Example 170

(2S,5R)-1-(N-cyclobutylglycyl)-5-prop-1-ynylpyrrolidine-2-carbonitrile

The titled compound was prepared in the same way as example 88 by substituting cyclobutylamine for cyclopentylamine. MS (ESI) m/z 246 (M+H)$^+$.

Example 171

(2S,5R)-1-(N-(4-trans hydroxycyclohexyl)glycyl)-5-prop-1-ynylpyrrolidine-2-carbonitrile The titled compound was prepared in the same way as example 88 by substituting trans-4-aminocyclohexanol for cyclopentylamine. MS (ESI) m/z 290 (M+H)$^+$.

Example 172

(2S,5R)-1-{N-((2S)-2-hydroxycyclopentyl)glycyl}-5-prop-1-ynylpyrrolidine-2-carbonitrile The titled compound was prepared in the same way as example 88 by substituting 2-amino-cyclopentanol for cyclopentylamine. MS (ESI) m/z 276 (M+H)$^+$.

Example 173

(2S,5S)-5-methyl-1-{N-((1S,2S,3S,5R)-2,6,6-trimethylbicyclo(3.1.1) hept-3-yl)glycyl}pyrrolidine-2-carbonitrile The titled compound was prepared using the methodology described in Example 91 substituting (+)-isopinocampheylamine for cyclopentylamine. MS (DCI) m/z 304 (M+H)$^+$.

Example 174

(2S,5S)-1-{N-((5R,7S)-3-hydroxy-1-adamantyl)glycyl}-5-methylpyrrolidine-2-carbonitrile The titled compound was prepared using the methodology described in Example 91 substituting 3-amino-1-adamantanol for cyclopentylamine. MS (DCI) m/z 318 (M+H)+.

Example 175

(2S,5S)-1-{N-(2-(3,4-dimethoxyphenyl)ethyl)glycyl}-5-methylpyrrolidine-2-carbonitrile The titled compound was prepared using the methodology described in Example 91 substituting homoveratrylamine for cyclopentylamine. MS (DCI) m/z 332 (M+H)+.

Example 176

(2S,5S)-4,4-difluoro-5-methyl-1-((5S)-5-methyl-L-prolyl)pyrrolidine-2-carbonitrile The titled compound was prepared using methodologies described in Examples 6 and 95 substituting (2R,5S)-5-methyl-pyrrolidine-1,2-dicarboxylic acid 1-tert-butyl ester for N-(tert-butoxy carbonyl)-S-leucine. MS (ESI) m/z=258 (M+H)+.

Example 177

(2S,5S)-1-(N-isopropylglycyl)-5-methylpyrrolidine-2-carbonitrile

The titled compound was prepared using the methodology described in Example 91 substituting isopropylamine for cyclopentylamine. MS (DCI) m/z 210 (M+H)+.

Example 178

(2S,5S)-1-L-iso leucyl-5-methylpyrrolidine-2-carbonitrile

The titled compound was prepared using methodology described in Examples 91, 28 and 6 substituting N-(tert-butoxycarbonyl)-L-isoleucine for N-(tert-butoxycarbonyl)-L-leucine hydrate. MS (DCI) m/z 224 (M+H)+.

Example 179

(2S,5S)-5-methyl-1-{N-(2-(5-cyano-pyridin-2-ylamino)ethyl)glycyl}pyrrolidine-2-carbonitrile The titled compound was prepared using methodologies described in Example 91 and in Villhauer, E. B.; Brinkman, J. A.; Naderi, G. B.; Burkey, B. F.; Dunning, B. E.; Prasad, K.; Mangold, B. L.; Russell, M. E.; Hughes, T. E. *J. Med. Chem.* 2003, 46, 2774-2789. MS (DCI) m/z 313 (M+H)+.

Example 180

(2S,5S)-5-methyl-1-((3S)-1,2,3,4-tetrahydroisoquinolin-3-ylcarbonyl)pyrrolidine-2-carbonitrile The title compound was prepared as described in Example 28 substituting Boc-L-Tic-OH for N-(tert-butoxycarbonyl)-L-leucine hydrate. MS (ESI) m/z 270 (M+H)+.

Example 181

(2S,5S)-1-(3-cyclopropyl-L-alanyl)-5-methylpyrrolidine-2-carbonitrile

The title compound was prepared as described in Example 28 substituting beta-cyclopropyl-L-alanine Boc for N-(tert-butoxycarbonyl)-L-leucine hydrate. MS (DCI) m/z 208 (M+H)+.

Example 182

(2S,5S)-5-methyl-1-D-prolylpyrrolidine-2-carbonitrile

The title compound was prepared as described in Example 28 substituting Boc-L-proline for N-(tert-butoxycarbonyl)-L-leucine hydrate. MS (DCI) m/z 322 (M+H)+.

Example 183

(2S,5S)-1-(N-2,3-dihydro-1H-inden-1-ylglycyl)-5-methylpyrrolidine-2-carbonitrile The titled compound was prepared using the methodology described in Example 91 substituting 1-aminoindane for cyclopentylamine. MS (DCI) m/z 284 (M+H)+.

Example 184

(2S,5S)-5-methyl-1-L-valylpyrrolidine-2-carbonitrile

The title compound was prepared as described in Example 28 substituting N-(tert-butoxycarbonyl)-L-valine for N-(tert-butoxycarbonyl)-L-leucine hydrate. MS (DCI) m/z 211 (M+H)+.

Example 185

(2S,5S)-5-methyl-1-(4-methyl-L-leucyl)pyrrolidine-2-carbonitrile

The title compound was prepared as described in Example 28 substituting N-(tert-butoxycarbonyl)-L-t-butyl-alanine for N-(tert-butoxycarbonyl)-L-leucine hydrate. MS (DCI) m/z 238 (M+H)+.

Example 186

(2S,5S)-1-(N-(4-trans hydroxycyclohexyl)glycyl)-5-methylpyrrolidine-2-carbonitrile The titled compound was prepared using the methodology described in Example 91 substituting trans-4-aminocyclohexanol for cyclopentylamine. MS (DCI) m/z 266 (M+H)+.

Example 187

(2S,5S)-1-(N-(tert-butyl)glycyl)-5-methylpyrrolidine-2-carbonitrile

The titled compound was prepared using the methodology described in Example 91 substituting t-butylamine for cyclopentylamine. MS (DCI) m/z 224 (M+H)+.

Example 188

(2S,5S)-5-methyl-1-((5S)-5-methyl-L-prolyl)pyrrolidine-2-carbonitrile

The title compound was prepared using the methodology described in Examples 28, 6, and 176. MS (DCI) m/z 222 (M+H)$^+$.

Example 189

(2S,5S)-1-(3-cyclohexyl-L-alanyl)-5-methylpyrrolidine-2-carbonitrile

The title compound was prepared as described in Example 28 substituting N-(tert-butoxycarbonyl)-L-cyclohexylalanine for N-(tert-butoxycarbonyl)-L-leucine hydrate. MS (DCI) m/z 264 (M+H)$^+$.

Example 190

6-{[4-({2-[(2S,5R)-2-cyano-5-ethynylpyrrolidin-1-yl]-2-oxoethyl}amino)-4-methylcyclohexyl]oxy}-N,N-dimethylnicotinamide

Example 190A 6-(4-amino-4-methyl-cyclohexyloxy)-N,N-dimethylnicotinamide

To a mixture of sodium hydride (240 mg, 6.0 mmol) in dimethylformamide (10 mL) at 0° C. was added Example 45F (258 mg, 2.0 mmol). The resulting mixture was stirred at 0° C. for 30 minutes, then Example 40A (473 mg, 2.4 mmol) was added. It was heated to 60° C. for 2 hours and stirred for 12 hours at room temperature. The reaction mixture was diluted with ethyl acetate and washed with water (3 times) and brine. The organic layer was dried (sodium sulfate), filtered, and concentrated under reduced pressure to provide the titled compound. MS (DCI) m/z 278 (M+H)$^+$.

Example 190

A mixture of Example 190A (194 mg, 0.31 mmol) and Example 8D (30 mg, 0.153 mmol) in acetonitrile (1 mL) were stirred at 23° C. for 48 hours. The reaction mixture was stirred at room temperature for 48 hours, concentrated under reduced pressure and purified by HPLC to provide the titled compound. MS (ESI) m/z 438 (M+H)$^+$; $^1$H NMR (300 MHz, MeOH-d$_4$) δ ppm 8.25 (d, 1H), 7.78 (dd, 1H), 6.86 (d, 1H), 4.95 (m, 1H), 4.86 (m, 1H), 4.20 (AB quartet, 2H), 3.08 (s, 6H), 2.50-2.37 (m, 4H), 2.33 (m, 1H), 2.16-1.98 (m, 4H) 1.93-1.73 (m, 4H), 1.49 (s, 3H).

Example 191

(1S,3R)-3-({2-[(2S,5R)-2-cyano-5-ethynylpyrrolidin-1-yl]-2-oxoethyl}amino)-N-(pyridin-2-ylmethyl)cyclopentanecarboxamide

Example 191A (1S,3R)-3-tert-butoxycarbonylamino-cyclopentanecarboxylic acid

To a cold solution (0° C.) of (1S,3R)-3-amino-cyclopentanecarboxylic acid (387 mg, 3 mmol) and NaOH (132 mg, 3.3 mmol) in tert-butanol (3.3 mL) and water (3 ml) was added (Boc)$_2$O (655 mg, 3 mmol). The reaction mixture was stirred from 0° C. to room temperature for 1 hour. The mixture was washed with hexane (3 times), acidified with 1N HCl to pH=3, and extracted with ethyl acetate (3 times). The organic layer was dried (sodium sulfate), filtered, concentrated under reduced pressure and purified by flash chromatography with 30% ethyl acetate/hexane to provide the titled compound. MS (ESI) m/z 230 (M+H)$^+$.

Example 191B (1S,3R)-{3-[(pyridin-2-ylmethyl)-carbamoyl]-cyclopentyl}-carbamic acid tert-butyl ester To a solution of (1S,3R)-3-tert-butoxycarbonylamino-cyclopentanecarboxylic acid (91.6 mg, 0.4 mmol) in DMF (4 ml) was added pycoylamine (0.045 ml, 0.44 mmol), 1-[3-(dimethylamino)propyl]-3-ethylcarbodiimide hydrochloride (EDAC), (93 mg, 0.48 mmol), 1-hydroxybenzotriazole (HOBT), (82 mg, 0.6 mmol), and diisopropylethylamine (0.35 ml, 2 mmol). The mixture was stirred at room temperature for 16 hours. The mixture was diluted with ethyl acetate, washed with water (2 times) and brine. The organic layer was dried (sodium sulfate), filtered, concentrated under reduced pressure and purified by flash chromatography with 3% methanol/dichloromethane to provide the titled compound. MS (ESI) m/z 320 (M+H)$^+$.

Example 191

(1S,3R)-3-({2-[(2S,5R)-2-cyano-5-ethynylpyrrolidin-1-yl]-2-oxoethyl}amino)-N-(pyridin-2-ylmethyl)cyclopentanecarboxamide (1S,3R)-{3-[(pyridin-2-ylmethyl)-carbamoyl]-cyclopentyl}-carbamic acid tert-butyl ester (66 mg, 0.21 mmol) was dissolved in 4N HCl/dioxane (1 ml) and the mixture was stirred at room temperature for 1 hour. The mixture was concentrated under reduced pressure. The residue was taken up in acetonitrile (1 ml), Example 8D (21 mg, 0.103 mmol) and diisopropylethylamine (0.091 ml, 0.52 mmol) were added. The mixture was stirred at room temperature for 48 hours, concentrated under reduced pressure and purified by HPLC to provide the titled compound. MS (ESI) m/z 380 (M+H)$^+$; $^1$H NMR (300 MHz, MeOH-d$_4$) δ ppm 8.63 (dd, 1H), 8.20 (m, 1H), 7.66 (m, 2H), 4.62 (s, 2H), 4.20 (AB quartet, 2H), 3.81-3.68 (m, 2H), 2.46-1.94 (m, 7H), 1.37 (m, 6H).

Example 192

(1S,3R)-3-({2-[(2S,5R)-2-cyano-5-ethynylpyrrolidin-1-yl]-2-oxoethyl}amino)-N-quinolin-2-ylcyclopentanecarboxamide

Example 192A (1S,3R)-[3-(quinolin-2-ylcarbamoyl)-cyclopentyl]-carbamic acid tert-butyl ester To a solution of Example 191A (91.6 mg, 0.4 mmol) in DMF (4 ml) was added 2-aminoquinoline (64 mg, 0.44 mmol), EDAC (93 mg, 0.48 mmol), HOBT (82 mg, 0.6 mmol), and diisopropylethylamine (0.35 ml, 2 mmol). The mixture was stirred at room temperature overnight, diluted with ethyl acetate, washed with water (2 times) and brine. The organic layer was dried (sodium sulfate), filtered, concentrated under reduced pressure and purified by flash chromatography with 3% methanol/dichloromethane to provide the titled compound. MS (ESI) m/z 356 (M+H)$^+$.

Example 192

(1S,3R)-3-({2-[(2S,5R)-2-cyano-5-ethynylpyrrolidin-1-yl]-2-oxoethyl}amino)-N-quinolin-2-ylcyclopentanecarboxamide A mixture of (1S,3R)-[3-(quinolin-2-ylcarbamoyl)-cyclopentyl]-carbamic acid tert-butyl ester (71 mg, 0.2 mmol) in 4N HCl/dioxane (1 ml) was stirred at room temperature for 1 hour. The mixture was concentrated under reduced pressure, taken up in acetonitrile (1 ml), Example 8D (20 mg, 0.1 mmol) and diisopropylethylamine (0.087 ml, 0.5 mmol) were added. The mixture was stirred at room temperature for 48 hours, concentrated under reduced pressure and purified by HPLC to provide the titled compound. MS (ESI) m/z 416 (M+H)+; 1H NMR (300 MHz, MeOH-d4) δ ppm 8.63 (dd, 1H), 8.20 (m, 1H), 7.66 (m, 2H), 4.29-4.20 (m, 2H), 3.80-3.70 (m, 2H), 2.96 (m, 1H), 2.49-1.8 (m, 12H).

Example 193

(2S,5R)-5-ethynyl-1-({[4-methyl-1-(5-nitropyridin-2-yl)piperidin-4-yl]amino}acetyl)pyrrolidine-2-carbonitrile

Example 193A

A solution of (4-methyl-piperidin-4-yl)-carbamic acid benzyl ester hydrochloride salt (2.40 g, 8.45 mmol, Example 30B), 2-chloro-5-nitropyridine (1.45 g, 9.15 mmol) and diisopropylethylamine (5.2 mL) in dioxane (10 mL) in a sealed tube was heated to 82° C. overnight. The mixture was cooled, concentrated and then purified by chromatography (silica gel, eluting with 15% hexane/ethyl acetate to 30% ethyl acetate/hexane) to provide the titled compound (2.75 g) as a yellow solid. MS (CI) m/z 371 (M+1)+; 1H NMR (300 MHz, CDCl3) δ ppm 9.03 (d, 1H), 8.20 (dd, 1H), 7.37 (m, 5H), 6.57 (dd, 1H), 5.08 (s, 2H), 4.68 (bs, 1H), 4.13-4.05 (m, 2H), 3.51-3.42 (m, 2H), 2.20-2.14 (m, 2H), 1.72-1.62 (m, 2H), 1.43 (s, 3H).

Example 193B

4-Methyl-5'-nitro-3,4,5,6-tetrahydro-2H-[1,2']bipyridinyl-4-ylamine

To a stirred solution of Example 193A (0.36 g, 0.97 mmol) in acetonitrile (7.0 mL) at room temperature was added iodotrimethysilane (0.25 mL, 1.5 mmol). The mixture was stirred at 50° C. for 30 minutes and then concentrated under reduced pressure. The solid residue was washed with acetone and ether and filtered to provide titled compound (0.18 g). MS (CI) m/z 237 (M+1)+; 1H NMR (300 MHz, CD3OD) δ ppm 8.96 (d, 1H), 8.21 (dd, 1H), 6.85 (d, 1H), 4.79 (m, 1H), 3.94-3.74 (m, 4H), 1.69-1.55 (m, 4H), 1.21 (s, 3H).

Example 193

(2S,5R)-5-ethynyl-1-({[4-methyl-1-(5-nitropyridin-2-yl)piperidin-4-yl]amino}acetyl)pyrrolidine-2-carbonitrile A mixture of Example 193B (180 mg, 0.77 mmol) and (2S,5R)-1-(chloroacetyl)-5-ethynylpyrrolidine-2-carbonitrile (156 mg, 0.8 mmol, Example 8D) and diisopropylethylamine (0.2 mL) in acetonitrile (10 mL) was stirred at 23° C. for 72 hours. The mixture was concentrated under reduced pressure, and the crude residue was purified by chromatography (silica gel, eluting with 96% dichloromethane/4% methanol/0.1% ammonium hydroxide) to provide the compound as a yellow foam. The product was mixed with 4M HCl in dioxane (4 mL) and after 0.5 hour, the solvents were removed under reduced pressure, and the residue was solidified by trituration with diethyl ether filtered to provide the titled compound as the HCl salt. MS (CI) m/z 397 (M+1)+; 1H NMR (300 MHz, methanol-d4) δ ppm 8.96 (d, 1H), 8.20 (dd, 1H), 6.82 (d, 1H), 5.01 (bs, 1H), 4.81-4.72 (m, 2H), 4.53-4.37 (m, 2H), 3.97-3.89 (m, 2H), 3.80-3.72 (m, 3H), 3.62-3.56 (m, 1H), 3.09 (dd, 1H), 2.43-2.24 (m, 4H), 1.75-1.61 (m, 2H), 1.21 (m, 3H).

Example 194

(2S,5R)-5-ethynyl-1-[({4-methyl-1-[5-(methylsulfonyl)pyridin-2-yl]piperidin-4-yl}amino)acetyl]pyrrolidine-2-carbonitrile

Example 194A 2-bromo-5-(methylsulfonyl)pyridine

To a solution of 2,5-dibromopyridine (5 g, 21.1 mmol) in THF (20 mL) at 0° C. was slowly added 2M isopropylmagnesium chloride in THF (14.4 ml). The mixture was stirred at 0° C. for 1 hour, cooled to −15° C. followed by the dropwise addition of methane sulfonyl chloride in 5 mL THF. The mixture was slowly warmed up to room temperature, diluted with water (5 mL) and t-butylmethyl ether (3×50 mL). The layers were separated and the aqueous layer extracted with t-butylmethyl ether (2×). The combined organic layers were washed with brine, dried MgSO4, filtered and concentrated under reduced pressure and purified by chromatography (silica gel, eluting with 30% hexane-70% ethyl acetate) to provide the titled compound. MS (CI) m/z 237 (M+1)+, 254 (M+NH4)+ 1H NMR (300 MHz, CDCl3) δ ppm: 8.92 (d, 1H), 8.06 (dd, 1H), 7.73 (d, 1H), 3.12 (s, 1H).

Example 194B

5'-Methanesulfonyl-4-methyl-3,4,5,6-tetrahydro-2H-[1,2']bipyridinyl-4-ylamine

A solution of (4-methyl-piperidin-4-yl)-carbamic acid benzyl ester hydrochloride salt (0.37 g, 1.3 mmol, Example 30B), 2-bromo-5-(methylsulfonyl)pyridine (0.27 g, 1.15 mmol) and diisopropylethylamine (0.7 mL) in dioxane (4 mL) in a sealed tube was heated to 80° C. for 16 hours. The mixture was cooled, concentrated under reduced pressure and purified by chromatography (silica gel, eluting with 5% hexane/ethyl acetate to 25% ethyl acetate/hexane) to provide the titled compound (0.225 g) as a white solid. MS (CI) m/z 404 (M+1)+; 1H NMR (300 MHz, CDCl3) δ ppm 8.63 (d, 1H), 7.86 (dd, 1H), 7.37 (m, 5H), 6.65 (d, 1H), 5.07 (s, 2H), 4.67 (s, 1H), 4.04-3.96 (m, 2H), 3.49-3.39 (m, 2H), 3.03 (s, 3H), 2.19-2.12 (m, 2H), 1.71-1.61 (m, 2H), 1.41 (s, 3H).

Example 194C 4-(4-Amino-4-methyl-piperidine-1-carbonyl)-benzoic acid methyl ester A mixture of Example 194B (0.22 g, 0.55 mmol) and ammonium formate (0.14 g, 2.2 mmol) in isopropanol (5.0 mL) was stirred at 80° C. for 30 minutes, filtered through Celite and concentrated under reduced pressure. The solid residue was dried to provide titled compound (0.11 g). MS (CI) m/z 270 (M+1)+; $^1$H NMR (300 MHz, DMSO-$d_6$) δ ppm 8.62 (d, 1H), 7.83 (dd, 1H), 6.65 (d, 1H), 3.88-3.80 (m, 2H), 3.73-3.64 (m, 4H), 3.03 (s, 3H), 1.79-1.58 (m, 4H), 1.35 (s, 3H).

Example 194

(2S,5R)-5-ethynyl-1-(N-(4-methyl-1-[5-(methanesulfonyl)pyridin-2-yl]piperidin-4-yl)amino)pyrrolidine-2-carbonitrile A mixture of Example 194C (110 mg, 0.41 mmol) and (2S,5R)-1-(chloroacetyl)-5-ethynylpyrrolidine-2-carbonitrile (90 mg, 0.45 mmol, Example 8D) in acetonitrile (2 mL) with diisopropylethylamine (0.2 mL) was stirred at 23° C. for 72 hours. The mixture was concentrated under reduced pressure, and the crude residue was purified by chromatography (silica gel, eluting with 96% dichloromethane/4% methanol/ 0.1% ammonium hydroxide) to provide the compound as glassy solid. The product was mixed with 4M HCl in dioxane (4 mL) and after 0.5 hour, the solvents were removed under reduced pressure, and the residue was solidified by trituration with diethyl ether to provide the titled compound as the HCl salt (61 mg). MS (CI) m/z 430 (M+1)+; $^1$H NMR (300 MHz, methanol-$d_4$) δ ppm: 8.52 (d, 1H), 8.15 (d, 1H), 7.29 (m, 1H), 4.91 (m, 2H), 4.82 (m, 1H), 4.50-4.48 (m, 2H), 4.36-4.13 (q, 2H), 3.66 (s, 3H), 3.47-3.37 (m, 2H), 3.23 (m, 1H), 2.50-2.31 (m, 4H), 2.12-2.02 (m, 4H), 1.61 (s, 3H).

Example 195 methyl (1S,3R)-3-({2-[(2S,5R)-2-cyano-5-ethynylpyrrolidin-1-yl]-2-oxoethyl}amino)cyclopentanecarboxylate Example 195A (1S,3R)-3-tert-butoxycarbonylamino-cyclopentanecarboxylic acid methyl ester To a cold solution (0° C.) of Example 191A (458 mg, 2 mmol) in THF (2 ml)/MeOH (2 ml) was added TMSCHN$_2$ (2 ml, 2N in hexane). The mixture was stirred at room temperature for 2 hours, concentrated under reduced pressure and purified by flash chromatography with 30% acetone/hexane to provide the titled compound. MS (ESI) m/z 244 (M+H)+.

Example 195 methyl (1S,3R)-3-({2-[(2S,5R)-2-cyano-5-ethynylpyrrolidin-1-yl]-2-oxoethyl}amino)cyclopentanecarboxylate (1S,3R)-3-tert-butoxycarbonylamino-cyclopentanecarboxylic acid methyl ester (149 mg, 0.61 mmol) in 4N HCl/ dioxane (1 ml) was stirred for 1 hour and concentrated under reduced pressure. The residue was taken up in acetonitrile (1 ml) followed by the addition of Example 8D (60 mg, 0.31 mmol) and diisopropylethylamine (0.27 ml, 1.53 mmol). The mixture was stirred at room temperature for overnight, concentrated under reduced pressure and purified by HPLC to provide the titled compound. MS (ESI) m/z 304 (M+H)+; $^1$H NMR (300 MHz, MeOH-$d_4$) δ ppm, 4.73 (m, 1H), 4.66 (m, 1H), 3.68 (s, 3H), 3.69-3.52 (m, 2H), 2.79 (m, 1H), 2.40-1.54 (m, 12H).

Example 196

(2R,5S)-1-[(tert-butylamino)acetyl]pyrrolidine-2,5-dicarbonitrile

Example 196A (2R,5S)-1-[2-(tert-Butoxycarbonyl-tert-butylamino)-acetyl]-pyrrolidine-2,5-dicarboxylic acid diethyl ester Example 196A was prepared in the same way as Example 1F by substituting diethyl ester-(2R,5S)-2,5-pyrrolidinedicarboxylic acid (*Gazetta Chimica Italiana* 1962, 92, 1093) for methyl (5R)-5-((trimethylsilyl)ethynyl)-L-prolinate and N-[(1,1-Dimethylethoxy)carbonyl]-N-(1,1-dimethylethyl) glycine methyl ester for N-(tert-butoxycabonyl)-L-leucine monohydrate. MS (CI) m/z 429.2 (M+1)+; $^{13}$C NMR (100 MHz, CDCl$_3$) δ ppm 171.1, 170.6, 169.6, 79.7, 61.6, 60.9, 59.9, 59.4, 55.62, 47.2, 29.8, 29.5, 28.4, 27.4, 14.0.

Example 196B (2R,5S)-1-[2-(tert-Butoxycarbonyl-tert-butylamino)-acetyl]-pyrrolidine-2,5-dicarboxylic acid dicarboxylic acid Example 196B was prepared in the same way as Example 1G by substituting Example 197A for methyl N-(tert-butoxycarbonyl)-L-leucyl-(5R)-5-((trimethylsilyl)ethynyl)-L-prolinate. MS (CI) m/z 374.4 (M+1)+; $^{13}$C NMR (100 MHz, CDCl$_3$) δ ppm 175.5, 174.1, 81.0, 60.7, 60.1, 56.0, 47.3, 30.5, 29.4, 28.4, 27.1.

Example 196C (2R,5S)-1-[2-(tert-Butoxycarbonyl-tert-butylamino)-acetyl]-pyrrolidine-2,5-dicarboxylic acid dicarboxamide Example 196C was prepared in the same way as Example 1H by substituting Example 197B for N-(tert-butoxycarbonyl)-L-leucyl-(5R)-5-ethynyl-L-proline. MS (ESI) m/z 369.3 (M−1)+; $^1$H NMR (100 MHz, CD$_3$OD) δ ppm 177.7, 177.5, 171.4, 81.3, 63.0, 62.5, 57.0, 48.3, 32.6, 29.6, 28.8.

Example 196D (2R,5S)-1-[2-(tert-Butoxycarbonyl-tert-butylamino)-acetyl]-pyrrolidine-2,5-dicarboxylic acid dicarbonitrile Example 196D was prepared in the same way as Example 1I by substituting Example 197C for N-(tert-butoxycarbonyl)-L-leucyl-(5R)-5-ethynyl-L-prolinamide. MS (CI) m/z 335 (M+1)+; $^{13}$C NMR (100 MHz, CD$_3$OD) δ ppm 171.1, 156.8, 118.9, 81.6, 57.2, 48.0, 32.3, 29.7, 29.6, 28.7.

Example 196

(2R,5S)-1-[(tert-butylamino)acetyl]pyrrolidine-2,5-dicarbonitrile

Example 196 was prepared in the same way as Example 1 by substituting Example 197D for N-(tert-butoxycarbonyl)-L-leucyl-(5R)-5-ethynyl-L-pyrrolidine-2-carbonitrile. MS (CI) m/z 235 (M+1)+; 13C NMR (100 MHz, CD3OD) δ ppm 165.8, 118.6, 58.7, 48.3, 44.3, 32.1, 29.8, 25.8.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I),

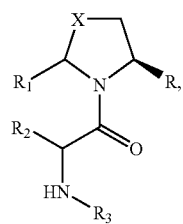

or pharmaceutically acceptable salt or prodrug thereof, wherein

X is a member selected from the group consisting of CH2, CHF and CF2;

R is selected from the group consisting of alkylcarbonyl, arylcarbonyl, cyano, heterocyclecarbonyl, R4R5NC(O)—, B(OR6)2, (1,2,3)-dioxoborolane and 4,4,5,5-tetramethyl(1,2,3)-dioxoborolane;

R1 is selected from the group consisting of alkoxyalkyl, alkyl, alkylcarbonyl, alkenyl, alkynyl, allenyl, arylalkyl, cycloalkyl, cycloalkylalkyl, cyano, haloalkyl, haloalkenyl, heterocyclealkyl, and hydroxyalkyl;

R2 and R3 are independently selected from the group consisting of hydrogen, alkoxyalkyl, alkyl, alkenyl, alkynyl, cycloalkyl, cycloalkylalkyl, aryl, arylalkyl, heterocycle, heterocyclealkyl, hydroxyalkyl; or R2 and R3 taken together with the atoms to which they are attached form a mono or bicyclic heterocycle selected from the group consisting of 2-indolinyl, 2-indolyl, 3-isoquinoline, 2-piperazine, 2-piperidine, 2-pyrrolidine, 2-pyrrole, 2-pyridine, 2-quinolinyl, 2-tetrahydroquinolinyl, and 3-tetrahydroisoquinolinyl, wherein said heterocycle may be substituted with 0, 1, 2 or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, hydroxy, hydroxyalkyl, mercapto, nitro, phenyl, R$_A$R$_B$N—, RcR$_D$NC(0)-, and RcR$_D$NS(0)2—;

R4, R5 and R6 are each independently selected from the group consisting of hydrogen, alkyl, and arylalkyl;

R$_A$ and R$_B$ are each independently selected from the group consisting of alkyl, alkylcarbonyl, alkoxycarbonyl, alkylsulfonyl; or R$_A$ and R$_B$ taken together with the nitrogen to which they are attached form a ring selected from the group consisting of piperidine, piperazine and morpholine; and Rc and R$_D$ are each independently selected from the group consisting of hydrogen and alkyl.

2. The compound according to claim 1, wherein
R is cyano.

3. The compound according to claim 1, wherein
R is cyano; and
R1 is a member selected from the group consisting of alkyl, alkenyl, and alkynyl.

4. The compound according to claim 1, wherein
R is cyano;
R1 is a member selected from the group consisting of alkyl, alkenyl, and alkynyl; and
R2 is a member selected from the group consisting of alkoxyalkyl, alkyl, cycloalkyl, cycloalkylalkyl, arylalkyl, and heterocyclealkyl.

5. The compound according to claim 1, wherein
R is cyano;
R1 is a member selected from the group consisting of alkyl, alkenyl, and alkynyl; and
R2 is a member selected from the group consisting of hydrogen, alkyl, cycloalkyl, and heterocycle; and
R3 is hydrogen.

6. The compounds according to claim 5, that is a member selected from the group consisting of
(2S,5R)-5-ethynyl-1-L-leucylpyrrolidine-2-carbonitrile;
(2S,5R)-1-{(2S)-2-amino-2-cyclopentylethanoyl)-5-ethynylpyrrolidine-2-carbonitrile;
(2S,5R)-1-{(2S)-2-amino-2-cyclopentylethanoyl)-5-vinylpyrrolidine-2-carbonitrile;
(2S,5R)-1-((2S)-2-amino-2-cyclohexylethanoyl)-5-ethynylpyrrolidine-2-carbonitrile;
(2S,5S)-5-ethyl-1-L-leucylpyrrolidine-2-carbonitrile;
(2S,5S)-1-((2S)-2-amino-2-cyclohexylethanoyl)-5-ethylpyrrolidine-2-carbonitrile;
(2S,5S)-1-L-leucy1-5-methylpyrrolidine-2-carbonitrile;
(2S,5R)-5-ethynyl-1-L-leucylpyrrolidine-2-carbonitrile;
(2S,5R)-1-((2S)-2-amino-2-cyclopentylethanoyl)-5-ethynylpyrrolidine-2-carbonitrile;
(2S,5R)-1-((2R)-2-amino-2-cyclohexylethanoyl)-5-ethynylpyrrolidine-2-carbonitrile;
(2S,5S)-1-((2S)-2-amino-2-cyclopentylethanoyl)-5-methylpyrrolidine-2-carbonitrile;
(2S,5R)-1-((2S)-2-amino-2-cyclopentylethanoyl)-5-prop-1-ynylpyrrolidine-2-carbonitrile;
(2S,5S)-4,4-difluoro-5-methyl-1-L-valylpyrrolidine-2-carbonitrile;
(2S,5S)-4,4-difluoro-1-L-leucyl-5-methylpyrrolidine-2-carbonitrile;
(2S,5R)-1-((2S)-2-amino-2-cyclohexylethanoyl)-5-vinylpyrrolidine-2-carbonitrile;
(2S,5R)-1-[((2R)-2-amino-2-cyclopentylethanoyl)-5-vinylpyrrolidine-2-carbonitrile;
(2S,5R)-5-ethynyl-1-(2-methyl-L-valyl)pyrrolidine-2-carbonitrile;
(2S,5R)-5-ethynyl-1-(3-pyridin-4-yl-L-alanyl)pyrrolidine-2-carbonitrile;
(2S,5R)-1-L-leucyl-5-prop-1-ynylpyrrolidine-2-carbonitrile;
(2S,5R)-1-(3-methyl-L-valyl)-5-prop-1-ynylpyrrolidine-2-carbonitrile;
(2S,5S)-1-L-isoleucyl-5-methylpyrrolidine-2-carbonitrile;
(2S,5S)-1-(3-cyclopropyl-L-alanyl)-5-methylpyrrolidine-2-carbonitrile;
(2S,5S)-5-methyl-1-L-valylpyrrolidine-2-carbonitrile;
(2S,5S)-5-methyl-1-(4-methyl-L-leucyl)pyrrolidine-2-carbonitrile;
(2S,5S)-1-(3-cyclohexyl-L-alanyl)-5-methylpyrrolidine-2-carbonitrile.

7. The compound according to claim 1, wherein
R is cyano;
R1 is a member selected from the group consisting of alkyl, alkenyl, and alkynyl; and
R2 is hydrogen; and
R3 is cycloalkyl, wherein cycloalkyl is a member selected from the group consisting of cyclopropyl, cyclobutyl, cyclopentyl, cycloheptyl, and cyclooctyl.

8. The compound according to claim 7, that is a member selected from the group consisting of
(2S,5R)-1-{N-((1R,2R,4S)-bicyclo(2.2.1)hept-2-yl)glycyl}-5-ethynylpyrrolidine-2-carbonitrile;
(2S,5R)-1-{N-((1R,4S)-bicyclo[2.2.1]hept-2-yl)glycyl}-5-ethynylpyrrolidine-2-carbonitrile;
(2S,5R)-1-(N-1-adamantylglycyl)-5-ethynylpyrrolidine-2-carbonitrile;
(2S,5R)-1-(N-cyclohexylglycyl)-5-ethynylpyrrolidine-2-carbonitrile;
(2S,5R)-5-ethynyl-1-{N-(1-(methoxymethyl)cyclopentyl)glycyl}pyrrolidine-2-carbonitrile;
(2S,5R)-1-(N-cyclopentylglycyl)-5-ethynylpyrrolidine-2-carbonitrile;
(2S,5R)-5-ethynyl-1-{N-((2S)-2-hydroxycyclopentyl)glycyl}pyrrolidine-2-carbonitrile;
(2S,5R)-1-(N-cyclopentylglycyl)-5-ethynylpyrrolidine-2-carbonitrile;
(2S,5R)-5-ethynyl-1-{N-(1-(hydroxymethyl)cyclopentyl)glycyl}pyrrolidine-2-carbonitrile;
(2S,5R)-1-{N-(1-(hydroxymethyl)cyclopentyl)glycyl}-5-prop-1-ynylpyrrolidine-2-carbonitrile;
(2S,5R)-1-(N-cyclopentylglycyl)-5-prop-1-ynylpyrrolidine-2-carbonitrile;
(2S,5S)-1-(N-cyclopentylglycyl)-5-methylpyrrolidine-2-carbonitrile;
(2S,5S)-1-{N-(1-(hydroxymethyl)cyclopentyl)glycyl}-5-methylpyrrolidine-2-carbonitrile;
(2S,5S)-1-{N-((2R,5S)-hexahydro-2,5-methanopentalen-3a(1H)-yl)glycyl}-5-methylpyrrolidine-2-carbonitrile;
(2S,5R)-5-ethynyl-1-{N-(1-(1-hydroxy-1-methylethyl)cyclopentyl)glycyl]pyrrolidine-2-carbonitrile;
(2S,5R)-5-ethynyl-1-{N-((2R,5S)-hexahydro-2,5-methanopentalen-3a(1H)-yl)glycyl}pyrrolidine-2-carbonitrile;
(2S,5R)-1-(N-cyclopentylglycyl-(N-methyl 1-aminocyclopentanecarboxy)-5-ethynylpyrrolidine-2-carbonitrile;
(2S,5R)-1-(N-cyclopropylglycyl)-5-ethynylpyrrolidine-2-carbonitrile;
(2S,5R)-5-ethynyl-1-{N((5R,7S)-3-hydroxy-1-adamantyl)glycyl}pyrrolidine-2-carbonitrile;
(2S,5R)-1-(N-cycloheptylglycyl)-5-ethynylpyrrolidine-2-carbonitrile;
(2S,5R)-1-(N-cyclobutylglycyl)-5-ethynylpyrrolidine-2-carbonitrile;
(2S,5R)-1-(N-cyclobutylglycyl)-5-prop-1-ynylpyrrolidine-2-carbonitrile;
(2S,5R)-1-{N-((2S)-2-hydroxycyclopentyl)glycyl}-5-prop-1-ynylpyrrolidine-2-carbonitrile;
(2S,5S)-5-methyl-1-{N-((1S,2S,3S,5R)-2,6,6-trimethylbicyclo[3.1.1]hept-3-yl)glycyl}pyrrolidine-2-carbonitrile;
(2S,5S)-1-{N((5R,7S)-3-hydroxy-1-adamantyl)glycyl}-5-methylpyrrolidine-2-carbonitrile;
(1S,3R)-3-({2-[(2S,5R)-2-cyano-5-ethynylpyrrolidin-1-yl]-2-oxoethyl}amino)-N-(pyridin-2-ylmethyl)cyclopentanecarboxamide;
(1S,3R)-3-({2-[(2S,5R)-2-cyano-5-ethynylpyrrolidin-1-yl]-2-oxoethyl}amino)-N-quinolin-2-ylcyclopentanecarboxamide; and
methyl (1S,3R)-3-({2-[(2S,5R)-2-cyano-5-ethynylpyrrolidin-1-yl]-2-oxoethyl}amino)cyclopentanecarboxylate.

9. The compound according to claim 1, wherein
R is cyano,
R1 is a member selected from the group consisting of alkyl, alkenyl, and alkynyl; and
R2 is hydrogen; and
R3 is R7 is a member selected from the group consisting of hydrogen and alkyl; and
R9 is a member selected from the group consisting of hydrogen, aryl, and heterocycle.

10. The compound according to claim 9, that is a member selected from the group consisting of
(2S,5R)-5-ethynyl-1-(N-(4-trans-hydroxycyclohexyl)glycyl)pyrrolidine-2-carbonitrile;
(2S,5R)-5-ethynyl-1-(N-(4-trans-{(4'-fluoro-5-(trifluoromethyl)-1,1'-biphenyl-2-yl)oxy}cyclohexyl)glycyl)pyrrolidine-2-carbonitrile;
(2S,5R)-5-ethynyl-1-(N-{4-trans (4-(trifluoromethoxy)phenoxy)cyclohexyl}glycyl)pyrrolidine-2-carbonitrile;
(2S,5R)-5-ethynyl-1-(N-(4-hydroxy-1-methylcyclohexyl)glycyl)pyrrolidine-2-carbonitrile;
(2S,5R)-5-ethynyl-1-{N-(1-methyl-4-trans(pyridin-3-yloxy)cyclohexyl)glycyl}pyrrolidine-2-carbonitrile;
(2S,5R)-1-(N-4-trans((5-chloropyridin-3-yl)oxy)cyclohexyl}glycyl)-5-ethynylpyrrolidine-2-carbonitrile;
(2S,5R)-1-{N-(4-trans(4-cyanophenoxy)cyclohexyl)glycyl}-5-ethynylpyrrolidine-2-carbonitrile;
(2S,5R)-5-ethynyl-1-(N-(4-trans{(5-(trifluoromethyl)pyridin-2-yl)oxy}cyclohexyl)glycyl)pyrrolidine-2-carbonitrile;
(2S,5R)-5-ethynyl-1-(N-{4-trans(3-pyridin-4-yl-4-(trifluoromethyl)phenoxy)cyclohexyl}glycyl)pyrrolidine-2-carbonitrile;
(2S,5R)-5-ethynyl-1-{N-(4-trans(pyridin-2-yloxy)cyclohexyl)glycyl}pyrrolidine-2-carbonitrile;
(2S,5R)-5-ethynyl-1-{N-(1-methyl-4-trans(5-cyano-pyridin-2-yloxy)cyclohexyl)glycyl}pyrrolidine-2-carbonitrile;
(2S,5R)-5-ethynyl-1-{N-(4-trans(pyrimidin-2-yloxy)cyclohexyl)glycyl}pyrrolidine-2-carbonitrile;
(2S,5R)-5-ethynyl-1-{N-(4-trans(5-cyano-pyridin-2-yloxy)cyclohexyl)glycyl}pyrrolidine-2-carbonitrile;
(2S,5R)-5-ethynyl-1-(N-{4-trans(4-(trifluoromethyl)phenoxy)cyclohexyl}glycyl)pyrrolidine-2-carbonitrile;

(2S,5R)-5-ethynyl-1-(N-{4-((5-fluoropyridin-3-yl)oxy)-1-methylcyclohexyl}glycyl)pyrrolidine-2-carbonitrile;
(2S,5R)-5-ethynyl-1-(N-(4-trans(4-carboxy-phenoxy)cyclohexyl)glycyl)pyrrolidine-2-carbonitrile;
(2S,5R)-5-ethynyl-1-(N-{4-trans(2-(2-oxopyrrolidin-1-yl)-4-(trifluoromethyl)phenoxy)cyclohexyl}glycyl)pyrrolidine-2-carbonitrile;
(2S,5R)-1-{N-(4-trans(4-cyano-2-methoxyphenoxy)cyclohexyl)glycyl}-5-ethynylpyrrolidine-2-carbonitrile;
(2S,5R)-1-(N-{4-trans((5-chloropyridin-2-yl)oxy)cyclohexyl}glycyl)-5-ethynylpyrrolidine-2-carbonitrile;
(2S,5R)-5-ethynyl-1-{N-(1-methyl-4-trans(pyridin-2-yloxy)cyclohexyl)glycyl}pyrrolidine-2-carbonitrile;
(2S,5R)-5-ethynyl-1-(N-{4-trans((5-fluoropyridin-3-yl)oxy)cyclohexyl}glycyl)pyrrolidine-2-carbonitrile;
(2S,5R)-1-(N-{4-trans((5-bromopyridin-2-yl)oxy)cyclohexyl}glycyl)-5-ethynylpyrrolidine-2-carbonitrile;
(2S,5R)-5-ethynyl-1-{N-(4-trans(pyridin-3-yloxy)cyclohexyl)glycyl}pyrrolidine-2-carbonitrile;
(2S,5R)-5-prop-1-ynyl-1-(N-{4-(4-(trifluoromethyl)phenoxy)cyclohexyl}glycyl)pyrrolidine-2-carbonitrile;
(2S,5R)-1-{N-(4-trans(4-cyano-2-fluorophenoxy)cyclohexyl)glycyl}-5-ethynylpyrrolidine-2-carbonitrile;
(2S,5R)-5-ethynyl-1-{N-(4-trans(3-fluorophenoxy)-1-methylcyclohexyl)glycyl}pyrrolidine-2-carbonitrile;
(2S,5R)-1-{N-(4-trans(3-cyanophenoxy)cyclohexyl)glycyl}-5-ethynylpyrrolidine-2-carbonitrile;
(2S,5R)-5-ethyny1-1-(N-(1-methy 1-4-{(5-(trifluoromethyl)pyridin-2-yl)oxy}cyclohexyl)glycyl)pyrrolidine-2-carbonitrile;
(2S,5R)-1-(N-{4-trans((5-chloropyridin-2-yl)oxy)cyclohexyl}glycyl)-5-ethynylpyrrolidine-2-carbonitrile;
(2S,5R)-5-ethynyl-1-(N-(4-trans{(4'-fluoro-2-(trifluoromethyl)-1,1'-biphenyl-4-yl)oxy}cyclohexyl)glycyl)pyrrolidine-2-carbonitrile;
(2S,5R)-5-ethynyl-1-(N-(4-trans{(4'-fluoro-6-(trifluoromethyl)-1,1'-biphenyl-3-yl)oxy}cyclohexyl)glycyl)pyrrolidine-2-carbonitrile;
(2S,5R)-1-(N-{4-(3-cyano-4-trans(trifluoromethyl)phenoxy)cyclohexyl}glycyl)-5-ethynylpyrrolidine-2-carbonitrile;
(2S,5R)-1-{N-(4-trans(3-bromophenoxy)cyclohexyl)glycyl}-5-ethynylpyrrolidine-2-carbonitrile;
(2S,5R)-1-{N-(4-trans(4-cyano-3-fluorophenoxy)cyclohexyl)glycyl}-5-ethynylpyrrolidine-2-carbonitrile;
(2S,5R)-1-(N-{4-(2-cyano-4-trans(trifluoromethyl)phenoxy)cyclohexyl}glycyl)-5-ethynylpyrrolidine-2-carbonitrile;
(2S,5R)-1-{N-(4-trans(3-cyanophenoxy)-1-methylcyclohexyl)glycyl}-5-ethynylpyrrolidine-2-carbonitrile;
(2S,5R)-1-{N-(4-trans(4-chlorophenoxy)cyclohexyl)glycyl}-5-ethynylpyrrolidine-2-carbonitrile;
(2S,5R)-5-ethynyl-1-(N-(4-trans{(6-methyl-4-(trifluoromethyl)pyridin-2-yl)oxy}cyclohexyl)glycyl)pyrrolidine-2-carbonitrile;
(2S,5R)-1-(N-{4-trans(2-cyano-3-(trifluoromethyl)phenoxy)cyclohexyl}glycyl)-5-ethynylpyrrolidine-2-carbonitrile;
(2S,5R)-5-ethynyl-1-{N-{4-trans(4-pyridin-4-yl-3-(trifluoromethyl)phenoxy)cyclohexyl}glycyl}pyrrolidine-2-carbonitrile;
(2S,5R)-1-(N-{4-trans(3-cyano-5-(trifluoromethyl)phenoxy)cyclohexyll glycyl)-5-ethynylpyrrolidine-2-carbonitrile;
(2S,5R)-5-ethynyl-1-{N-(4-(4-fluorophenoxy)-1-methylcyclohexyl)glycyl}pyrrolidine-2-carbonitrile;
(2S,5R)-5-ethynyl-1-{N-(4-(3-fluorophenoxy)-1-methylcyclohexyl)glycyl}pyrrolidine-2-carbonitrile;
(2S,5R)-5-ethynyl-1-(N-(1-methyl-4-{(5-(trifluoromethyl)pyridin-2-yl)oxy}cyclohexyl)glycyl)pyrrolidine-2-carbonitrile;
(2S,5R)-5-ethynyl-1-(N-{4-trans3-(tri fluoromethyl)phenoxy)cyclohexyl)glycyl)pyrrolidine-2-carbonitrile;
(2S,5R)-1-(N-{4-trans((3-bromopyridin-2-yl)oxy)cyclohexyl}glycyl)-5-ethynylpyrrolidine-2-carbonitrile;
(2S,5R)-5-ethynyl-1-(N-(4-trans{(4-(trifluoromethyl)pyridin-2-yl)oxy}cyclohexyl)glycyl)pyrrolidine-2-carbonitrile;
(2S,5R)-1-(N-{4-trans((5-chloropyridin-2-yl)oxy)-1-methylcyclohexyllglycyl)-5-ethynylpyrrolidine-2-carbonitrile;
(2S,5R)-1-{N-(4-trans(3-cyanophcnoxy)-1-methylcyclohcxyl)glycyl}-5-ethynylpyrrolidine-2-carbonitrile;
(2S,5R)-5-ethynyl-1-(Ar-{4-trans(2-carboxy-4-(trifluoromethyl)phenoxy)cyclohexyl}glycyl)pyrrolidine-2-carbonitrile;
(2S,5R)-1-{N-(4-trans(3-chlorophenoxy)cyclohexyl)glycyl}-5-ethynylpyrrolidine-2-carbonitrile;
(2S,5R)-5-ethynyl-1-(N-(1-methy 1-4-trans{(5-(trifluoromethyl)pyridin-2-yl)oxy}cyclohexyl)pyrrolidine-2-carbonitrile;
(2S,5R)-1-{N-(4-trans(4-bromophenoxy)cyclohexyl)glycyl}-5-ethynylpyrrolidine-2-carbonitrile;
(2S,5R)-1-(N-(4-transhydroxycyclohexyl)glycyl)-5-prop-1-ynylpyrrolidine-2-carbonitrile;
(2S,5S)-1-(N-(4-transhydroxycyclohexyl)glycyl)-5-methylpyrro lidine-2-carbonitrile;
and
6-{[4-({2-[(2S,5R)-2-cyano-5-ethynylpyrrolidin-1-yl]-2-oxoethyl}amino)-4-methylcyclohexyl]oxy}-N,N-dimethylnicotinamide.

11. The compound according to claim 1, wherein
R is cyano;
R1 is a member selected from the group consisting of alkyl, alkenyl, and alkynyl;
R2 is hydrogen;
R3 is alkyl; wherein the alkyl group of R3 is optionally substituted with a member of the group consisting of alkoxy, alkoxycarbonyl, alkoxycarbonylNRa, alkylNRa, carboxy, and hydroxy; and
Ra is a member selected from the group consisting of hydrogen and alkyl.

12. The compound according to claim 11, that is selected from the group consisting of
(2S,5R)-5-ethynyl-1-(N-(1,1,3,3-tetramethylbutyl)glycyl)pyrrolidine-2-carbonitrile;
(2S,5R)-1-(N-(tert-butyl)glycyl)-5-ethynylpyrrolidine-2-carbonitrile;
(2S,5R)-1-(N-(1,1-dimethylpropyl)glycyl)-5-ethynylpyrrolidine-2-carbonitrile;
(2S,5R)-5-ethynyl-1-{N-(3-(methylamino)propyl)glycyl}pyrrolidine-2-carbonitrile;
(2S,5R)-1-(N-(4-tert-butoxycarbonylbutyl)glycyl)-5-ethynylpyrrolidine-2-carbonitrile;
(2S,5R)-5-ethynyl-1-(N-(3-hydroxy-2,2-dimethylpropyl)glycyl)pyrrolidine-2-carbonitrile;
(2S,5R)-5-ethynyl-1-{N-(3-(N-tert-butoxycarbonyl-N-methylamino)propyl)glycyl}pyrrolidine-2-carbonitrile;
(2S,5R)-5-ethynyl-1-(N-(4-carboxybutyl)glycyl)pyrrolidine-2-carbonitrile;

(2S,5R)-5-ethynyl-1-(N-(3-isopropoxypropyl)glycyl)pyrrolidine-2-carbonitrile;

(2S,5S)-1-(N-isopropylglycyl)-5-methylpyrrolidine-2-carbonitrile;

(2S,5S)-1-(N-(tert-butyl)glycyl)-5-methylpyrrolidine-2-carbonitrile; and (2S,5S)-1-[(tert-butylamino)acetyl]pyrrolidine-2,5-dicarbonitrile.

13. The compound according to claim 1, wherein
R is cyano;
R1 is a member selected from the group consisting of alkyl, alkenyl, and alkynyl; and
R2 is hydrogen; and
R3 is a member selected from the group consisting of aryl and heterocycle; wherein said heterocycle is a member selected from the group consisting of azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl.

14. The compound according to claim 13, that is a member selected from the group consisting of
(2S,5R)-5-ethynyl-1-(N-tetrahydro-2H-pyran-4-ylglycyl)pyrrolidine-2-carbonitrile;
(2S,5R)-5-ethynyl-1-(N-tetrahydrofuran-3-ylglycyl)pyrrolidine-2-carbonitrile; and
(2S,5S)-1-(N-2,3-dihydro-1H-inden-1-ylglycyl)-5-methylpyrrolidine-2-carbonitrile.

15. The compound according to claim 1, wherein
R is cyano;
R1 is a member selected from the group consisting of alkyl, alkenyl, and alkynyl; and
R2 is hydrogen; and
R3 is a member selected from the group consisting of arylalkyl and heterocyclealkyl.

16. The compound according to claim 15, that is a member selected from the group of
(2S,5R)-5-ethynyl-1-{N-(2-(4-fluorophenyl)-1,1-dimethylethyl)glycyl}pyrrolidine-2-carbonitrile;
(2S,5S)-1-{N-(2-(3,4-dimethoxyphenyl)ethyl)glycyl}-5-methylpyrrolidine-2-carbonitrile;
(2S,5R)-5-ethynyl-1-(N-(tetrahydrofuran-2-ylmethyl)glycyl)pyrrolidine-2-carbonitrile;
(2S,5R)-5-ethynyl-1-(N-(pyridin-2-ylmethyl)glycylpyrrolidine-2-carbonitrile;
(2S,5R)-5-ethynyl-1-(N-(2-pyridin-4-ylethyl)glycyl)pyrrolidine-2-carbonitrile;
(2S,5R)-5-ethynyl-1-{N-((1-tert-butoxycarbonylpiperidin-4-yl)methyl)glycyl}pyrrolidine-2-carbonitrile;
(2S,5R)-5-ethynyl-1-(N-(4-iodobenzyl)glycyl)pyrrolidine-2-carbonitrile.

17. The compound according to claim 1, wherein
R is cyano,
R1 is a member selected from the group consisting of alkyl, alkenyl, and alkynyl;
R2 is hydrogen;

R3 is

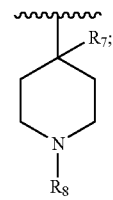

$R_7$ is a member selected from the group consisting of hydrogen, alkyl and alkoxyalkyl;
and
$R_8$ is a member selected from the group consisting of hydrogen, alkylcarbonyl, aryl and heterocycle.

18. The compound according to claim 17, that is a member selected from the group consisting of
(2S,5R)-5-ethynyl-1-(N-(4-methyl-1-pyridin-2-ylpiperidin-4-yl)glycyl)pyrrolidine-2-carbonitrile;
(2S,5R)-5-ethynyl-1-(N-(4-methyl-1-(3-cyano-pyridin-2-yl)piperidin-4-yl)glycyl)pyrrolidine-2-carbonitrile;
(2S,5R)-5-ethynyl-1-(N-(1-(3-cyano-pyridin-3-yl)piperidin-4-yl)glycyl)pyrrolidine-2-carbonitrile;
(2S,5R)-5-ethynyl-1-{N-(4-methyl-1-(4-carboxy-pyridin-2-yl)piperidin-4-yl)glycylpyrrolidine-2-carbonitrile;
(2S,5R)-5-ethynyl-1-(N-{4-methyl-1-(5-(trifluoromethylpyridin-2-yl)piperidin-4-yl}glycyl)pyrrolidine-2-carbonitrile;
(2S,5R)-1-{N-(1-(5-chloropyridin-2-yl)-4-methylpiperidin-4-yl)glycyl}-5-ethynylpyrrolidine-2-carbonitrile;
(2S,5R)-5-ethynyl-1-(N-(1-pyridin-2-ylpiperidin-4-yl)glycyl)pyrrolidine-2-carbonitrile;
(2S,5R)-5-ethynyl-1-(N-{4-methyl-1-(4-(trifluoromethyl)pyrimidin-2-yl)piperidin-4-yl glycyl)pyrrolidine-2-carbonitrile;
(2S,5R)-5-ethynyl-1-(N-(4-methyl-1-(5-carboxy-pyridin-2-yl)piperidin-4-yl)glycyl)pyrrolidine-2-carbonitrile;
(2S,5R)-5-ethynyl-1-(N-(4-methyl-1-(5-cyano-pyridin-3-yl)piperidin-4-yl)glycyl)pyrrolidine-2-carbonitrile;
(2S,5R)-5-ethynyl-1-(N-(1-tert-butoxycarbonyl-piperidin-4-yl)glycyl)pyrrolidine-2-carbonitrile;
(2S,5R)-5-ethynyl-1-(N-(1-5-cyano-pyridin-2-ylpiperidin-4-yl)glycyl)pyrrolidine-2-carbonitrile;
(2S,5R)-1-{N-(1-(3-cyanophenyl)-4-methylpiperidin-4-yl)glycyl}-5-ethynylpyrrolidine-2-carbonitrile;
(2S,5R)-5-ethynyl-1-(N-{4-methyl-1-(4-(trifluoromethyl)pyridin-2-ylpiperidin-4-yl}glycyl)pyrrolidine-2-carbonitrile;
(2S,5R)-5-ethynyl-1-(N-piperidin-4-ylglycyl)pyrrolidine-2-carbonitrile; and
(2S,5R)-5-ethynyl-1-({[4-methyl-1-(5-nitropyridin-2-yl)piperidin-4-yl]amino}acetyl)pyrrolidine-2-carbonitrile; and
(2S,5R)-5-ethynyl-1-[({4-methyl-1-[5-(methylsulfonyl)pyridin-2-yl]piperidin-4-yl}amino)acetyl]pyrrolidine-2-carbonitrile.

19. The compound according to claim 1, wherein
R is cyano;
R1 is selected from the group consisting of alkyl, alkenyl, and alkynyl; and R2 is hydrogen; and
R3 is

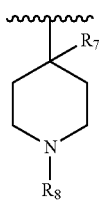

R7 is a member selected from the group consisting of hydrogen, alkyl and alkoxyalkyl; and R8 is a member selected from the group consisting of arylcarbonyl and heterocyclecarbonyl.

20. The compound according to claim 19, that is a member selected from the group consisting of
 (2S,5R)-5-ethynyl-1-{N-(4-methyl-1-(4-methoxycarbonylbenzoyl)piperidin-4-yl)glycyl}pyrr-olidine-2-carbonitrile;
 (2S,5R)-1-{N-(1-(4-chlorobenzoyl)piperidin-4-yl)glycyl}-5-ethynylpyrrolidine-2-carbonitrile;
 (2S,5R)-5-ethynyl-1-(N-(1-isonicotinoyl-4-methylpiperidin-4-yl) glycyl)pyrrolidine-2-carbonitrile;
 (2S,5R)-1-{N-(1-(4-chlorobenzoyl)-4-methylpiperidin-4-yl)glycyl}-5-ethynylpyrrolidine-2-carbonitrile;
 (2S,5R)-1-{N-(1-(4-cyanobenzoyl)-4-methylpiperidin-4-yl)glycyl}-5-ethynylpyrrolidine-2-carbonitrile;
 (2S,5R)-1-{N-(1-(4-bromobenzoyl)-4-methylpiperidin-4-yl)glycyl}-5-ethynylpyrrolidine-2-carbonitrile.

21. The compound according to claim 1, wherein
R is cyano;
R1 is a member selected from the group consisting of alkyl, alkenyl, alkynyl, allenyl and cycloalkyl; and
R2 is hydrogen; and
R3 is a member selected from the group consisting of aryl-O-alkyl-, aryl-NH-alkyl-, heterocycle-O-alkyl- and heterocycle-NH-alkyl-.

22. The compound according to claim 21, that is a member selected from the group consisting of
 (2S,5R)-1-{N-(1,1-dimethyl-2-(5-cyano-pyridin-2-yloxy)ethyl)glycyl}-5-ethynylpyrrolidine-2-carbonitrile;
 (2S,5R)-1-{N-(1,1-dimethyl-2-(quinolin-4-ylamino)ethyl)glycyl}-5-ethynylpyrrolidine-2-carbonitrile;
 (2S,5R)-1-{N-(2-(1,3-benzothiazol-2-ylamino)-1,1-dimethylethylglycyl}-5-ethynylpyrrolidine-2-carbonitrile;
 (2S,5R)-1-(N-{1,1-dimethyl-2-(3-cyano-6-methylpyridin-2-ylamino)ethyl}glycyl)-5-ethynylpyrrolidine-2-carbonitrile;
 (2S,5R)-1-(N-(1,1-dimethyl-2-{(5-(trifluoromethyl)pyridin-2-yl)oxy}ethyl)glycyl)-5-ethynylpyrrolidine-2-carbonitrile;
 (2S,5R)-1-(N-{1,1-dimethyl-2-((3-cyano-6-methylpyridin-2-yl)oxy)ethyl}glycyl)-5-ethynylpyrrolidine-2-carbonitrile;
 (2S,5R)-1-{N-(1,1-dimethyl-2-(3-cyanopyridin-2-ylamino)ethyl)glycyl}-5-ethynylpyrrolidine-2-carbonitrile;
 (2S,5R)-1-(N-(1,1-dimethyl-2-{(4-(trifluoromethyl)pyrimidin-2-yl)amino}ethyl)glycyl)-5-ethynylpyrrolidine-2-carbonitrile;
 (2S,5R)-1-{N-(1,1-dimethyl-2-(5-methoxycarbonylpyridin-2-ylamino)ethyl)glycyl}-5-ethynylpyrrolidine-2-carbonitrile;
 (2S,5R)-1-{N-(2-(2-cyano-5-fluorophenoxy)-1,1-dimethylethyl)glycyl}-5-ethynylpyrrolidine-2-carbonitrile;
 (2S,5R)-1-(N-(2-{(3-chloro-5-(trifluoromethyl)pyridin-2-yl)amino}ethyl)glycyl)-5-ethynylpyrrolidine-2-carbonitrile;
 (2S,5R)-1-(N-(1,1-dimethyl-2-(5-cyano-pyridin-2-ylamino)ethyl)glycyl}-5-ethynylpyrrolidine-2-carbonitrile;
 (2S,5R)-1-(N-(2-(4-carboxy-anilino)-1,1-dimethylethyl)glycyl)-5-ethynylpyrrolidine-2-carbonitrile;
 (2S,5S)-5-methyl-1-{N-(2-(5-cyano-pyridin-2-ylamino)ethyl)glycyl}pyrrolidine-2-carbonitrile.

23. The compound according to claim 1, wherein
R is cyano;
R1 is selected from the group consisting of alkyl, alkenyl, and alkynyl; and
R2 and R3 taken together with the atoms they are attached form a mono or bicyclic heterocycle selected from the group consisting of 3-isoquinoline, 2-pyrrolidinyl, 2-quinolinyl, 2-tetrahydroquinolinyl, and 3-tetrahydroisoquinolinyl.

24. The compound according to claim 23, that is a member selected from the group consisting of
 (2S,5R)-5-ethynyl-1-((3S)-1,2,3,4-tetrahydroisoquinolin-3-ylcarbonyl)pyrrolidine-2-carbonitrile;
 (2S,5S)-4,4-difluoro-5-methyl-1-((5S)-5-methyl-L-prolyl)pyrrolidine-2-carbonitrile;
 (2S,5S)-5-methyl-1-((3S)-1,2,3,4-tetrahydroisoquinolin-3-ylcarbonyl)pyrrolidine-2-carbonitrile;
 (2S,5S)-5-methyl-1-L-prolyl)pyrrolidine-2-carbonitrile;
 5S)-5-methyl-1-((5S)-5-methyl-L-prolyl)pyrrolidine-2-carbonitrile.

25. A method of treating diabetes, comprising administration of a therapeutically effective amount of a compound of formula (I) as described in claim 1.

26. A method of treating type II diabetes, comprising administration of a therapeutically effective amount of a compound of formula (I) as described in claim 1.

27. A method of treating hyperglycemia, comprising administration of a therapeutically effective amount of a compound of formula (I) as described in claim 1.

28. A method of treating Syndrome X, comprising administration of a therapeutically effective amount of a compound of formula (I) as described in claim 1.

29. A method of treating hyperisulinemia, comprising administration of a therapeutically effective amount of a compound of formula (I) as described in claim 1.

30. A method of treating obesity, comprising administration of a therapeutically effective amount of a compound of formula (I) as described in claim 1.

* * * * *